US012614768B2

(12) United States Patent
Porterfield et al.

(10) Patent No.: US 12,614,768 B2
(45) **Date of Patent: \*Apr. 28, 2026**

(54) BATTERY OUTGASSING DETECTOR

(71) Applicant: Kidde Technologies Inc., Wilson, NC (US)

(72) Inventors: John W. Porterfield, Rolesville, NC (US); Robert Dunster, Slough (GB); Albert C. Rouse, Prior Lake, MN (US); John Lewis, Elm City, NC (US); Barret Stein, Raleigh, NC (US)

(73) Assignee: Kidde Technologies Inc., Wilson, NC (US)

( * ) Notice: Subject to any disclaimer, the term of this patent is extended or adjusted under 35 U.S.C. 154(b) by 511 days.

This patent is subject to a terminal disclaimer.

(21) Appl. No.: 18/083,510

(22) Filed: Dec. 17, 2022

(65) Prior Publication Data

US 2024/0204271 A1      Jun. 20, 2024

(51) Int. Cl.
H01M 10/48       (2006.01)
A62C 3/16        (2006.01)
(Continued)

(52) U.S. Cl.
CPC .............. H01M 10/48 (2013.01); A62C 3/16 (2013.01); A62C 37/40 (2013.01); G01N 33/004 (2013.01);
(Continued)

(58) Field of Classification Search
CPC ..... H01M 10/48; H01M 2220/20; A62C 3/16; A62C 37/40; G01N 33/004; G01N 33/005; G01N 33/0063
(Continued)

(56) References Cited

U.S. PATENT DOCUMENTS 6,204,769 B1    3/2001  Arai et al.
9,478,834 B2    10/2016  Sweetland et al.
(Continued)

FOREIGN PATENT DOCUMENTS

CA         2867531 A1     1/2014
CN         102461354 A    5/2012
(Continued)

OTHER PUBLICATIONS

Extended European Search Report for EP Application No. 23217224. 7, dated Apr. 15, 2024, 7 pages.
(Continued)

*Primary Examiner* — Huy Q Phan
*Assistant Examiner* — Trung Q Nguyen
(74) *Attorney, Agent, or Firm* — Kinney & Lange, P.A.

(57)      ABSTRACT

A system for detecting gas leakage within a battery pack includes a battery pack, a controller, and a detector. The battery pack comprises a plurality of cells which may be subject to a gas leakage. The detector is configured to sense a concentration value of one or more gases. The detector is further configured to generate a return signal indicative of no alarm, a first alarm level, or a second alarm level. The detector is electrically connected to the controller and is configured to transmit the return signal to the controller. The controller is configured to output a first alarm level or a second alarm level in response to the return signal. Emergency response procedures may be implemented based on the level of gas leakage within the battery pack indicated.

20 Claims, 18 Drawing Sheets

(51) Int. Cl.
    *A62C 37/40*         (2006.01)
    *G01N 33/00*         (2006.01)

(52) U.S. Cl.
    CPC ....... *G01N 33/005* (2013.01); *G01N 33/0063*
               (2013.01); *H01M 2220/20* (2013.01)

(58) Field of Classification Search
    USPC .............................. 324/500, 600, 76.11, 464
    See application file for complete search history.

(56)                 References Cited

U.S. PATENT DOCUMENTS

| | | | |
|---|---|---|---|
| 10,507,345 | B2 | 12/2019 | Klassen et al. |
| 10,877,011 | B2 | 12/2020 | Cummings et al. |
| 11,183,733 | B2 | 11/2021 | Coreth et al. |
| 11,276,891 | B2 | 3/2022 | Dhanani et al. |
| 11,833,377 | B2 | 12/2023 | Ginder et al. |
| 12,107,295 | B2 | 10/2024 | Fan |
| 2012/0312562 | A1 | 12/2012 | Woehrle et al. |
| 2013/0071706 | A1 | 3/2013 | Lee |
| 2013/0312947 | A1 | 11/2013 | Bandhauer et al. |
| 2014/0242422 | A1 | 8/2014 | Hakansson et al. |
| 2016/0126535 | A1 | 5/2016 | Qiao et al. |
| 2018/0366717 | A1* | 12/2018 | Hu ...................... H01M 50/176 |
| 2019/0151691 | A1 | 5/2019 | Adrain |
| 2020/0112016 | A1* | 4/2020 | Erhart ................. H01M 50/209 |
| 2020/0266405 | A1* | 8/2020 | Pokora ................ H01M 10/486 |
| 2021/0151808 | A1* | 5/2021 | Feng ................. H01M 10/6567 |
| 2021/0245627 | A1 | 8/2021 | Ferguson et al. |
| 2021/0283441 | A1 | 9/2021 | Cao et al. |
| 2021/0391611 | A1 | 12/2021 | Zhamu et al. |
| 2022/0040515 | A1 | 2/2022 | Critchley |
| 2022/0085428 | A1* | 3/2022 | Engle ................. H01M 10/443 |
| 2022/0111237 | A1 | 4/2022 | Paulin |
| 2022/0280823 | A1 | 9/2022 | Baeder et al. |
| 2022/0407174 | A1 | 12/2022 | Sandahl et al. |
| 2023/0040106 | A1* | 2/2023 | Youn ................. H01M 10/4285 |
| 2023/0142289 | A1* | 5/2023 | Wang ................. H01M 10/482 |
| | | | 429/90 |
| 2023/0277883 | A1 | 9/2023 | Spencer et al. |
| 2024/0091575 | A1 | 3/2024 | Shin |
| 2024/0198152 | A1 | 6/2024 | Porterfield et al. |
| 2024/0198153 | A1 | 6/2024 | Porterfield et al. |
| 2024/0204271 | A1 | 6/2024 | Porterfield et al. |
| 2025/0170441 | A1 | 5/2025 | Troutt |

FOREIGN PATENT DOCUMENTS

| | | |
|---|---|---|
| CN | 109961602 A | 7/2019 |
| CN | 110227224 A | 9/2019 |
| CN | 111330190 A | 6/2020 |
| CN | 112316332 A | 2/2021 |
| CN | 113599742 A | 11/2021 |
| CN | 114028748 A | 2/2022 |
| CN | 114069078 A | 2/2022 |
| CN | 111987258 B | 3/2022 |
| CN | 216366395 U | 4/2022 |
| CN | 114839555 A | 8/2022 |
| CN | 114899511 A | 8/2022 |
| CN | 116429978 A | 7/2023 |
| DE | 4412447 A1 | 10/1995 |
| DE | 102020131108 A1 | 5/2022 |
| EP | 2289720 A1 | 3/2011 |
| EP | 3476645 A1 | 5/2019 |
| JP | 2009099305 A | 5/2009 |
| KR | 20220137208 A | 10/2022 |
| WO | 2010025761 A1 | 3/2010 |
| WO | 2013020704 A1 | 2/2013 |
| WO | 2014069022 A1 | 5/2014 |
| WO | 2018006102 A2 | 1/2018 |
| WO | 2021108048 A1 | 6/2021 |
| WO | 2022009120 A1 | 1/2022 |
| WO | 2022032160 A1 | 2/2022 |
| WO | 2022197332 A1 | 9/2022 |

OTHER PUBLICATIONS

Extended European Search Report for EP Application No. 23217655.2, dated Apr. 15, 2024, 7 pages.
Extended European Search Report for EP Application No. 23217775.8, dated Apr. 17, 2024, 6 pages.
Extended European Search Report for EP Application No. 23217782.4, dated Apr. 17, 2024, 7 pages.
Extended European Search Report for European Patent Application No. 23217195.9, dated May 13, 2024.
Extended European Search Report for European Patent Application No. 23217198.3, dated Apr. 23, 2024, 8 pages.
Extended European Search Report for European Patent Application No. 23217290.8, dated Apr. 23, 2024, 9 pages.
G. Pienta, "Basic Chemistry and Physics of Fire", from Fire Protection Systems 3rd Edition, Chapter 2, Published by American Soc. of Plumbing Engineers ASPE, 2016, pp. 9-12.

* cited by examiner

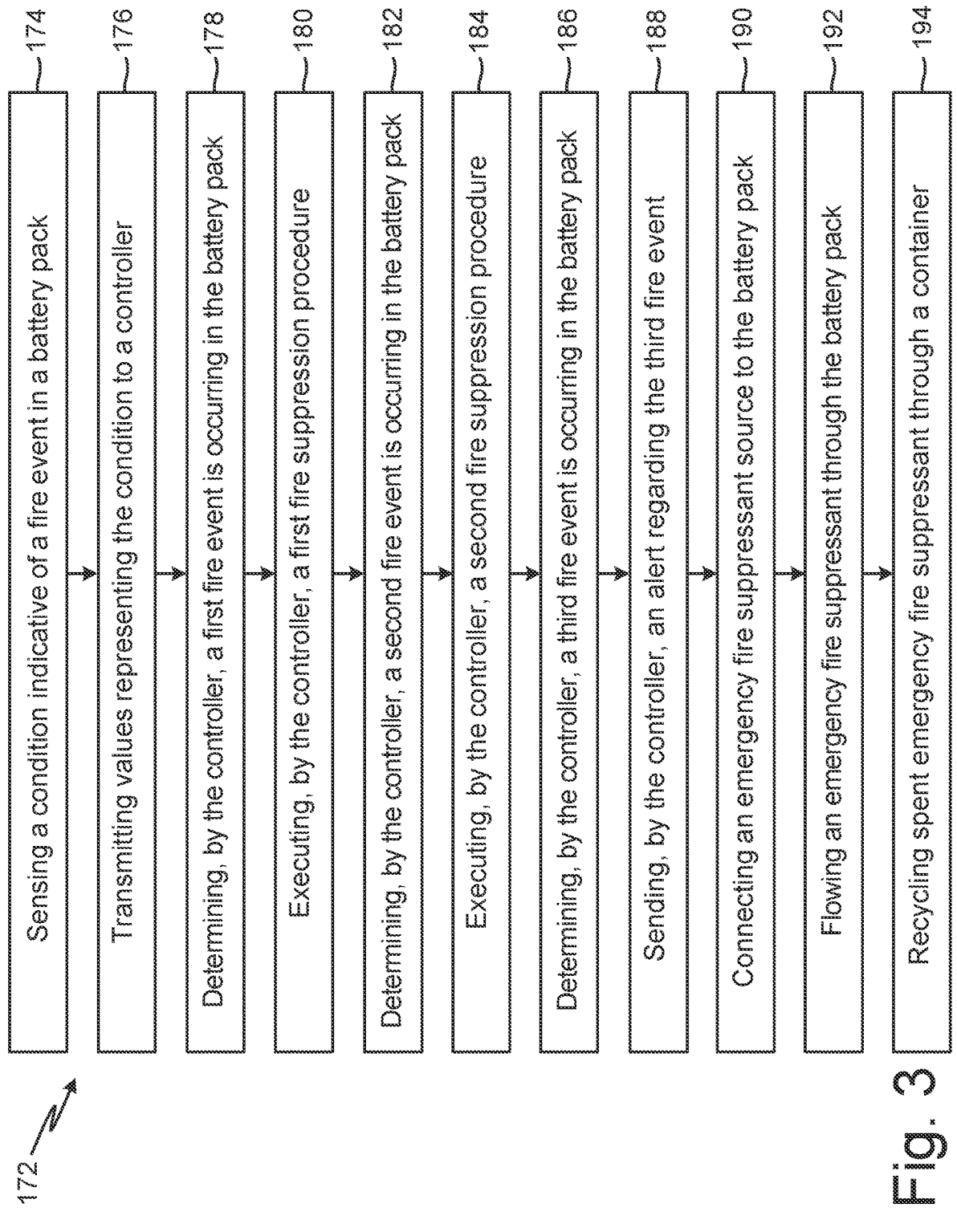

174 — Sensing a condition indicative of a fire event in a battery pack

176 — Transmitting values representing the condition to a controller

178 — Determining, by the controller, a first fire event is occurring in the battery pack 180 — Executing, by the controller, a first fire suppression procedure 182 — Determining, by the controller, a second fire event is occurring in the battery pack 184 — Executing, by the controller, a second fire suppression procedure 186 — Determining, by the controller, a third fire event is occurring in the battery pack 188 — Sending, by the controller, an alert regarding the third fire event 190 — Connecting an emergency fire suppressant source to the battery pack 192 — Flowing an emergency fire suppressant through the battery pack 194 — Recycling spent emergency fire suppressant through a container

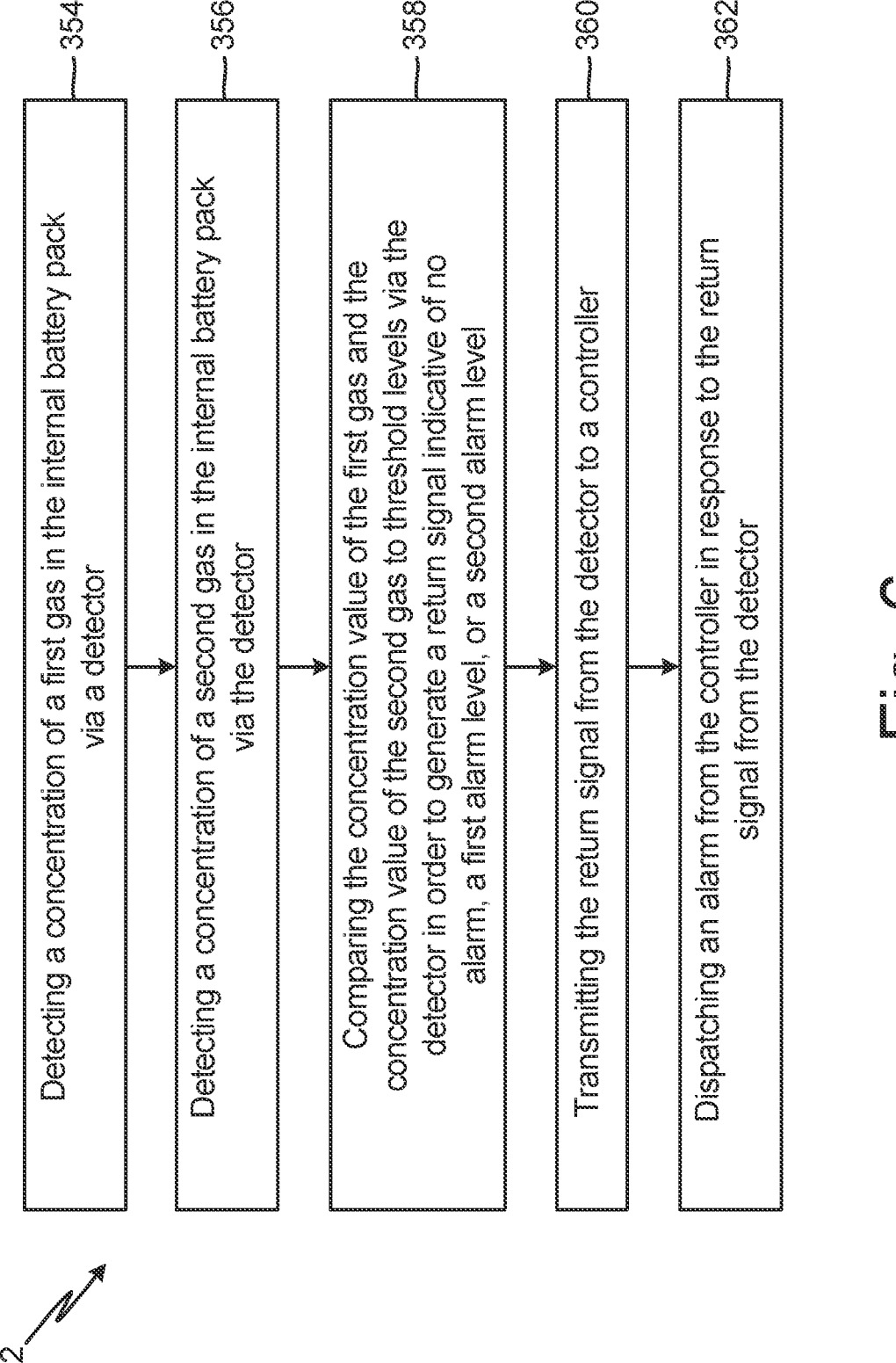

354 Detecting a concentration of a first gas in the internal battery pack via a detector 356 Detecting a concentration of a second gas in the internal battery pack via the detector 358 Comparing the concentration value of the first gas and the concentration value of the second gas to threshold levels via the detector in order to generate a return signal indicative of no alarm, a first alarm level, or a second alarm level 360 Transmitting the return signal from the detector to a controller 362 Dispatching an alarm from the controller in response to the return signal from the detector

Fig. 6

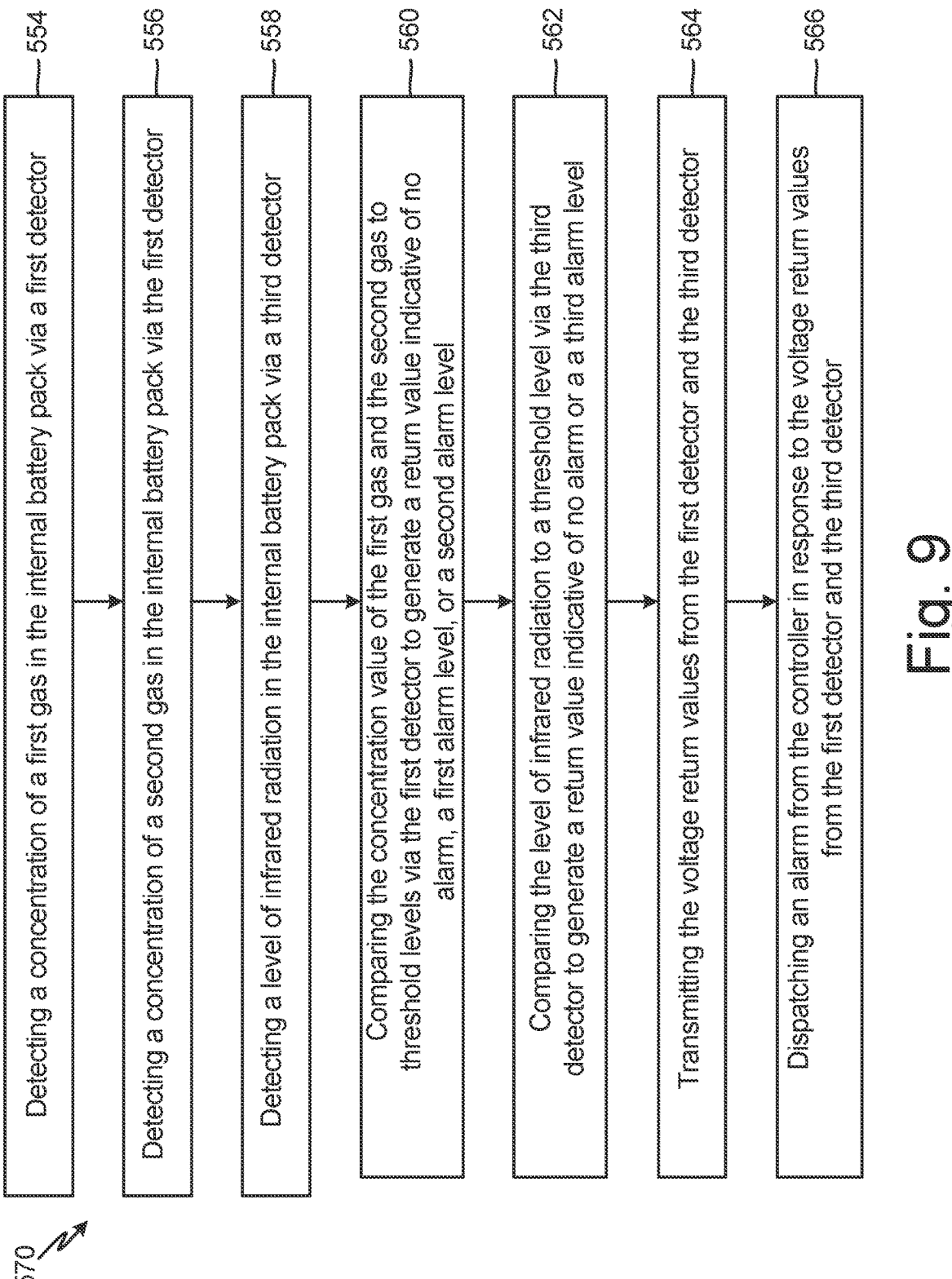

554 — Detecting a concentration of a first gas in the internal battery pack via a first detector 556 — Detecting a concentration of a second gas in the internal battery pack via the first detector 558 — Detecting a level of infrared radiation in the internal battery pack via a third detector 560 — Comparing the concentration value of the first gas and the second gas to threshold levels via the first detector to generate a return value indicative of no alarm, a first alarm level, or a second alarm level 562 — Comparing the level of infrared radiation to a threshold level via the third detector to generate a return value indicative of no alarm or a a third alarm level 564 — Transmitting the voltage return values from the first detector and the third detector 566 — Dispatching an alarm from the controller in response to the voltage return values from the first detector and the third detector

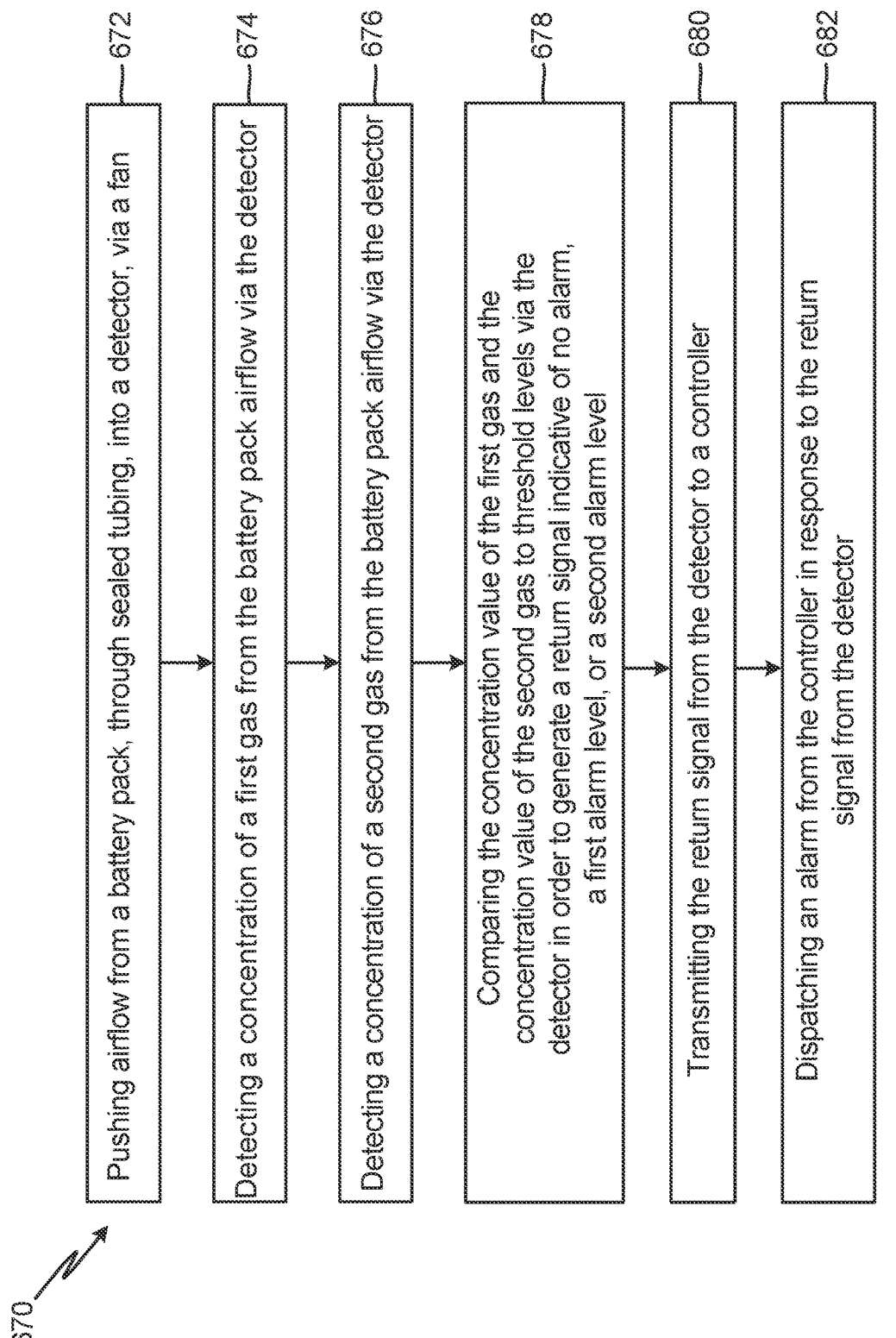

Pushing airflow from a battery pack, through sealed tubing, into a detector, via a fan — 672

Detecting a concentration of a first gas from the battery pack airflow via the detector — 674

Detecting a concentration of a second gas from the battery pack airflow via the detector — 676

Comparing the concentration value of the first gas and the concentration value of the second gas to threshold levels via the detector in order to generate a return signal indicative of no alarm, a first alarm level, or a second alarm level — 678

Transmitting the return signal from the detector to a controller — 680

Dispatching an alarm from the controller in response to the return signal from the detector — 682

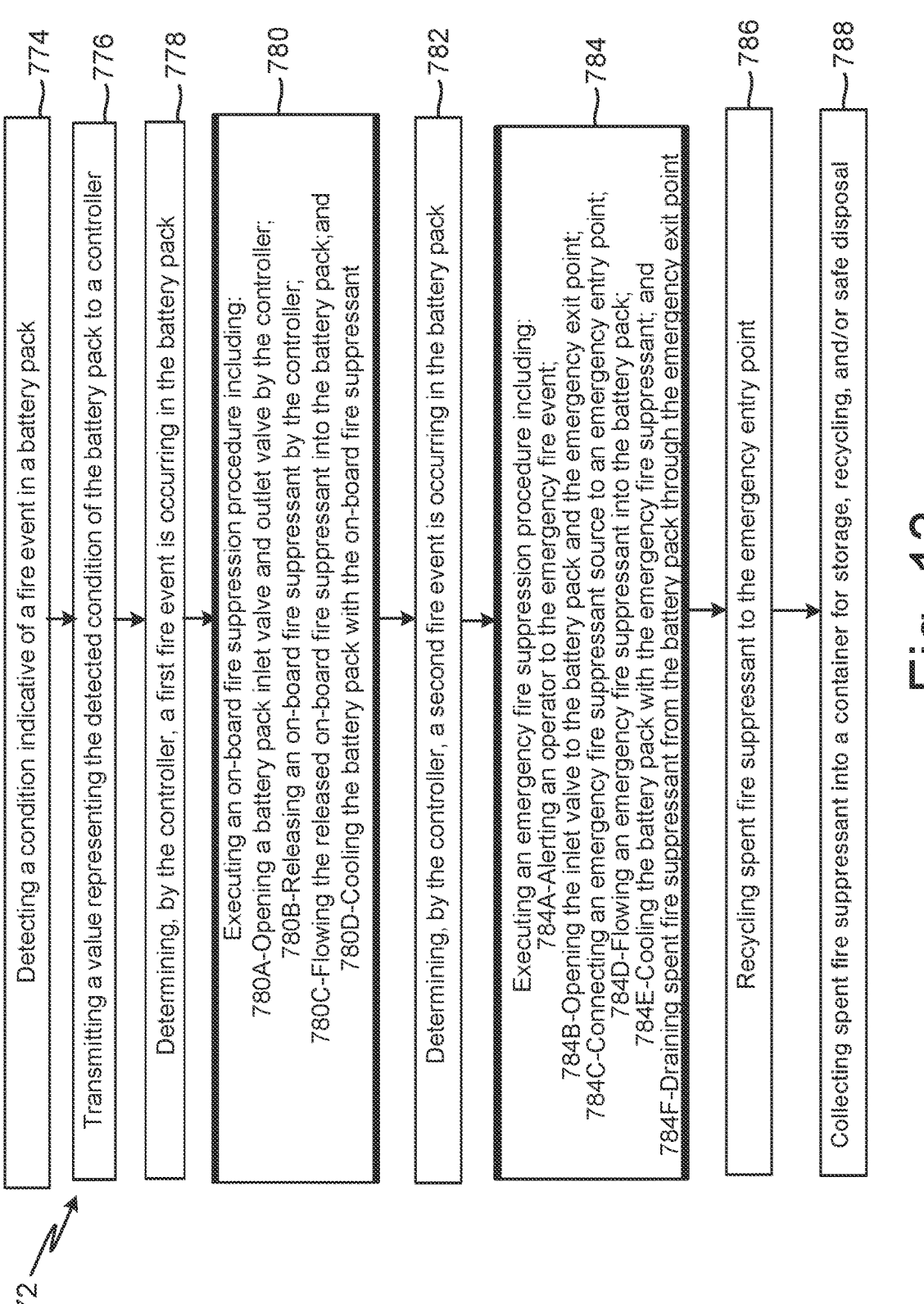

772

774 — Detecting a condition indicative of a fire event in a battery pack

776 — Transmitting a value representing the detected condition of the battery pack to a controller 778 — Determining, by the controller, a first fire event is occurring in the battery pack 780 — Executing an on-board fire suppression procedure including:
780A-Opening a battery pack inlet valve and outlet valve by the controller;
780B-Releasing an on-board fire suppressant by the controller;
780C-Flowing the released on-board fire suppressant into the battery pack;and
780D-Cooling the battery pack with the on-board fire suppressant 782 — Determining, by the controller, a second fire event is occurring in the battery pack 784 — Executing an emergency fire suppression procedure including:
784A-Alerting an operator to the emergency fire event;
784B-Opening the inlet valve to the battery pack and the emergency fire event;
784C-Connecting an emergency fire suppressant source to an emergency entry point;
784D-Flowing an emergency fire suppressant into the battery pack;
784E-Cooling the battery pack with the emergency fire suppressant; and
784F-Draining spent fire suppressant from the battery pack through the emergency exit point 786 — Recycling spent fire suppressant to the emergency entry point 788 — Collecting spent fire suppressant into a container for storage, recycling, and/or safe disposal

Fig. 13

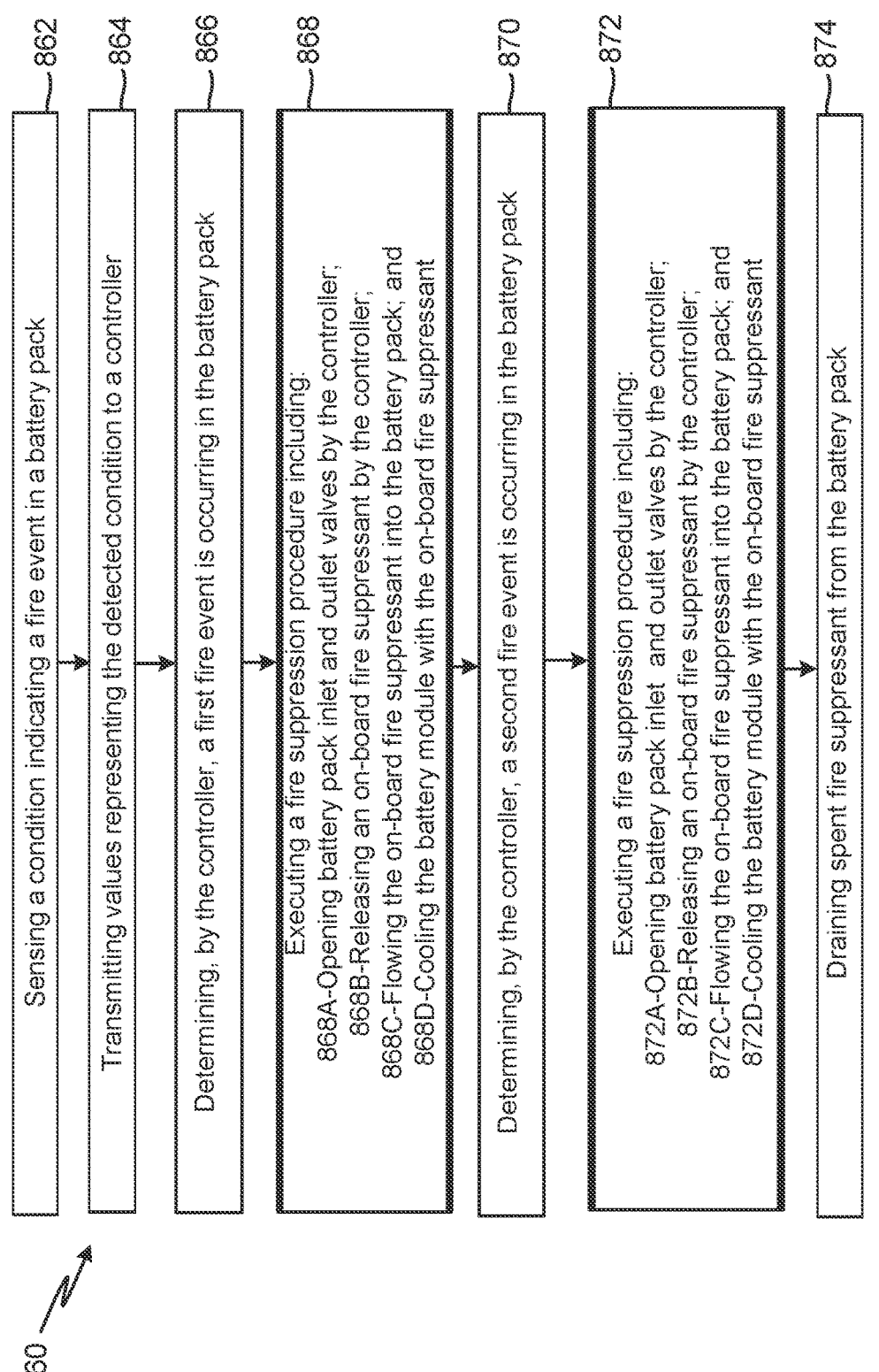

862 — Sensing a condition indicating a fire event in a battery pack

864 — Transmitting values representing the detected condition to a controller

866 — Determining, by the controller, a first fire event is occurring in the battery pack 868 — Executing a fire suppression procedure including:
868A-Opening battery pack inlet and outlet valves by the controller;
868B-Releasing an on-board fire suppressant by the controller;
868C-Flowing the on-board fire suppressant into the battery pack; and
868D-Cooling the battery module with the on-board fire suppressant 870 — Determining, by the controller, a second fire event is occurring in the battery pack 872 — Executing a fire suppression procedure including:
872A-Opening battery pack inlet and outlet valves by the controller;
872B-Releasing an on-board fire suppressant by the controller;
872C-Flowing the on-board fire suppressant into the battery pack; and
872D-Cooling the battery module with the on-board fire suppressant 874 — Draining spent fire suppressant from the battery pack

BATTERY OUTGASSING DETECTOR

CROSS-REFERENCE TO RELATED APPLICATION(S)

This application is related to U.S. application Ser. No. 18/083,511, filed on Dec. 17,2022, entitled "LITHIUM ION BATTERY GAS AND OPTICAL DETECTOR," the disclosure of which is incorporated by reference in its entirety. This application is related to U.S. application Ser. No. 18/083,512, filed on Dec. 17, 2022, entitled "DUCTED GAS DETECTOR," the disclosure of which is incorporated by reference in its entirety. This application is related to U.S. application Ser. No. 18/083,513, filed on Dec. 17, 2022, entitled "BATTERY CELL FIRE SUPPRESSION SYSTEM," the disclosure of which is incorporated by reference in its entirety. This application is related to U.S. application Ser. No. 18/083,514, filed on Dec. 17, 2022, entitled "EMERGENCY FIRE SUPPRESSION SYSTEM," the disclosure of which is incorporated by reference in its entirety. This application is related to U.S. application Ser. No.18/083,516, filed on Dec. 17,2022, entitled "DRY CHEMICAL FIRE SUPPRESSANT FOR BATTERY CELLS," the disclosure of which is incorporated by reference in its entirety. This application is related to U.S. application Ser. No. 18/083517, filed on Dec. 17, 2022, entitled "ORGANIC CHEMICAL FIRE SUPPRESSANT FOR BATTERY CELLS," the disclosure of which is incorporated by reference in its entirety.

BACKGROUND

A battery pack mounted on a vehicle typically includes many individual battery cells arranged in series and in parallel. The individual cells may rupture due to unfavorable external or internal battery conditions. A failing battery cell may leak gaseous matter into the surrounding battery pack. In the case of a gas leak, a battery may be subject to a fire event, and in extreme cases, an explosion, which may propagate to other nearby battery cells. Therefore, a system for detecting quantities of gas leakage in a battery pack is desirable.

SUMMARY

A gas detection system for a battery pack, includes a battery pack including a plurality of cells, a controller, and a detector. The detector is configured to sense a concentration value of one or more gases. The detector is electrically connected to the controller. The detector is configured to generate an alarm level return signal indicative of no alarm, a first alarm level, or a second alarm level based upon the concentration value of the one or more gases. The first detector is configured to transmit the alarm level return signal to the controller. The controller is configured to output no alarm, the first alarm, or the second alarm based upon the alarm level return signal received from the first detector.

A method for detecting cell failure within the battery pack includes: sensing a concentration value of a first gas within a battery pack using a detector and sensing a concentration value of a second gas within a battery pack using the detector. The method further includes generating an alarm level return signal using the first detector based upon the first gas concentration value and the second gas concentration value. The alarm level return signal is indicative of no alarm, a first alarm, or a second alarm. The method further includes transmitting the alarm level return signal from the first detector to a controller and outputting no alarm, the first alarm, or the second alarm, via the controller, based upon the voltage return value from the first detector.

BRIEF DESCRIPTION OF THE DRAWINGS

Battery Pack 20
FIG. 3 is a flow chart showing a method utilizing the fire suppression system of FIG. 2.
Gas Detection Systems 250 and 350
FIG. 6 is a method flowchart depicting a method for evaluating and responding to a level of gas within a battery pack.
Gas and Infrared Detection Systems 450 and 550
FIG. 9 is a flowchart for a method for evaluating and responding to a level of gas and infrared radiation within a battery pack.
Remote Gas Detection System 650
FIG. 11 is a flowchart showing a method for evaluating and responding to a level of gas within a battery pack.
Emergency Fire Suppression System 700
FIG. 13 is a flow chart showing a method of utilizing the fire suppression system of FIG. 12.
Multiple on-Board Suppressant System 800
FIG. 15 is a flow chart showing a method of utilizing the fire suppression system of FIG. 14.
Fire Suppressant Chemical Mixtures 900 and 930

DETAILED DESCRIPTION

In general, the present disclosure relates to a fire suppression system for a battery pack or packs installed in a vehicle. The fire suppression system for the battery pack or packs includes detectors, a controller, an on-board fire suppression system, and an emergency fire suppression system.

Different embodiments of the fire suppression system are described in detail below. The different embodiments of the fire suppression system can include: a gas detector with multiple alarm levels; an infrared radiation detector; gas and/or infrared radiation detectors placed inside a battery module; gas detectors placed at a port in a battery module;

gas detectors placed in ducting fluidly connected to a battery module; an on-board fire suppressant system with multiple fire suppressant vessels; an emergency entry point for an emergency fire suppressant to enter a fire suppression system; and methods of use for the embodiments. These embodiments are included as examples and are not intended to be limiting. The fire suppressant system can have any suitable design and can be used for any suitable purpose in other embodiments. The features of each embodiment can be combined and/or substituted with features of any other embodiment, unless explicitly disclosed otherwise.

Battery Pack 24

Figure 1A:
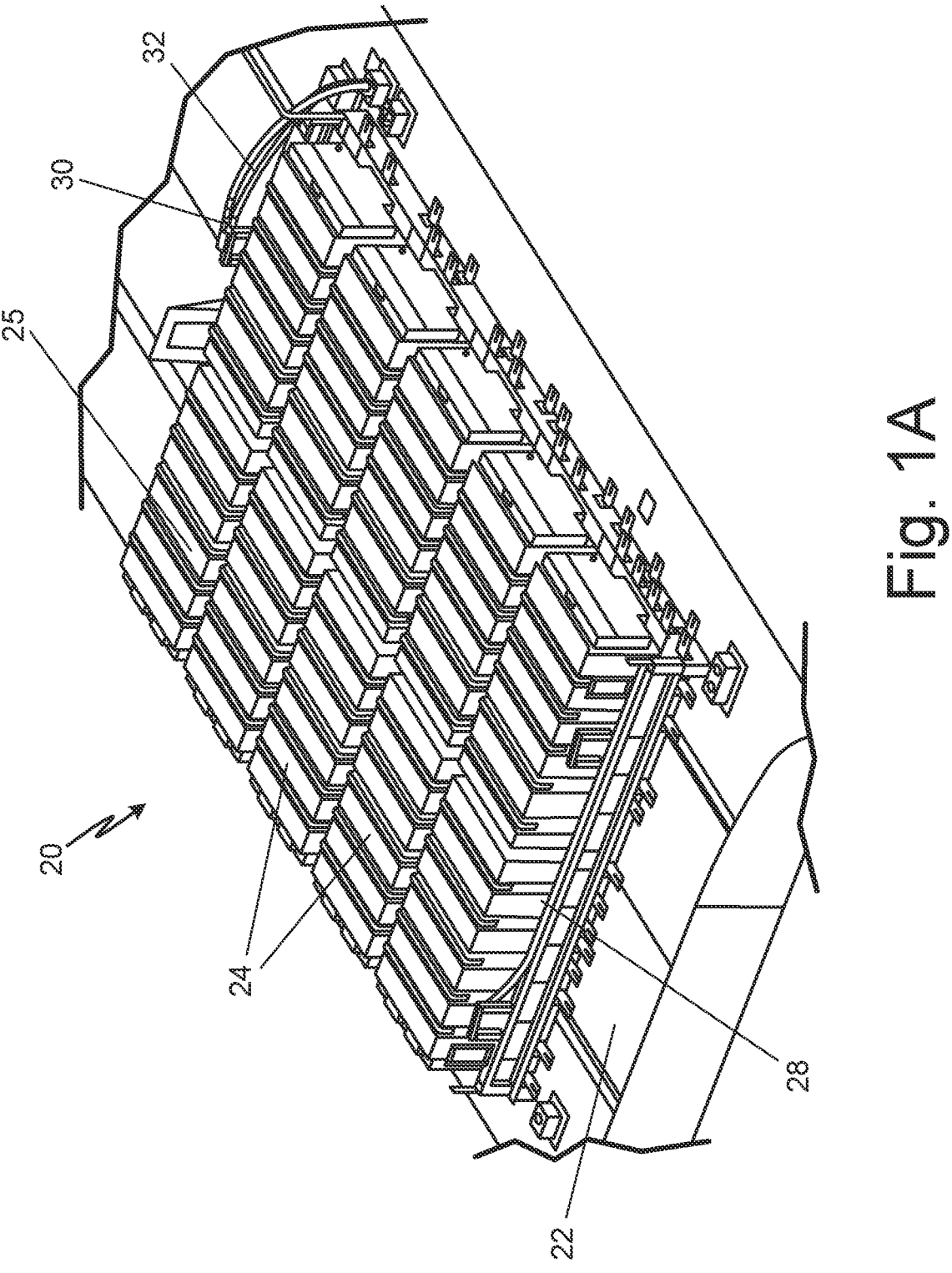
FIG. 1A is an isometric view of a lithium-ion (Li-ion) battery pack installed in a vehicle.
Figure 1B:
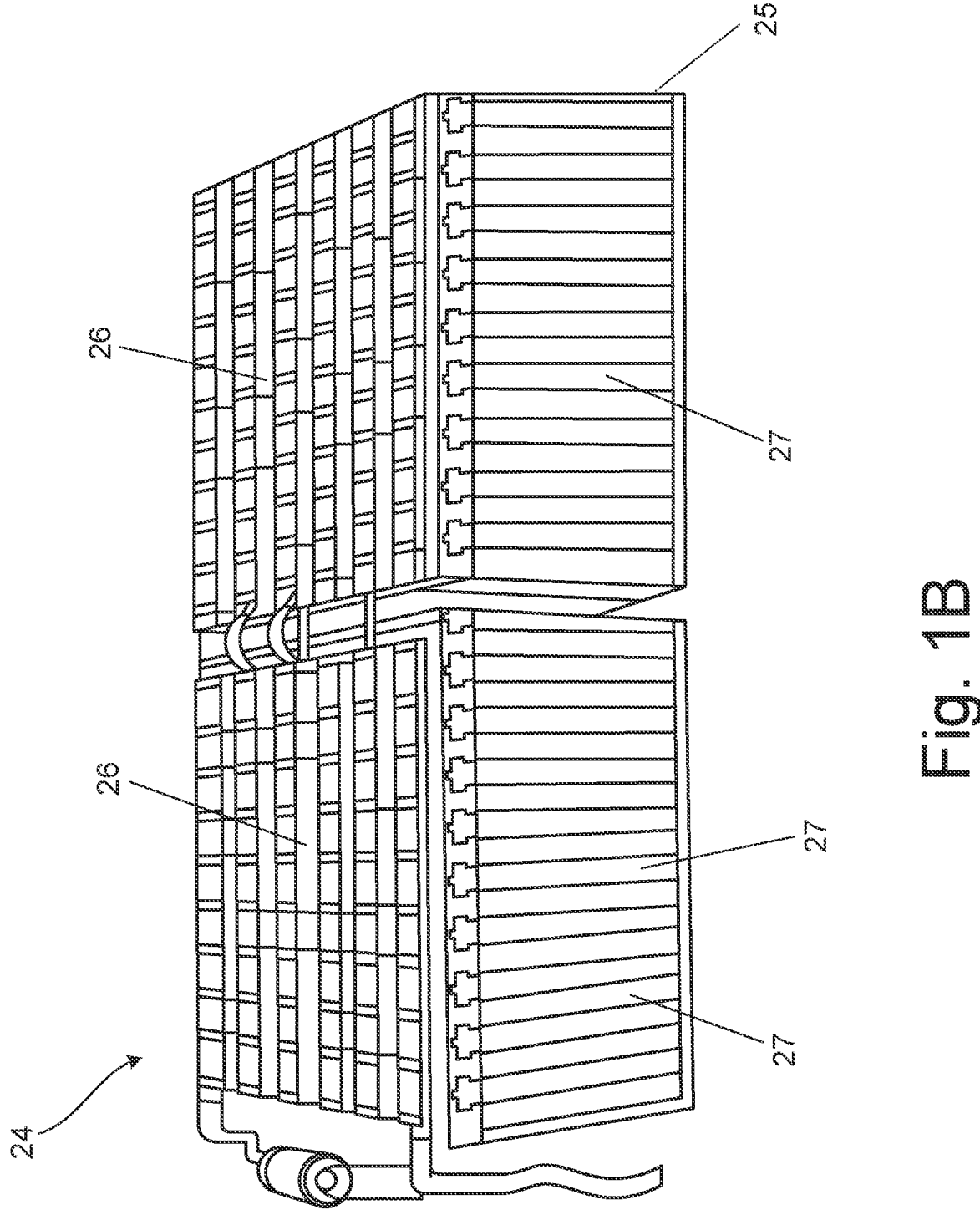
FIG. 1B is a cut-away isometric view of one battery pack.
Fire Suppression System 100

FIG. 1A is an isometric view of battery storage area 20 in vehicle 22 with multiple lithium-ion (Li-ion) battery packs 24. FIG. 1B is a cut-away isometric view of one battery pack 24. Battery packs 24 include enclosures 25, battery modules 26 (shown in FIG. 1B), battery cells 27 (shown in FIG. 1B), electrical connections 28 (shown in FIG. 1A), inlet line 30 (shown in FIG. 1A), and outlet line 32 (shown in FIG. 1A). FIGS. 1A-1B will be discussed together.

Battery pack 24 is installed in vehicle 22. In FIG. 1A, vehicle 22 is an aircraft. In other examples, vehicle 22 is an electrical automobile or other electrical vehicle employing Li-ion batteries for propulsion or storage. Ten battery packs 24 are installed in vehicle 22. Each battery pack 24 has an enclosure 25 to encase battery modules 26 within the battery pack 24. Battery modules 26 are shown in FIG. 1B. There are two battery modules 26 in battery pack 24 shown in FIG. 1B. Alternatively, battery pack 24 can have any number N of battery modules 26, wherein N is a positive, non-zero integer. Battery modules 26 are electrically connected to one another in parallel. Connecting battery modules 26 in parallel increases the capacity of battery pack 24. Alternatively or additionally, battery modules 26 can be electrically connected to one another in series to increase the voltage output of battery pack 24.

Battery modules 26 contain multiple battery cells 27. Battery cells 27 can have a variety of shapes including cylindrical, prismatic, and pouch. Battery cells 27 in battery modules 26 are connected in series. Connecting the battery cells in series increases voltage output of battery modules 26. Alternatively or additionally, battery cells 27 can be connected in parallel to increase the capacity of battery modules 26.

For example, in some embodiments, battery pack 24 may have a series-parallel arrangement. In this embodiment, battery modules 26 contain individual battery cells 27 placed in series. The series arrangement of battery cells 27 within battery modules 26 increases the voltage output of battery modules 26. Battery modules 26 are then placed in parallel with each other. The parallel arrangement of battery modules 26 increases the current capacity of battery pack 24.

Battery packs 24 are connected to a battery management system and a cooling system, which include electrical connections 28, inlet line 30, and outlet line 32. Inlet line 30 and outlet line 32 are lines that can fluidly connect different components, for example, rubber hosing, steel pipe, and steel hosing. Electricity is removed from battery pack 24 by electrical connections 28. Electricity is used to power vehicle 22 and other electrical systems in vehicle 22. Electricity generated by vehicle 22 can be input into battery pack 24 using electrical connections 28 for storage. Electrical connections 28 can also be used to charge battery packs 24 from an external electricity source. Inlet line 30 and outlet line 32 are used to cool battery packs 24 using the cooling system.

A failure of a single cell 27 within battery pack 24 can lead to a fire event that is difficult to detect and suppress. Fire events include battery cell failure, thermal runways (uncontrolled heating of battery cells 27 within battery module 26), flames inside battery modules 26 or battery pack 24, and combinations thereof. A fire event may be caused by a rupture of the battery cells 27 within battery modules 26. Such a rupture may be caused by physical damage to battery cells 27, operation outside the desired temperature range of battery cells 27, overcharging, undercharging, excessive current draw, internal shorting, external shorting, or any other failure condition. Rupture causes liquid electrolyte to break and produce decomposition byproducts to leak from battery cells 27 into the battery modules and/or battery pack 24. Example decomposition byproducts include hydrogen gas and carbon monoxide. Other example electrolytes include carbon dioxide, ethane, propylene, propane, ethylene, acetylene, and hydrogen fluoride. The type and quantity of gaseous byproducts depends on the level of battery cell breakdown (how close the cell is to rupture) and the type of chemical electrolyte in the battery cell. Infrared radiation can also be released in battery packs 24 during a fire event.

A fire suppression system includes a gas detection system with detectors in battery packs 24 that sense the leaked gaseous electrolyte byproducts, decomposition byproducts and/or infrared radiation. The gas detection system (including the detectors) triggers a controller of the fire suppression system to release a fire suppressant into battery packs 24 and dispatch an alarm to the vehicle operator. The fire suppressant enters battery packs 24 through a second inlet line dedicated to delivering an emergency fire suppressant. The emergency fire suppressant circulates inside battery packs 24 to cool the battery cells 27 in battery modules 26. The emergency fire suppressant then exits through a second outlet line dedicated to the fire suppression system. The fire suppression system is described in more detail below.

Fire Suppression System 100

Figure 2:
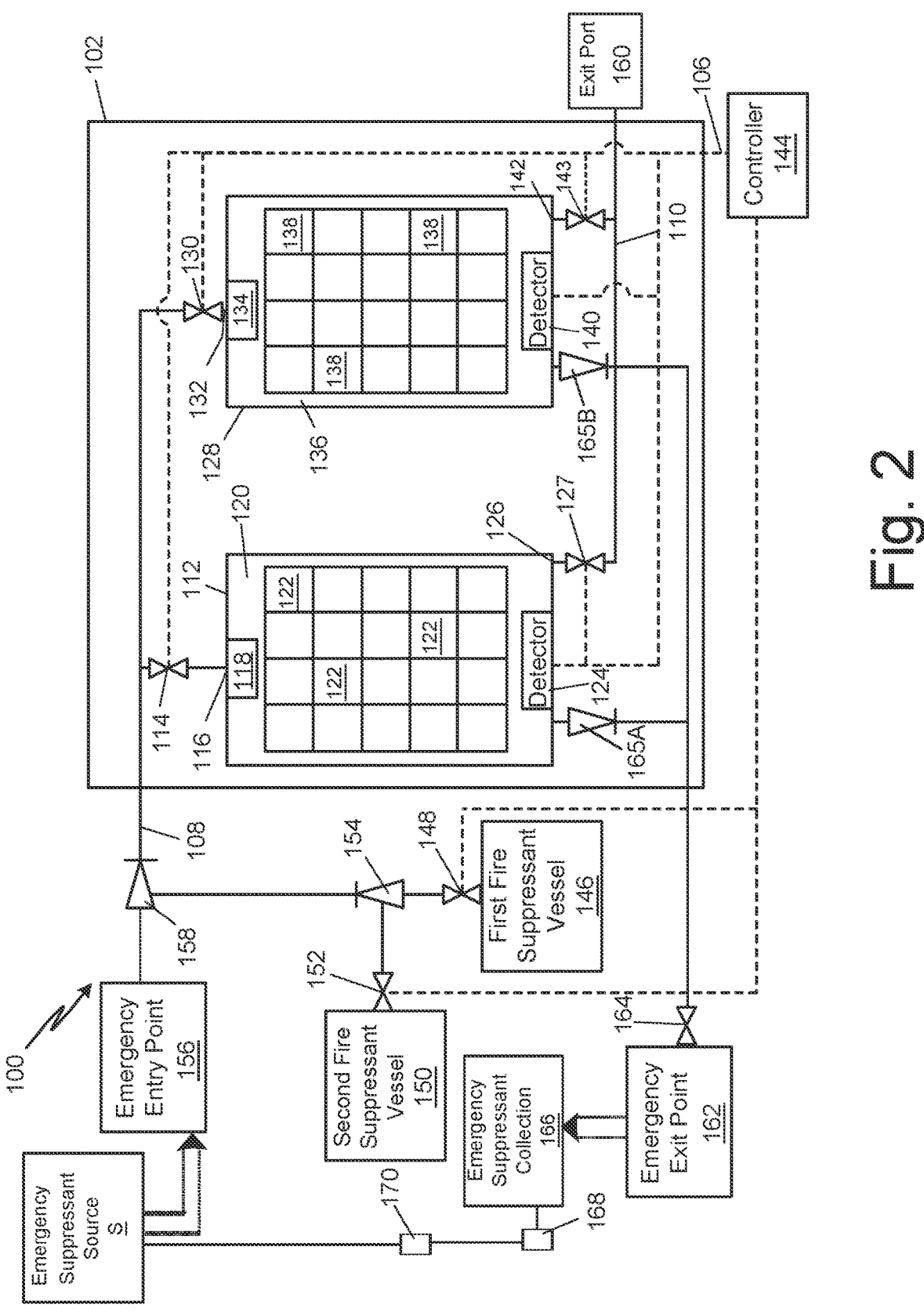
FIG. 2 is a schematic of a fire suppression system for a Li-ion battery pack.

FIG. 2 is a schematic of fire suppression system 100. Fire suppression system 100 is for battery storage area 102. Fire suppression system 100 includes electrical connections 106, inlet line 108, and outlet line 110. Within battery storage area 102 is first battery pack 112, which includes first inlet valve 114, first inlet 116, first nozzle 118, first internal volume 120, first battery modules 122, first detector 124, first outlet 126, and first outlet valve 127. Battery storage area 102 also includes second battery pack 128 with second inlet valve 130, second inlet 132, second nozzle 134, second internal volume 136, second battery modules 138, second detector 140, second outlet 142, and second outlet valve 143. Fire suppression system 100 also includes controller 144, first fire suppressant vessel 146 with first vessel valve 148, second fire suppressant vessel 150 with second vessel valve 152, check valve 154, emergency entry point 156, shuttle check valve 158, and exit port 160. System 100 can also include emergency exit point 162, emergency exit point valve 164, first emergency check valve 165A, second emergency check valve 165B, emergency suppressant collection 166, pump 168, and filter 170. FIG. 2 also includes emergency suppressant source S.

Battery storage area 102 is in a vehicle, specifically an aircraft. Fire suppression system 100 includes electrical connections 106, inlet line 108, and outlet line 110 connected to first battery pack 112 and second battery pack 128. Electrical connections 106, inlet line 108, and outlet line 110 are connections for fire suppression system 100 and are in addition to line and electrical connections that are part of standard battery pack architecture for a battery management system and a cooling system (for example, electrical connections 28, inlet line 30, and outlet line 32, as described in relation to and shown in FIGS. 1A-1B). Signaling to controller 144 from first battery pack 112 and second battery pack 128 occurs through electrical connections 106. Electrical connections 106 are also used for controlling components of first battery pack 112 and second battery pack 128. Inlet line 108 and outlet line 110 are made of materials that can fluidly connect elements, for example, rubber hosing, steel tubing, and steel pipe. Inlet line 108 delivers emergency fire suppressant to first battery pack 112 and second battery pack 128. Outlet line 110 removes emergency fire suppressant from first battery pack 112 and second battery pack 128. Outlet line 110 connects to exit port 160, which can be a vent for spent emergency fire suppressant. Exit port 160 is through an outer surface of a vehicle with fire suppression system 100 installed and releases spent fire suppressant from battery storage area. Exit port 160 allows for spent fire suppressant to be vented into an environment surrounding the vehicle.

First battery pack 112 and second battery pack 128 are connected in parallel and/or series to increase electrical current capacity and/or voltage output from first battery pack 112 and second battery pack 128 collectively. While battery storage area 102 includes two battery packs 112 and 128, other embodiments of battery storage area 102 can have any non-zero integer number N of battery packs.

First battery pack 112 includes first inlet valve 114, first inlet 116, first nozzle 118, first internal volume 120, first battery modules 122, first detector 124, and first outlet 126. First battery pack 112 fluidly connects to inlet line 108 of fire suppression system 100. First inlet valve 114 controls fluid movement through first inlet 116. First inlet valve 114 is electrically connected to electrical connections 106 of fire suppression system 100. First inlet 116 is adjacent to first nozzle 118, which directs fluid entering first battery pack 112 around first internal volume 120. Multiple first battery modules 122 are within and partially surrounded by first internal volume 120 (or intrapack space 120). First battery modules 122 are connected to one another in series and/or parallel to increase the voltage and/or power output of first battery pack 112, respectively. First battery pack 112 may include any positive, non-zero integer N number of first battery modules 112. Each first battery module 122 houses multiple battery cells (for example, battery cells 27 in FIG. 1B). The battery cells are connected in series and/or parallel to reach a desired voltage and/or power output, respectively, as discussed in relation to FIGS. 1A-1B.

First detector 124 senses conditions of first battery pack 112 including concentrations of leaked gaseous electrolyte decomposition byproducts, and/or infrared radiation in first internal volume 120. First detector 124 is electrically connected to electrical connections 106 of fire suppression system 100. In FIG. 2, first detector 124 is in a single sensor housing located inside of first battery pack 112. In alternate embodiments, first detector 124 can have multiple sensors in a single housing, multiple sensors in multiple housings and/or be located outside of first battery pack 112, as will be discussed in relation to FIGS. 4-11. First outlet 126 is in an opposite side of first battery pack 112 from first inlet 116. First outlet 126 connects to outlet line 110 of fire suppression system 100 and drains first battery pack 112. First outlet 126 is controlled by first outlet valve 127. First outlet valve 127 is electrically connected to electrical connections 106. First inlet valve 114 and first outlet valve 127 allow emergency fire suppressant to flow through first battery pack 112 when both valves are open.

Second battery pack 128 includes second inlet valve 130, second inlet 132, second nozzle 134, second internal volume 136, second battery modules 138, second detector 140, second outlet 142, and second outlet valve 143. Second inlet valve 130 controls fluid movement through second inlet 132. Second inlet valve 130 is electrically connected to electrical connections 106. Second inlet 132 fluidly connects second battery pack 128 to inlet line 108 of fire suppression system 100. Second inlet 132 is adjacent to second nozzle 134, which directs fluid entering second battery pack 128 around second internal volume 136 (or intrapack space 136). Multiple second battery modules 138 are within and partially surrounded by second internal volume 136. Second battery modules 138 are connected to one another in series and/or parallel to increase the voltage and power output of second battery pack 128, respectively. Second battery pack 128 may include any positive, non-zero integer number N of battery modules 138. Each second battery module 138 houses multiple battery cells (for example, battery cells 27 in FIG. 1B). The battery cells are connected in series and/or parallel to reach a desired voltage and/or power output, respectively, as discussed in relation to FIGS. 1A-1B.

Second detector 140 senses conditions of second battery pack 128 including concentrations of gasses and/or infrared radiation in second internal volume 136. Second detector 140 is electrically connected to electrical connections 106 of fire suppression system 100. In FIG. 2, second detector 140 is in a single sensor housing located inside of second battery pack 128. In alternate embodiments, second detector 140 can have multiple sensors in a single housing, can be multiple sensors in multiple housings and/or can be located outside of second battery pack 128, as will be discussed in relation to FIGS. 4-11. Second outlet 142 is in an opposite side of second battery pack 128 from second inlet 132. Second outlet 142 connects to outlet line 110 of fire suppression system 100 and drains emergency fire suppressant from second battery pack 128. Second outlet 142 is controlled by second outlet valve 143. Second outlet valve 143 is electrically connected to electrical connections 106. Second inlet valve 130 and second outlet valve 143 work together to allow fluid to flow through second battery pack 128. Second inlet valve 130 and second outlet valve 143 allow emergency fire suppressant to flow through second battery pack 128 when both valves (or emergency exit point 162 as a quick connect adapter, as described below) are open.

Controller 144 together with first detector 124 and second detector 140 create a gas detection system. Controller 144 connects to electrical connections 106 of fire suppression system 100. Controller 144 receives signals from first detector 124 and second detector 140 regarding the conditions of first battery pack 112 and the conditions of second battery pack 128. Conditions include presence of gas (for example, decomposition byproducts like hydrogen gas or carbon monoxide) and presence of infrared radiation. Controller 144 evaluates the conditions received from first detector 124 and second detector 140 to determine if a fire event is occurring in either first battery pack 112 or second battery pack 128. Specific discussion of the gas detection system, including determinations of and actions taken by controller 144, will be discussed in relation to FIGS. 4-11.

Controller 144 also electrically connects to a control panel in a vehicle with system 100 to signal an operator regarding fire events and recommended fire suppression measures. Controller 144 electrically connects to and actuates first inlet valve 114, first outlet valve 127, second inlet valve 130, and second outlet valve 143. Controller 144 opens first inlet valve 114 and first outlet valve 127 or second inlet valve 130 and second outlet valve 143 to allow fire suppressant to flow into and through first battery pack 112 or second battery pack, respectively. Controller 144 closes first inlet valve 114 and first outlet valve 127 or second inlet valve 130 and second outlet valve 143 to block fire suppressant from flowing into first battery pack 112 or second battery pack 128, respectively. Details regarding opening and closing first inlet valve 114, first outlet valve 127, second inlet valve 130, and second outlet valve 143 will be discussed in more detail in relation to FIGS. 12-15 below.

Fire suppression system 100 also includes a multiple on-board fire suppressant system including first fire suppressant vessel 146 with first vessel valve 148, second fire suppressant vessel 150 with second vessel valve 152, and check valve 154. First fire suppressant vessel 146 is a pressurized vessel holding a first fire suppressant. First vessel valve 148 keeps first fire suppressant vessel 146 closed and pressurized. First vessel valve 148 is connected electrically to controller 144. When controller 144 determines a first fire event is occurring in first battery pack 112 or second battery pack 128, controller 144 opens first vessel valve 148 to allow the first fire suppressant to flow through an outlet port into first battery pack 112 or second battery pack 128. Second fire suppressant vessel 150 is a pressurized vessel holding a second fire suppressant. Second vessel valve 152 keeps second fire suppressant vessel 150 closed and pressurized. Second vessel valve 152 is connected electronically to controller 144. When controller 144 determines a second fire event is occurring in first battery pack 112 or second battery pack 128, controller 144 opens second vessel valve 152 to allow the second fire suppressant to flow through an outlet port into first battery pack 112 or second battery pack 128. Specific discussion of the multiple on-board fire suppressant system is discussed in relation to FIGS. 14-15. First fire suppressant vessel 146, second fire suppressant vessel 150, and example chemical compositions of the first fire suppressant and the second fire suppressant will be discussed in relation to FIGS. 16-17.

Check valve 154 is a T-shaped valve with an internal mechanism and three openings. A first opening of check valve 154 connects to first fire suppressant vessel 146. A second opening of check valve 154 connects to second fire suppressant vessel 150. A third opening of check valve 154 connects to inlet line 108 via shuttle check valve 158. Check valve 154 has an internal mechanism to block either the first opening or the second opening as necessary. For example, when the first fire suppressant is released for first fire suppressant vessel 146, the internal mechanism moves to block the second opening so that the first fire suppressant flows toward inlet line 108. In another example, the internal mechanism in check valve 154 moves to block the first opening when the second fire suppressant is released from second fire suppressant vessel 150 so that the second fire suppressant flows toward inlet line 108 of battery storage area 102 and not into empty first fire suppressant vessel 146. The internal mechanism of check valve 154 can be, for example, a ball, a flapper, or any other appropriate mechanism. The multiple on-board fire suppression system will be discussed in more detail in relation to FIGS. 12-13.

System 100 also includes an emergency entry point system with emergency entry point 156, and shuttle check valve 158. Emergency entry point 156 is a connection point mounted outside of battery storage area 102. Emergency entry point 156 is preferably mounted through an outer surface of a vehicle equipped with fire suppression system 100. Emergency entry point 156 can be a quick connect adapter such that a source of emergency fire suppressant can be quickly and easily connected. The quick connect adapter can include an integrated valve that remains closed until a hose or line is attached. Emergency entry point 156 can also be a type of universal connector such that the emergency fire suppressant could be from multiple sources.

Emergency entry point 156 is connected to shuttle check valve 158. Shuttle check valve 158 is a T-shaped valve with three openings. A first opening is connected to emergency entry point 156. A second opening is connected to check valve 154. A third opening is connected to inlet line 108. Shuttle check valve 158 has internal mechanisms that block either the first opening or the second opening. For example, when either the first fire suppressant or the second fire suppressant is flowing into battery storage area 102, internal mechanisms in shuttle check valve 158 block off the first opening so that fire suppressant does not flow towards emergency entry point 156. In another example, when the emergency fire suppressant is being input into battery storage area 102 from emergency entry point 156, the second opening is blocked so that the emergency fire suppressant does not flow toward check valve 154. The internal mechanisms of shuttle check valve 158 can be a ball, a flapper, or any other appropriate mechanisms. The emergency entry point system, including emergency entry point 156 and shuttle check valve 158, will be discussed in more detail in relation to FIGS. 12-13.

System 100 also includes emergency exit point 162, emergency exit point valve 164, first emergency check valve 165A, and second emergency check valve 165B. Emergency exit point 162 is mounted outside of battery storage area 102 and preferably through an outside of the vehicle with system 100 installed. Emergency exit point 162 is preferably mounted on the same side of the vehicle as emergency entry point 156. Emergency exit point 162 fluidly connects to first battery pack 112 and second battery pack 128 at emergency outlets, which are adjacent to first outlet 126 and second outlet 142, respectively. Alternatively, emergency exit point 162 can be integrated with first outlet 126 and second outlet 142 or outlet line 110 of emergency fire suppression system 100. The outlets to first battery pack 112 and second battery pack 128 are controlled by first emergency check valve 165A and second emergency check valve 165B. Valves 165A and 165B are check valves with two openings and an internal mechanism which keeps valves 165A and 165B closed except when the emergency fire suppressant is flowing through first battery pack 112 and/or second battery pack 128. Valves 165A and 165B keep emergency fire suppressant from flowing backwards through the outlets and into first battery pack 112 or second battery pack 128. For example, if emergency fire suppressant is flowing through second battery pack 128, second emergency check valve 165B will open to allow the emergency fire suppressant out of second battery pack 128 and first emergency check valve will remain closed to prevent the emergency fire suppressant from flowing into first battery pack 112 through the outlet to emergency exit point 162.

Emergency exit point 162 is controlled by emergency exit point valve 164. Valve 164 can be opened manually by a user. Valve 164 is also optional when emergency exit point 162 is a quick connect adapter which is opened by connecting a hose or line. Once open, emergency exit point 162 can be configured to drain spent emergency fire suppressant positioned over a drain. When configured as such, spent emergency fire suppressant becomes waste once passing through emergency exit point 162. Emergency exit point 162 is an alternate outlet for the emergency fire suppressant.

Emergency exit point 162 can also be connected to emergency suppressant collection 166 to store or recycle spent emergency suppressant. Emergency suppressant collection 166 is a container for storage, disposal, and/or recycling of spent suppressant once it has drained from first battery pack 112 and/or second battery pack 128. When emergency suppressant collection 166 is used for storage, spent fire suppressant moves through emergency exit point 162 into emergency suppressant collection 166. There, the spent fire suppressant can be safely held until proper cleaning can be carried out. This could include emergency suppressant collection 166 being moved to another location for cleaning. This allows for safe storage and disposal of spent fire suppressant which can contain harmful or hazardous materials. Using emergency suppressant collection 166 as storage reduces negative environmental impacts of fire suppression system 100.

Emergency suppressant collection 166 can also be used to recycle emergency fire suppressant back to emergency suppressant source S. In this embodiment, emergency fire suppression system 100 utilizes pump 168 and filter 170. Pump 168 moves spent fire suppressant from emergency suppressant collection 166 through filter 170 into emergency suppressant source S. Filter 170 removes any particulate matter or unwanted solutes from the spent emergency fire suppressant. From there, the filtered spent emergency fire suppressant can re-enter emergency fire suppression system 100 through emergency entry point 156. At least one heat exchanger can be placed between emergency exit point 162 and emergency suppressant source S to cool emergency fire suppressant that is being recycled. Emergency fire suppressant can continue to cycle through fire suppression system 100, emergency exit point 162, emergency suppressant collection 166, pump 168, and filter 170 until battery storage area 102 is cool enough to approach. This recycling process can continue for hours or days to reach suitable cooling in battery storage area 102. When utilizing emergency suppressant collection 166, the emergency fire suppressant can be grey water.

System 100 allows for early detection of fire events in first battery pack 112 and second battery pack 128 and multiple modes to suppress the fire events. First detector 124 and second detector 140 directly monitor first internal volume 120 and second internal volume 136, respectively, allowing for quick and accurate detection of conditions indicating a fire event. The on-board fire suppression system includes first fire suppressant vessel 146 and second fire suppressant vessel 150, which allow for multiple doses of fire suppressant to respond to a second, latent fire event in first battery pack 112 or second battery pack 128. This additional dose increases opportunities for an operator to either land or pull over a vehicle equipped with fire suppression system 100. Emergency fire suppression system 100 includes emergency entry point 156 to allow an operator to continue to dose first battery pack 112 or second battery pack 128 with coolant in response to a continued fire event or a third, separate fire event. Emergency fire suppression system 100 allows cooling of first battery pack 112 and second battery pack 128 with an emergency suppressant, which can reduce potential heating and fire damage to first battery pack 112, second battery pack 128, or the vehicle.

FIG. 3 is a flow chart showing method 172 for utilizing system 100, shown in FIG. 2. Method 172 includes steps 174-194.

Step 174 includes sensing conditions of first battery pack 112 and second battery pack 128. In step 174, first detector 124 and second detector 140 detect concentrations of gases in first battery pack 112 and second battery pack 128, respectively. Gasses include decomposition byproducts from cells in first battery modules 122 and second battery modules 138, for example, hydrogen gas or carbon monoxide. First detector 124 and second detector 140 can also additionally or alternatively sense presence of infrared radiation in first battery pack 112 and second battery pack 128. Different configurations and functions of first detector 124 and second detector 140 will be discussed in relation to FIGS. 4-11. Step 174 continues throughout method 172.

Step 176 includes transmitting values representing the conditions of first battery pack 112 and second battery pack 128 to controller 144. The transmitted values are alarm outputs to controller 144 from first detector 124 and/or second detector 140 if the conditions in first battery pack 112 and/or second battery pack 128 exceed pre-set calibration limits. For example, if a concentration of hydrogen in first battery pack 112 exceeds a calibrated limit, first detector 124 will transmit an alarm output to controller 144. First detector 124 and second detector 140 have multiple alarm outputs to represent different values of the conditions, as will be described in relation to FIGS. 4-11. Other conditions include the concentration of carbon monoxide gas and the presence of infrared radiation. Values (or alarm outputs) are transmitted through electrical connections 106 of fire suppression system 100. Controller 144 determines if a fire event is occurring in first battery pack 112, second battery pack 128, or both based on the alarm outputs received. Specific discussion regarding transmissions from first detector 124 and second detector 140 to controller 144 will be discussed in relation to FIGS. 4-11. Step 176 continues throughout method 172.

Step 178 includes determining, by controller 144, a first fire event is occurring in battery storage area 102. In step 178, controller 144 compares the alarm outputs transmitted during step 178 to known thresholds of first battery pack 112 and second battery pack 128. Known thresholds include trace levels of decomposition byproducts (hydrogen and carbon monoxide), alarm levels of decomposition byproducts, and/or presence of infrared radiation. FIGS. 4-11 will discuss in detail how controller 144 determines the first fire event is occurring.

Step 180 includes executing, by controller 144, a first fire suppression procedure. Controller 144 will send an alarm output to a vehicle operator regarding implementation of the first fire suppression procedure. This includes a fire alarm warning. Step 180 utilizes a multiple on-board fire suppressant system including first suppression vessel 146 and first vessel valve 148. The first fire suppression procedure includes opening first inlet valve 114 and first outlet valve 127 to first battery pack 112 or second inlet valve 130 and second outlet valve 143 to second battery pack 128, depending on where the first fire event is occurring. The first fire suppression procedure also includes opening first vessel valve 148 to first fire suppressant vessel 146, flowing a first fire suppressant through inlet line 108 of fire suppression system 100, and flowing the first fire suppressant into and through first battery pack 112 or second battery pack 128. The first fire suppressant then cools first battery pack 112 or second battery pack 128. Specific discussion regarding the first fire suppression procedure will occur in relation to FIGS. 14-15.

Step 182 includes determining, by controller 144, a second fire event is occurring in first battery pack 112 or second battery pack 128. Step 182 utilizes first detector 124 and second detector 140 and occurs as step 178 occurs. Controller 144 determines if the second fire event is occurring in first battery pack 112 or second battery pack 128. Specific discussion regarding transmissions from first detector 124 and second detector 140 to controller 144 will be discussed in relation to FIGS. 4-11.

Step 184 includes executing, by controller 144, a second fire suppression procedure. Controller 144 will again send an alarm (for example, a fire warning) to the operator regarding implementation of the second fire suppression procedure. The second fire suppression procedure utilizes the multiple on-board fire suppression system including second fire suppressant vessel 150 and second vessel valve 152. The second fire suppression procedure includes opening (or closing, if the second fire event is occurring in a different battery pack than the first fire event) first inlet valve 114 and first outlet valve 127 to first battery pack 112 or second inlet valve 130 and second outlet valve 143 to second battery pack 128 depending on where the second fire event is occurring. A next step of the second fire suppression procedure is opening second vessel valve 152 to release a second fire suppressant and flowing the second fire suppressant through inlet line 108 of fire suppression system 100. Next, the second fire suppressant cools first battery pack 112 or second battery pack 128. Specific discussion regarding the second fire suppression procedure will occur in relation to FIGS. 14-15.

Step 186 includes determining, by controller 144, a third fire event is occurring in battery storage area 102. Step 186 utilizes first detector 124 and second detector 140 and occurs as steps 178 and 182 occur. Controller 144 determines if the third fire event is occurring in first battery pack 112 or second battery pack 128.

Step 188 includes sending, by controller 144, an alert regarding the third fire event. Controller 144 signals an operator that a third fire event is occurring in battery storage area 102. Specific discussion regarding transmissions from first detector 124 and second detector 140 to controller 144 will be discussed in relation to FIGS. 4-11.

Step 190 includes connecting an emergency fire suppressant source S to battery storage area 102. Steps 188-194 utilize the emergency fire suppression system, including emergency entry point 156 and shuttle check valve 158. The emergency fire suppressant source S connects to emergency entry point 156, which is a quick connect adapter mounted outside of battery storage area 102. Emergency entry point 156 will be discussed in more detail in relation to FIGS. 12-13.

Step 192 includes flowing an emergency fire suppressant through first battery pack 112 or second battery pack 128. The emergency fire suppressant enters system 100 through emergency entry point 156. The emergency fire suppressant flows through shuttle check valve 158 and inlet line 108 into first battery pack 112 or second battery pack 128. The emergency fire suppressant circulates inside first battery pack 112 or second battery pack 128 and removes heat from the battery cells. The emergency fire suppressant also smothers any flames if present. The emergency fire suppressant becomes spent fire suppressant. Spent fire suppressant is heated or decomposed chemical that is not further cooling or smothering flame in first battery pack 112 or second battery pack 128. Flowing the emergency fire suppressant through battery storage area 102 will be discussed in more detail in relation to FGIS. 12-13.

Step 194 includes recycling spent emergency fire suppressant through a container (emergency suppressant collection 166). System 100 can be configured so the spent emergency fire suppressant flows out of emergency exit point 162 into emergency suppressant collection 166. As discussed above, the spent fire suppressant can then be pumped using pump 168 through filter 170 to emergency suppressant source S to be used as emergency fire suppressant again. Step 194 is optional. An alternative to step 194 would be venting or draining the spent emergency fire suppressant as waste through either exit port 160 or emergency exit point 162. Recycling spent emergency fire suppressant through emergency suppressant collection 166 will be discussed in more detail in relation to FGIS. 12-13.

Method 172 allows for directly sensing fire events in a battery pack. Using steps 174 and 176 allows for directly sensing fire events in battery storage area 102. Method 172 allows for releasing multiple doses of fire suppressant into first battery pack 112 or second battery pack 128. Including steps 180 and step 184 allows multiple opportunities to suppress a fire using an on-board fire suppressant. Dosing multiple times allows for an extended time to land or pull over a vehicle with system 100. Method 172 also allows for using an emergency fire suppressant source if a third fire event occurs.

Gas Detection Systems 250 and 350

Figure 4:
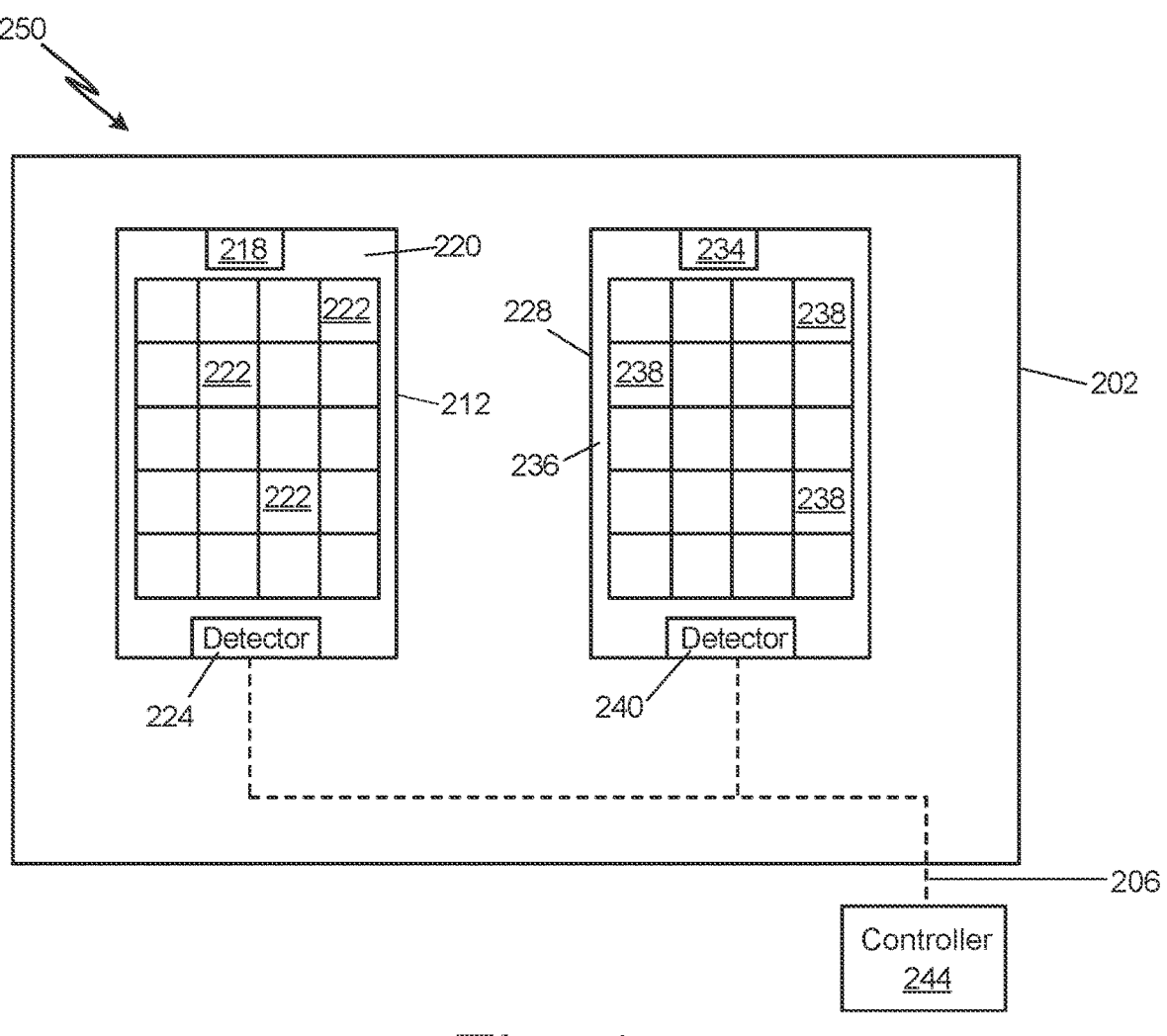
FIG. 4 is a schematic of a first embodiment of a gas detection system for a battery pack.

FIG. 4 is a schematic of gas detection system 250. Gas detection system 250 is an example embodiment of a gas detection contained within fire suppression system 100 of FIG. 2. Gas detection system 250 includes battery storage area 202, electrical connections 206, first battery pack 212, second battery pack 228, and controller 244. First battery pack 212 includes first nozzle 218, first intrapack space 220, first battery modules 222, and first detector 224. Second battery pack 228 includes second nozzle 234, second intrapack space 236, second battery modules 238, and second detector 240.

Battery storage area 202 has the same general structure and design as battery storage area 102 of system 100 shown in FIG. 2. The reference numerals that refer to the parts of battery storage area 202 are incremented by one hundred compared to the reference numerals that refer to the parts of battery storage area 102 of system 100 shown in FIG. 2.

In FIG. 4, first detector 224 is placed directly inside first battery pack 212. In an alternate embodiment, first detector 224 is positioned on a port mounted on first battery pack 212 which provides access to first intrapack space 220. First detector 224 is electrically connected to controller 244 via electrical connections 206 of battery storage area 202.

Similarly, second detector 240 is placed directly inside second battery pack 228 in FIG. 4. In an alternative embodiment, second detector 240 is positioned on a port mounted on second battery pack 228 which provides access to intrapack space 236. Second detector 240 is also electrically connected to controller 244 via electrical connections 206 of battery storage area 202. In alternate embodiments, first detector 224 and/or second detector 240 are wirelessly connected to controller 244.

First detector 224 is configured to sense a concentration value of a first gas and a concentration value of a second gas within first battery pack 212 to determine if a fire event is imminent. A fire event is caused by a rupture of one or more battery cells within first battery modules 222. Such a rupture is caused by physical damage, operation outside the desired temperature range, overcharging, undercharging, excessive current draw, internal shorting, external shorting, or any other failure condition. For example, one or more battery cells within first battery modules 222 may rupture, causing gas to leak into first intrapack space 220. First detector 224 then senses the concentration value of a first gas and senses the concentration value of a second gas present in first battery pack 212. The concentration value of the first gas and the concentration value of the second gas are example conditions of battery pack 212 detected by first detector 224. First detector 224 then compares the concentration value of the first gas and the concentration value of the second gas against one or more threshold concentrations. In some embodiments, first detector 224 is configured with a first threshold and a second threshold. If the concentration value of the first gas and/or the concentration value of the second gas exceed the first threshold, first detector 224 may generate a voltage return level indicative of a low-level (or trace) alarm signal. If the concentration value of the first gas and/or the concentration value of the second gas exceed the second threshold, first detector 224 may generate a voltage return level indicative of a high-level (or significant) alarm. In some embodiments, the comparison of the gas concentration values to the threshold values may be done by controller 244.

First detector 224 then returns a voltage indicative of the alarm level to controller 244. For example, a return voltage from first detector 224 to controller 244 that is 50% of a system operating voltage may indicate normal behavior where no alarm is generated. A return voltage from first detector 224 to controller 244 that is 65% of a system operating voltage may indicate a low-level alarm signal has been generated. A return voltage from first detector 224 to controller 244 that is 75% of a system operating voltage may indicate a high-level alarm signal has been generated. The return voltage levels listed are non-limiting examples and may be adjusted to different percentages as required by the application.

First detector 224 is configured to sense a concentration value of a first gas and a concentration value of a second gas within first battery pack 212. The first gas and the second gas are byproducts of gaseous electrolytes that leak out of first battery modules 222 and can include hydrogen gas and carbon monoxide. In gas detection system 250, the first gas is hydrogen gas ($H_2$), and the second gas is carbon monoxide (CO). In some embodiments, first detector 224 is configured to sense both $H_2$ and CO gas. In other embodiments, first detector 224 may be configured to sense a concentration value of $H_2$ while a separate detector is configured to sense a concentration value of CO. Other gaseous electrolyte byproducts indicative of a fire event or gas leak may be used.

In some embodiments, second detector 240 is also configured to sense a concentration value of a first gas and a concentration value of a second gas within second battery pack 228 to determine if a fire event is imminent. For example, one or more battery cells within one or more second battery module 238 may rupture, causing gas to leak into second intrapack space 236. Second detector 240 then senses the concentration value of a first gas and the concentration value of a second gas present in second battery pack 228. The concentration value of the first gas and the concentration value of the second gas are example conditions of battery pack 212 detected by second detector 240. Second detector 240 then compares the concentration value reading of the first gas and the concentration value reading of the second gas against one or more thresholds concentrations. In some embodiments, second detector 240 is configured with a first threshold and a second threshold. If the concentration value of the first gas and/or the concentration value of the second gas exceed the first threshold, second detector 240 may generate a voltage return level indicative of a low-level (or trace) alarm signal. If the concentration value of the first gas and/or the concentration value of the second gas exceed the second threshold, second detector 240 may generate a voltage return level indicative of a high-level (or significant) alarm. In some embodiments, the comparison of the gas concentration values to the threshold values may be done by controller 244.

Second detector 240 then returns a voltage indicative of the alarm level to controller 244. For example, a return voltage from second detector 240 to controller 244 that is 50% of a system operating voltage may indicate normal behavior where no alarm is generated. A return voltage from second detector 240 to controller 244 that is 65% of a system operating voltage may indicate a low-level alarm signal has been generated. A return voltage from second detector 240 to controller 244 that is 75% of a system operating voltage may indicate a high-level alarm signal has been generated. The return voltage levels listed are non-limiting examples and may be adjusted to different percentages as required by the application.

Second detector 240 is configured to sense a concentration value of a first gas and a concentration value of a second gas within second battery pack 228. The first gas and the second gas are byproducts of gaseous electrolyte byproducts that leak out of second battery modules 238 and can include hydrogen gas and carbon monoxide. In gas detection system 250, the first gas is hydrogen gas ($H_2$), and the second gas is carbon monoxide (CO). In some embodiments, second detector 240 is configured to sense both $H_2$ and CO gas. In other embodiments, second detector 240 may be configured to sense a concentration value of $H_2$ while a separate detector is configured to sense a concentration value of CO. Other gaseous electrolyte byproducts indicative of a fire event or gas leak may be used.

Controller 244 is configured to output various alarm levels based on the voltage return from first detector 224 and second detector 240. Controller 244 is configured to use a two-level alarm system. The first level is a trace alarm. First detector 224 is configured to signal a lower-level trace alarm to controller 244 if the concentration of $H_2$ is between 100 and 150 parts per million (ppm) and/or the concentration of CO is between 400 and 500 ppm in first battery pack 212. Second detector 240 is configured to signal a lower-level trace alarm to controller 244 if the concentration of $H_2$ is between 100 and 150 parts per million (ppm) and/or the concentration of CO is between 400 and 500 ppm in second battery pack 228. The gas concentration levels disclosed are non-limiting examples and may be adjusted to different concentrations as required by factors such as application, battery pack size, or battery cell type. The lower-level trace alarm indicates to an operator that a battery cell (for example, a battery cell within one of first battery modules 222 or a battery cell within one of second battery modules 238) is outgassing. The operator and/or battery management system may then implement a response procedure such as disconnecting an outgassing battery pack or applying additional temperature cooling.

The second alarm of the two-level alarm system is a significant level alarm. Under the significant level alarm condition, first detector 224 is configured to signal a higher-level significant alarm to controller 244 if the concentration of $H_2$ is between 200 and 300 ppm and/or the concentration of CO is between 800 and 1000 ppm in first battery pack 212. Second detector 240 is configured to signal a higher-level significant alarm to controller 244 if the concentration of $H_2$ is between 200 and 300 ppm and/or the concentration of CO is between 800 and 1000 ppm in second battery pack 228. The gas concentration levels disclosed are non-limiting examples and may be adjusted to different concentrations as required by factors such as application, battery pack size, or battery cell type. The significant level alarm may alert an operator to a failing battery cell. In response, controller 244 may implement mitigation methods. In some embodiments, mitigation methods include turning off the battery pack containing an outgassing cell, and/or implementing suppression procedures. Suppression procedures include fire suppression methods discussed in relation to FIGS. 2-3 above and/or FIGS. 12-15 below.

The embodiment depicted in FIG. 4 provides significant advantages. The gaseous levels of $H_2$ and CO detected are calibrated such that battery failure is rapidly detected. Based on such rapid detection, emergency responses can be implemented to prevent battery explosions of a single cell, or battery explosions wherein neighboring cells are also damaged. The two-level alarm system is also calibrated to provide a high level of false alarm immunity. Thus, emergency responses may not be implemented in cases where such emergency responses are not required. The calibrated concentration levels of CO and $H_2$ disclosed for triggering a trace or significant alarm are non-limiting examples. The concentrations may be adjusted as required by factors such as application, battery pack size, or battery cell type.

Figure 5:
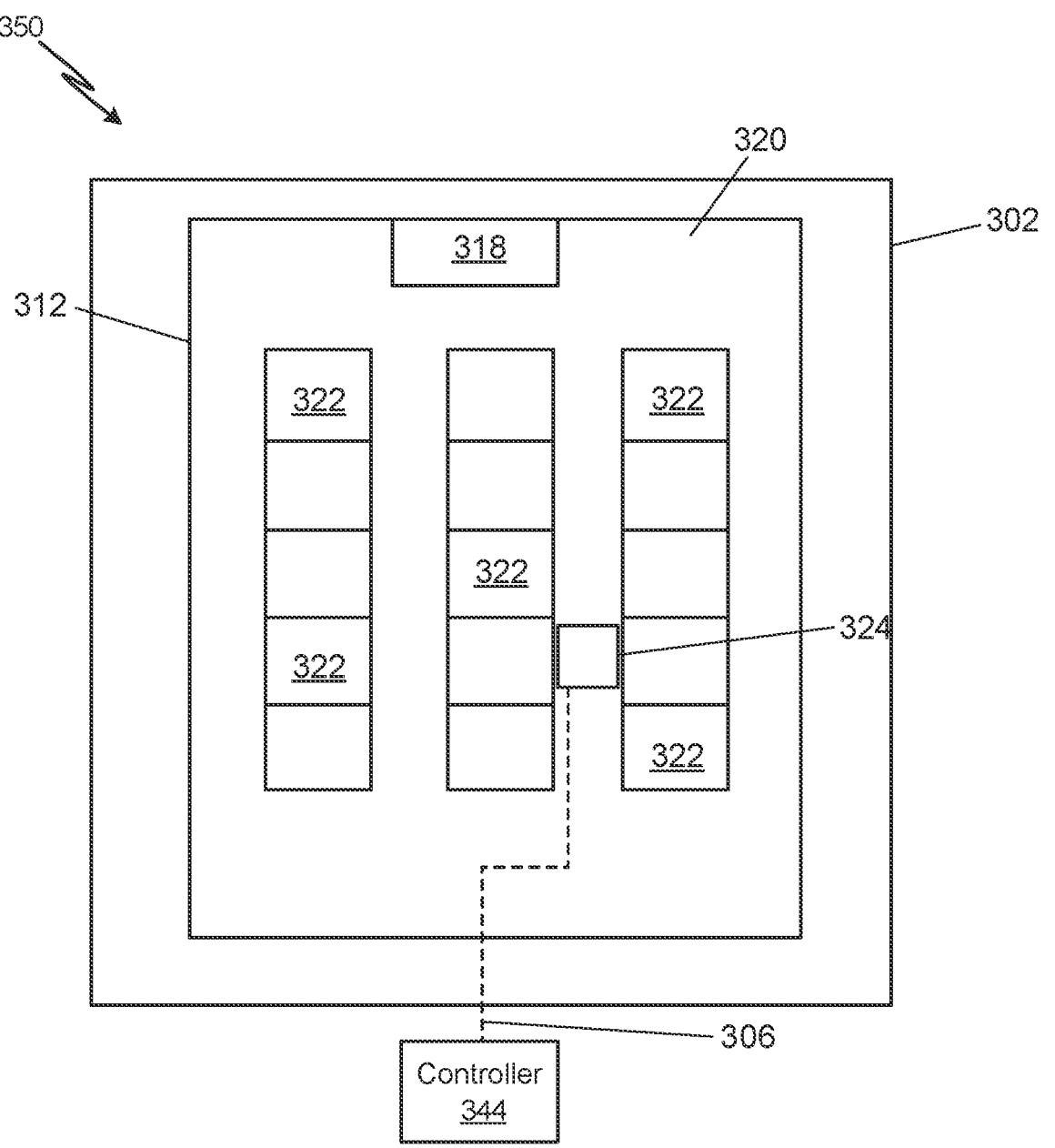
FIG. 5 is a schematic of a second embodiment of a gas detection system within a battery pack.

FIG. 5 is a schematic of an embodiment of gas detection system 350. Gas detection system 350 includes battery storage area 302, electrical connections 306, first battery pack 312, first nozzle 318, first intrapack space 320, first battery modules 322, first detector 324, and controller 344.

Battery storage area 302 has the same general structure and design as battery storage area 102 of system 100 shown in FIG. 2. The reference numerals that refer to the parts of battery storage area 302 are incremented by two hundred compared to the reference numerals that refer to the parts of battery storage area 102 of system 100 shown in FIG. 2.

First battery pack 312 is distinct from first battery pack 112 of battery storage area 102 of FIG. 2 because first battery modules 322 are separate columns surrounded by first intrapack space 320. First battery modules 322 may include any positive, non-zero integer N number of battery cells and first battery pack 312 may include any positive, non-zero integer M number of battery modules 322. Battery cells within first battery modules 322 may be connected in series. The series arrangement of battery cells within first battery modules 322 may increase the overall voltage of first battery pack 312. First detector 324 is mounted within first intrapack space 320 between two columns of first battery modules 322.

First battery pack 312 may contain one or more battery cells within first battery modules 322 that have ruptured. In the case of one or more battery cells having ruptured, gas may leak into intrapack space 320. First detector 324 is configured to sense a concentration value of a first gas and a concentration value of a second gas within first battery pack 312 to determine if a fire event is imminent due to the rupture of one or more battery cells within first battery modules 322.

First detector 324 then compares the concentration value reading of the first gas and the concentration value reading of the second gas against one or more threshold concentrations. In some embodiments, first detector 324 is configured with a first threshold and a second threshold. If the concentration value of the first gas and/or the concentration value of the second gas exceed the first threshold, first detector 324 may generate a voltage return level indicative of a low-level (or trace) alarm signal. If the concentration value of the first gas and/or the concentration value of the second gas exceed the second threshold, first detector 324 may generate a voltage return level indicative of a high-level (or significant)

alarm. First detector 324 then returns a voltage indicative of the alarm level to controller 344.

First detector 324 is configured to sense a concentration value of a first gas and a concentration value of a second gas. In some embodiments, the first gas is hydrogen gas ($H_2$), and the second gas is carbon monoxide (CO). There may also be multiple detectors 324 placed within intrapack space 320. After sensing the concentration value of the first gas and the concentration value of the second gas, first detector 324 generates a voltage return level indicative of a low-level alarm signal or high-level alarm signal. First detector 324 transmits the voltage return level to controller 344. Controller 344 is configured to output various alarm levels based on voltage return level received from first detector 324. In one embodiment, the controller is configured to use a two-level alarm system as disclosed in FIG. 4.

The exemplary embodiments described in FIG. 5 allow for gas detection system 350 to rapidly detect battery failure. Because first detector 324 is mounted within first intrapack space 320, gas detection system 350 may detect gas leakage with a minimal time delay between the leak and the reading by first detector 324. This allows for a rapid response via controller 344 or an operator manually responding to the gas leak event. Further, the calibration levels for sensing gaseous $H_2$ and CO are calibrated, as in FIG. 4, such that there is a high level of false alarm immunity. The calibrated concentration levels of CO and $H_2$ disclosed for triggering a trace or significant alarm are non-limiting examples. The concentrations may be adjusted as required by factors such as application, battery pack size, or battery cell type.

FIG. 6 is a flowchart depicting gas level evaluation method 352, which is a method for evaluating and responding to a concentration value of gas within a battery pack. Method 352 utilizes first detector 224, second detector 240 (shown in FIG. 4), and/or first detector 324 (shown in FIG. 5). Method 352 includes steps 354-362. For the purposes of illustration, reference numerals of FIG. 5 will be used in method 352. Method 352 is not limited to the embodiment of FIG. 5 and may also apply to the embodiment of FIG. 4, or other embodiments defined herein.

At step 354, first detector 324 detects a concentration value of a first gas in first battery pack 312. At step 356, first detector 324 detects a concentration value of a second gas in first battery pack 312. Step 354 and step 356 may occur simultaneously. In some embodiments, the first gas in step 354 is $H_2$ gas and the second gas in step 356 is CO. First detector 324 in method 352 is mounted on a port of battery pack 312 or in intrapack space 320.

At step 358, first detector 324 compares the concentration value of the first gas and the concentration value of the second gas to threshold levels to generate a voltage return value that is indicative of no alarm, a first alarm level, or a second alarm level. In some embodiments, the comparison of the gas concentration values to the threshold values may be done by controller 344. Threshold levels include a low-level alarm threshold for the first gas, a high-level alarm threshold for the first gas, a low-level alarm threshold for the second gas, and a high-level alarm threshold for the second gas.

At step 360, first detector 324 sends the voltage return value to controller 344, wherein the voltage return value indicates to the controller which alarm level should be dispatched.

At step 362, controller 344 dispatches an alarm in response to the concentration of the first gas and the concentration of the second gas. Controller 344 is configured to output the first alarm level if the reading of $H_2$ is between 100 and 150 parts per million and/or the level of CO is between 400 and 500 parts per million. Controller 344 is configured to dispatch the second alarm level if the concentration value of $H_2$ is between 200 and 300 parts per million and/or the concentration value of CO is between 800 and 1000 parts per million. The calibrated concentration levels of CO and $H_2$ disclosed for triggering a trace or significant alarm are non-limiting examples. The concentrations may be adjusted as required by factors such as application, battery pack size, or battery cell type. In response to either the first alarm level or the second alarm level, Controller 344 is configured to turn off a ruptured battery pack that is leaking gas and/or release a cooling agent into the battery pack as described in relation to FIGS. 2-3 above and FIGS. 12-25 below.

Gas and Infrared Detection Systems 450 and 550

Figure 7:
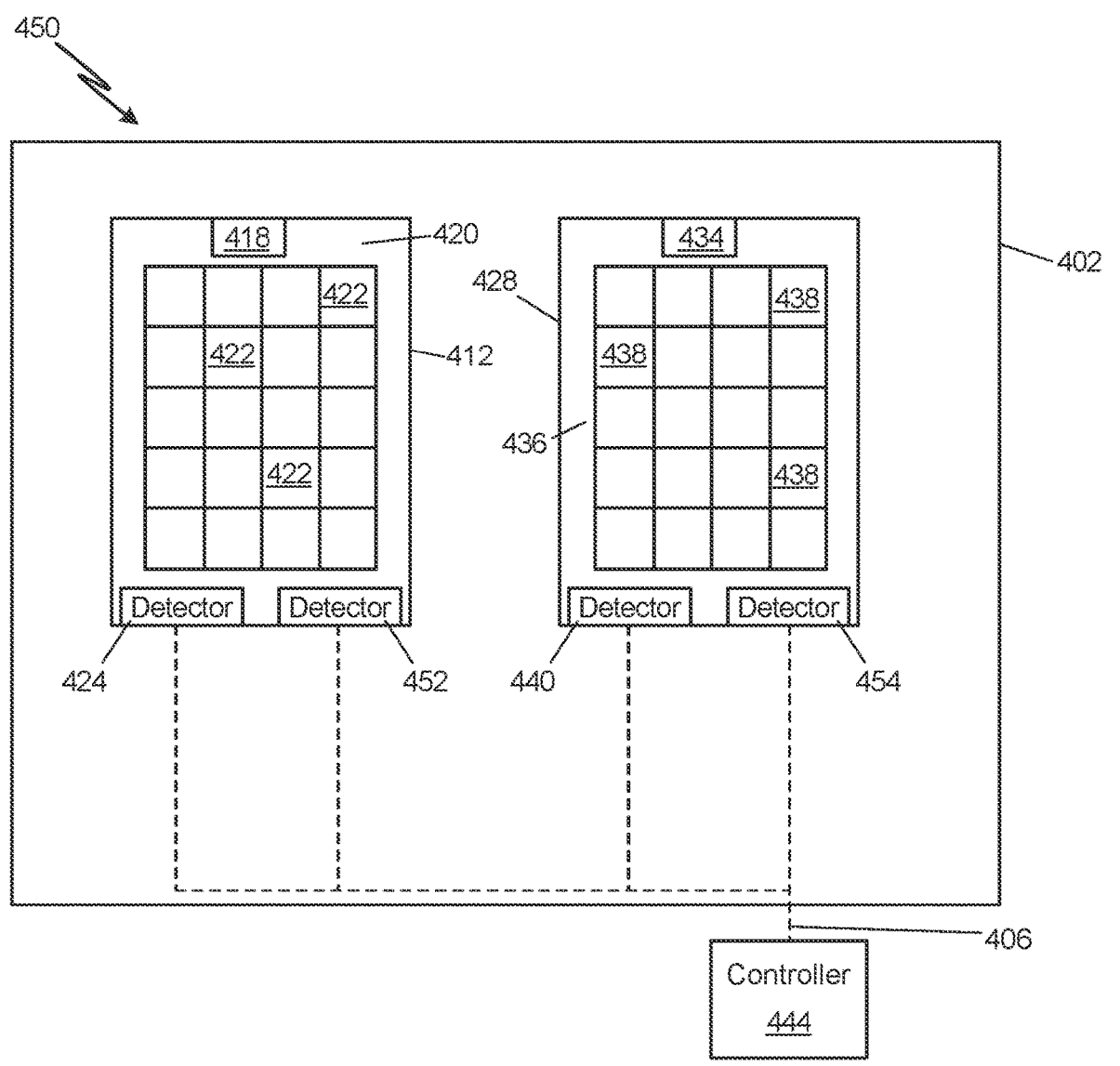
FIG. 7 is a schematic of a first embodiment of a gas and infrared detection system for a battery pack.

FIG. 7 is a schematic of an embodiment of gas and infrared detection system 450. Gas and infrared detection system 450 is contained within fire suppression system 100 of FIG. 2. Gas detection system 450 includes battery storage area 402, electrical connections 406, first battery pack 412, second battery pack 428, and controller 444. First battery pack 412 includes first nozzle 418, first intrapack space 420, first battery modules 422, first detector 424, and third detector 452. Second battery pack 428 includes second nozzle 434, second intrapack space 436, second battery modules 438, second detector 440, and fourth detector 454.

Battery storage area 402 has the same general structure and design as battery storage area 102 of system 100 shown in FIG. 2. The reference numerals that refer to the parts of battery storage area 402 are incremented by three hundred compared to the reference numerals that refer to the parts of battery storage area 102 of system 100 shown in FIG. 2.

First battery pack 412 includes first detector 424 and third detector 452, which are mounted on first battery pack 412. In FIG. 7, first detector 424 and third detector 452 are placed directly inside first battery pack 412. In alternate embodiments, first detector 424 and third detector 452 are positioned on a port mounted on first battery pack 412, which provides access to the interior of first battery pack 412. First detector 424 and third detector 452 are both electrically connected to controller 444 via electrical connections 406. First detector 424 and third detector 452 may alternatively be wirelessly connected to controller 444.

Second battery pack 428 includes second detector 440 and fourth detector 454, which are mounted on second battery pack 428. In FIG. 7, second detector 440 and fourth detector 454 are placed directly inside second battery pack 428. In alternate embodiments, second detector 440 and fourth detector 454 are positioned on a port mounted on second battery pack 428 which provides access to the interior of second battery pack 428. Second detector 440 and fourth detector 454 are both electrically connected to controller 444 via electrical connections 406. Second detector 440 and fourth detector 454 may alternatively be wirelessly connected to controller 444.

First detector 424 is configured to sense a concentration value of a first gas and a concentration value of a second gas within first battery pack 412. Third detector 452 is configured to sense one or more levels of infrared radiation within first battery pack 412. Both first detector 424 and third detector 452 are used to determine if a fire event is imminent. A fire event is caused by a rupture of one or more battery cells within first battery modules 422. Such a rupture is caused by physical damage, operation outside the desired temperature range, overcharging, undercharging, excessive current draw, internal shorting, external shorting, or any other failure condition. For example, one or more battery cells within first battery modules 422 may rupture, causing gas to leak into first intrapack space 420. In addition, battery cells within first battery modules 422 may rupture, causing a fire event and possible subsequent explosion resulting in emission of infrared radiation. First detector 424 may then sense the concentration value of a first gas and the concentration value of a second gas and third detector 452 may measure a level of infrared radiation present in first battery pack 412.

First detector 424 then compares the concentration value of the first gas and the concentration value of the second gas against one or more threshold concentration values, as described above in relation to FIGS. 4-6. Third detector 452 may also evaluate the level of infrared radiation against one or more thresholds. In some embodiments, the comparison of the gas concentration values and the level of infrared radiation to the threshold values may be done by controller 444. First detector 424 generates voltage return levels indicative of no alarm, a low-level, or a high-level alarm as described above in relation to FIGS. 4-6. Third detector 452 generates a voltage return level that indicates no alarm, or an emergency level alarm. First detector 424 and third detector 452 then transmit the voltage return level to controller 444. Controller 444 is configured to dispatch no alarm, a low-level alarm, a high-level alarm, or an emergency level alarm based on the voltage return value received from first detector 424 and third detector 452.

Second detector 440 is configured to a concentration value of a first gas and a concentration value of a second gas within second battery pack 428. Fourth detector 454 is configured to sense one or more levels of infrared radiation within second battery pack 428. Both second detector 440 and fourth detector 454 are used to determine if a fire event is imminent. For example, one or more battery cells within second battery modules 438 may rupture, causing gas to leak into second intrapack space 436. In addition, one or more battery cells within second battery modules 438 may rupture, causing a fire event and possible subsequent explosion. Second detector 440 may then sense the concentration value of a first gas and the concentration value of a second gas and fourth detector 454 may measure a level of infrared radiation present in second battery pack 428.

Second detector 440 then compares the concentration value of the first gas and the concentration value of the second gas against one or more threshold concentration values, as described above in relation to FIGS. 4-6. Fourth detector 454 may also evaluate the level of infrared radiation against one or more thresholds. In some embodiments, the comparison of the gas concentration values and the level of infrared radiation to the threshold values may be done by controller 444. Second detector 440 generates voltage return levels indicative of no alarm, a low-level, or a high-level alarm as described above in relation to FIGS. 4-6. Fourth detector 454 generates a voltage return level that indicates no alarm, or an emergency level alarm. Second detector 440 and fourth detector 454 then transmit the voltage return level to controller 444. Controller 444 is configured to dispatch no alarm, a low-level alarm, a high-level alarm, or an emergency level alarm based on the voltage return value received from second detector 440 and fourth detector 454.

First detector 424 is configured to sense the concentration value of a first gas and the concentration value of a second gas within first battery pack 412. In some embodiments, the first gas is hydrogen gas ($H_2$), and the second gas is carbon monoxide (CO). In some embodiments, first detector 424 is configured to sense a concentration value of both $H_2$ and CO gas. In other embodiments, first detector 424 may be configured to sense a concentration value of $H_2$ while a separate detector is configured to sense a concentration value of CO. Other selected gas byproducts may also be used.

Second detector 440 is configured to sense a concentration value of a first gas and a concentration value of a second gas within second battery pack 428. In some embodiments, the first gas is hydrogen gas ($H_2$), and the second gas is carbon monoxide (CO). In some embodiments, second detector 440 is configured to sense a concentration value of both $H_2$ and CO gas. In other embodiments, second detector 440 may be configured to sense a concentration value of $H_2$ while a separate detector is configured to sense a concentration value of CO or other selected gas byproducts.

Third detector 452 is configured to sense one or more levels of infrared radiation within first battery pack 412. Fourth detector 454 is configured to sense one or more levels of infrared radiation within second battery pack 428. Third detector 452 and fourth detector 454 are configured to sense one or more levels of radiation consistent with a fire event, and are generally immune from triggering false alarms based on other radiation sources including but not limited to sunlight or flashlights.

Controller 444 is configured to dispatch various alarm levels based on the return voltage received from first detector 424, second detector 440, third detector 452, and fourth detector 454. In one embodiment, the controller is configured to use a three-level alarm system. The first level is a lower-level trace alarm. Controller 444 is configured to dispatch a lower-level trace alarm if the concentration value of $H_2$ is between 100 and 150 parts per million (ppm) or the concentration value of CO is between 400 and 500 ppm. The gas concentration levels disclosed are non-limiting examples and may be adjusted to different concentrations as required by factors such as application, battery pack size, or battery cell type. The lower-level trace alarm indicates to an operator that a battery cell (for example, one or more battery cells within first battery modules 422) is outgassing. The operator and/or the battery management system may then implement a response procedure such as disconnecting a battery pack which incorporates an outgassing cell or removing the load/charging.

The second alarm of the three-level alarm system is a significant level alarm. Under the significant level alarm condition, controller 444 is configured to dispatch a significant level alarm if the concentration value of $H_2$ is between 200 and 300 ppm or the concentration value of CO is between 800 and 1000 ppm. The gas concentration levels disclosed are non-limiting examples and may be adjusted to different concentrations as required by factors such as application, battery pack size, or battery cell type. The significant level alarm may alert an operator to a failing battery cell. In response, controller 444 may implement mitigation methods. In some embodiments, mitigation methods include turning off the outgassing cell, turning off the battery pack, and/or discharging suppression (for example system 100 in FIG. 2, system 700 in FIG. 12, and/or system 800 in FIG. 14).

The third alarm of the three-level alarm system is an emergency alarm. Under the emergency level alarm condition, controller 444 is configured to dispatch an emergency level alarm if a threshold level of infrared radiation is detected. In an exemplary embodiment, third detector 452 and/or fourth detector 454 is/are Kidde Optical Flame Detectors. In such an embodiment, third detector 452 and fourth detector 454 both return a voltage indicative of the alarm level to controller 444. For example, if the voltage return from third detector 452 and/or fourth detector 454 is 85% of the system operating voltage, controller 444 may dispatch an emergency alarm condition. The voltage return percentage is merely intended to be an example and may be adjusted to any level. In response to an emergency alarm condition, controller 444 may implement mitigation methods. In some embodiments, mitigation methods include turning off the battery pack containing an outgassing cell, discharging suppression (for example system 100 in FIG. 2, system 700 in FIG. 12, and/or system 800 in FIG. 14), and/or alerting first responders.

Figure 8:
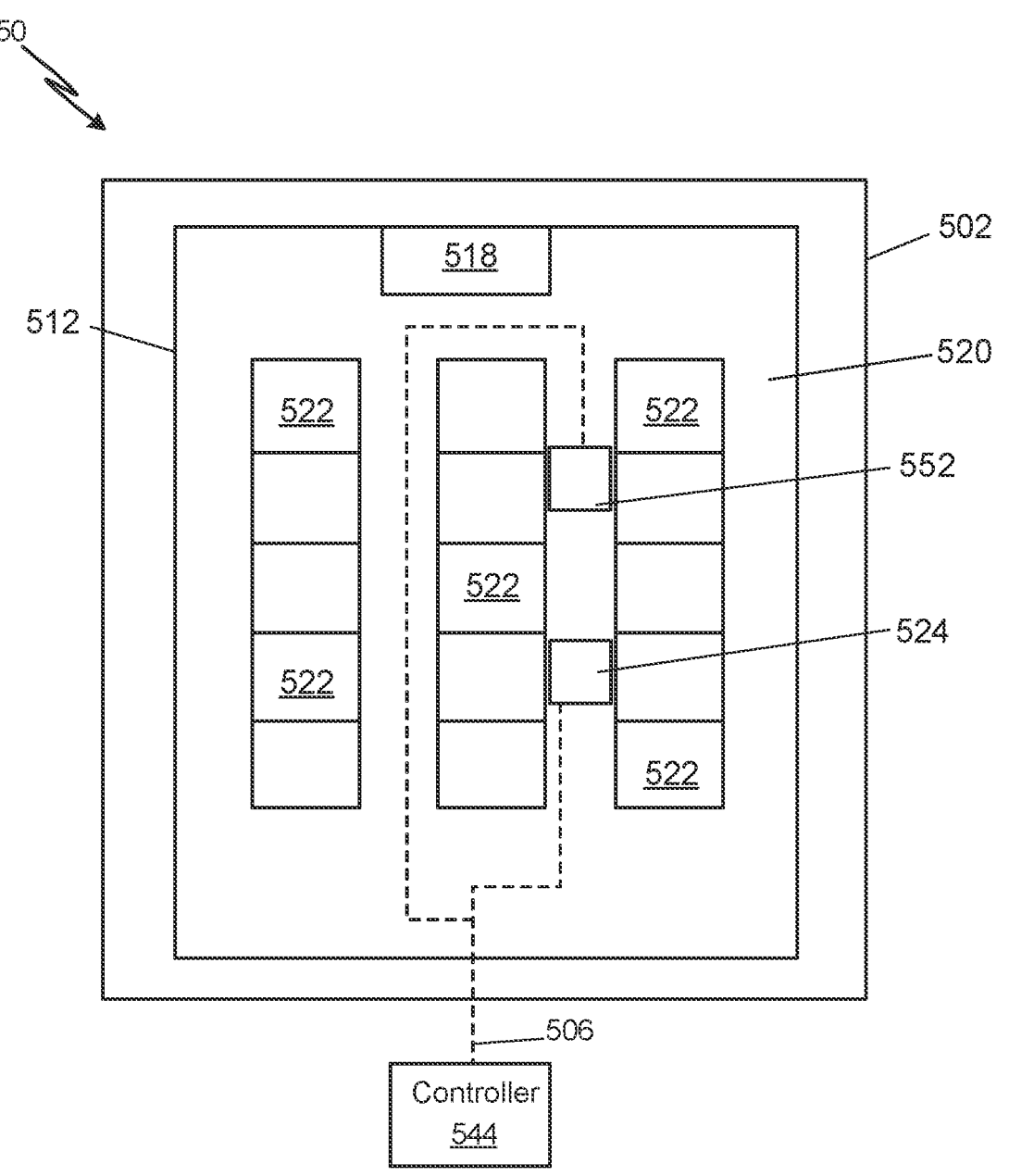
FIG. 8 is a schematic of a second embodiment of a gas and infrared detection system for a battery pack.

FIG. 8 is a schematic of gas and infrared detection system 550. Gas and infrared detection system 550 includes battery storage area 502, electrical connections 506, first battery pack 512 with first nozzle 518, first intrapack space 520, first battery modules 522, first detector 524, third detector 552, and controller 544.

Battery storage area 502 has the same general structure and design as battery storage area 102 of system 100 shown in FIG. 2. The reference numerals that refer to the parts of battery storage area 502 are incremented by four hundred compared to the reference numerals that refer to the parts of battery storage area 102 of system 100 shown in FIG. 2.

First battery pack 512 is distinct from first battery pack 112 of battery storage area 102 of FIG. 2 because first battery modules 522 are separate columns surrounded by first intrapack space 520. First battery modules 522 may include any positive, non-zero integer N number of battery cells and first battery pack 512 may include any positive, non-zero integer M number of first battery modules 522. First battery cells within first battery modules 522 are a plurality of battery cells connected in series. The series arrangement of battery cells may increase the overall voltage of first battery pack 512.

First detector 524 is mounted within intrapack space 520, and between first battery modules 522. First detector 524 is electrically connected to controller 544 via electrical connections 506. Third detector 552 is mounted within intrapack space 520, and between first battery modules 522. Third detector 552 is electrically connected to controller 544 via electrical connections 506. First detector 524 and third detector 552 can alternatively be wirelessly connected to controller 544.

First battery pack 512 may contain one or more battery cells within first battery modules 522 that have ruptured. In the case of one or more battery cells within first battery modules 522 having ruptured, gas may leak into intrapack space 520. Further, ruptured battery cells may lead to a fire event, emitting light and hence infrared radiation. Such infrared radiation is detectable in intrapack space 520.

First detector 524 is configured to sense a concentration value of a first gas and a concentration value of a second gas within first battery pack 512 to determine if a fire event is imminent due to the rupture of one or more battery cells within first battery modules 522. In some embodiments, first battery pack 512 includes two detectors wherein the first detector is configured to sense a concentration value of a first gas and the second detector is configured to sense a concentration value of a second gas.

First detector 524 then compares the concentration value reading of the first gas and the concentration value reading of the second gas against one or more threshold concentration values as described above in relation to FIGS. 4-7. Third detector 552 may also evaluate the level of infrared radiation against one or more thresholds as described above in relation to FIG. 7. In some embodiments, the comparison of the gas concentration values and the level of infrared radiation to the threshold values may be done by controller 544. First detector 524 generates voltage return levels indicative of no alarm, a low-level alarm, or a high-level alarm as described above in relation to FIGS. 4-6. Third detector 552 generates a voltage return level that indicates no alarm, or an emergency level alarm as described above in relation to FIG. 7. First detector 524 and third detector 552 then transmit the voltage return level to controller 544. Controller 544 is configured to dispatch no alarm, a low-level alarm, a high-level alarm, or an emergency level alarm based on the voltage return value received from first detector 524 and third detector 552.

The exemplary embodiments described in FIG. 8 allow for gas and infrared detection system 550 to rapidly detect battery failure to detect if a fire event has occurred. Because first detector 524 and third detector 552 are mounted within first intrapack space 520, gas and infrared detection system 550 may detect gas leakage or a fire event with a minimal time delay between the leak and the reading by first detector 524 and third detector 552. This allows for a rapid response via controller 544 or an operator manually responding to the gas leak event. Further, the calibration levels for sensing gaseous $H_2$ and CO are calibrated, as in FIG. 4, such that there is a high level of false alarm immunity. The calibrated concentration levels of CO and $H_2$ disclosed for triggering a trace or significant alarm are non-limiting examples. The concentration values may be adjusted based on factors such as battery pack size or battery cell type.

FIG. 9 is a flowchart for method 570, which is a method for evaluating and responding to a level of gas and infrared radiation within a battery pack (for example, first battery pack 412 in FIG. 7 and/or first battery pack 512 in FIG. 8). Method 570 can utilize detectors in first battery pack 412 and/or second battery pack 428 of FIG. 7 including first detector 424, second detector 440, third detector 452, and fourth detector 454. Method 570 can also utilize detectors in first battery pack 512 of FIG. 8 including first detector 524 and third detector 552. At step 554, a detector detects a concentration of a first gas in the battery pack. Method 570 includes steps 554-566. For the purposes of illustration, reference numerals of FIG. 8 will be used in method 570. Method 570 is not limited to the embodiment of FIG. 8 and may also apply to the embodiment of FIG. 7, or other embodiments herein.

At step 554, first detector 524 detects a concentration value of $H_2$ gas in the battery pack. At step 556, first detector 524 detects a concentration value of a second gas in the internal battery pack. In some embodiments, the first gas in step 554 is $H_2$ gas and the second gas in step 556 is CO. First detector 524 in method 570 is mounted on a port of first battery pack 512 or in the first intrapack space 520 of battery pack 512.

At step 558, third detector 552 detects a level of infrared radiation in first battery pack 512. In some embodiments, third detector 552 of step 558 is mounted inside battery pack 512 or in first intrapack space 520 of first battery pack 512.

At step 560, first detector 524 compares the concentration value of the first gas and the concentration value of the second gas to threshold levels to generate a voltage return value that is indicative of no alarm, a first alarm level, or a second alarm level. In some embodiments, the comparison of the gas concentration values to the threshold values may be done by controller 544. Threshold levels include a low-level alarm threshold for the first gas, a high-level alarm threshold for the first gas, a low-level alarm threshold for the second gas, and a high-level alarm threshold for the second gas.

At step 562, third detector 552 compares the level of infrared radiation in first battery pack 512 to a threshold level to generate a voltage return value that is indicative of no alarm, or a third alarm level. In some embodiments, the comparison of the level of infrared radiation to the threshold values may be done by controller 544.

At step 564, first detector 524 and third detector 552 transmit the voltage return values to controller 544, wherein the voltage return value indicates to the controller which alarm level should be dispatched.

At step 566, controller 544 dispatches an alarm in response to voltage return values received from first detector 524 and third detector 552. Controller 544 is configured to output the first alarm level if the concentration level of $H_2$ is between 100 and 150 parts per million and/or the concentration level of CO is between 400 and 500 parts per million. Controller 544 is configured to dispatch the second alarm level if the concentration value of $H_2$ is between 200 and 300 parts per million and/or the concentration value of CO is between 800 and 1000 parts per million. The gas concentration levels disclosed are non-limiting examples and may be adjusted to different concentrations as required by factors such as application, battery pack size, or battery cell type. Controller 544 is configured to dispatch the third alarm level if the voltage return value indicates a level of infrared radiation that exceeds a preset threshold value. In response to either the first alarm level, the second alarm level, or the third alarm level, controller 544 is configured to turn off a battery pack containing a ruptured cell that is leaking gas and/or release a cooling agent into the battery pack as described in relation to FIGS. 2-3 above and FIGS. 12-25 below.

Remote Gas Detection System 650

Figure 10:
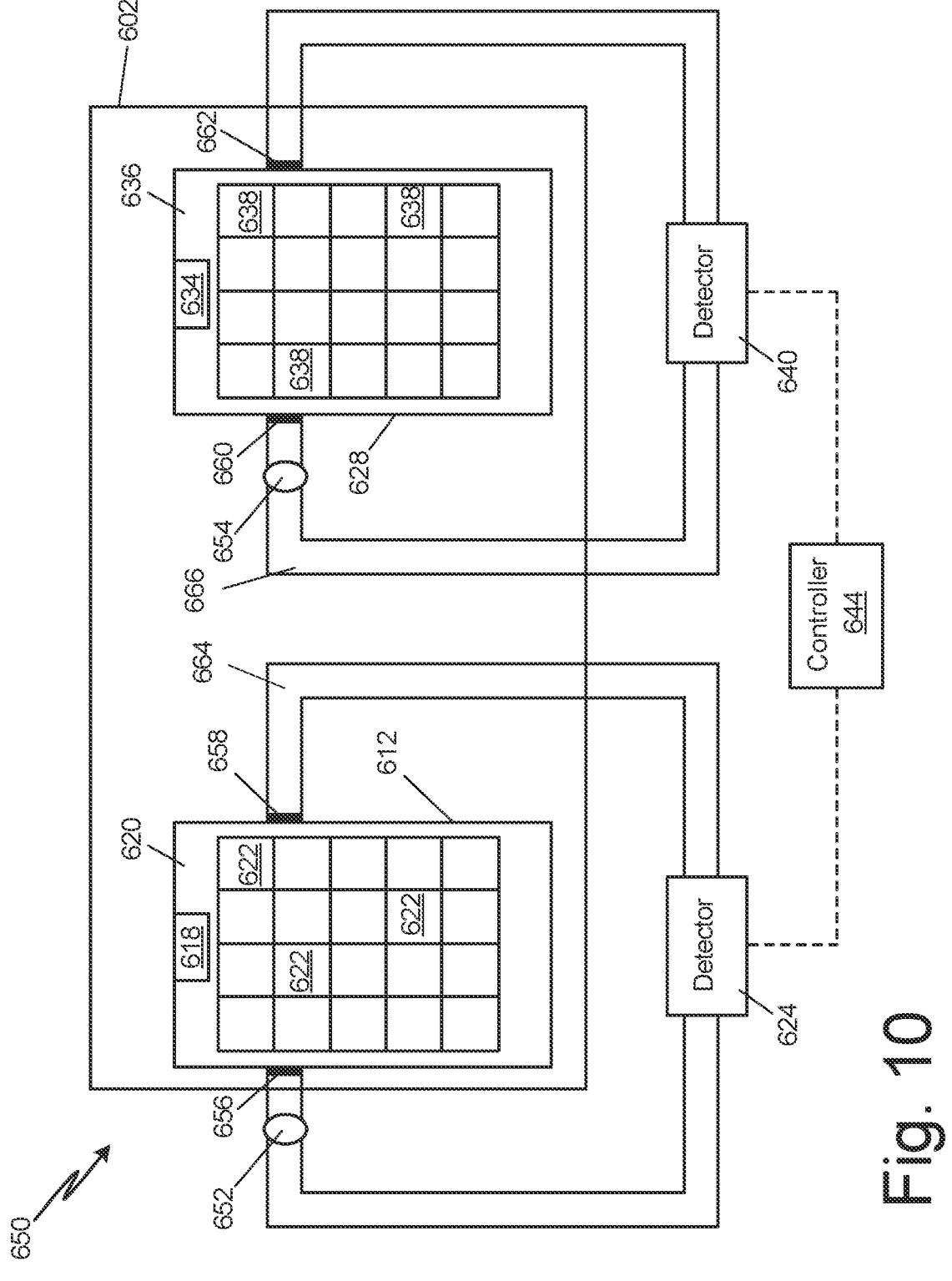
FIG. 10 is a schematic of a first embodiment of a gas detection system for a battery pack.

FIG. 10 is a schematic of an embodiment of gas detection system 650. Gas detection system 650 is contained within fire suppression system 100 of FIG. 2. Gas detection system 650 includes battery storage area 602, first battery pack 612, and second battery pack 628. First battery pack 612 includes first nozzle 618, first intrapack space 620, and first battery modules 622. Second battery pack 628 includes second nozzle 634, second intrapack space 636, and second battery modules 638. System 650 also includes first detector 624 with first fan 652, first sealed gas port 656, and second sealed gas port 658; second detector 640 with second fan 654, third sealed gas port 660, and fourth sealed gas port 662, first tubing 664, second tubing 666 and controller 644.

Battery storage area 602 has the same general structure and design as battery storage area 102 of system 100 shown in FIG. 2. The reference numerals that refer to the parts of battery storage area 602 are incremented by five hundred compared to the reference numerals that refer to the parts of battery storage area 102 of system 100 shown in FIG. 2.

First battery pack 612 differs from first battery pack 112 in that first detector 624 is remotely mounted outside of first battery pack 612. First detector 624 may also be remotely mounted from battery storage area 602. First detector 624 is connected to first battery pack 612 via first tubing 664. Airflow is conducted from first battery pack 612 to first detector 624 using first fan 652. First tubing 664 is connected to first sealed gas port 656 and second sealed gas port 658 such that airflow does not leak outside of first battery pack 612. First detector 624 is electrically connected to controller 644. First detector 624 can also be wirelessly connected to controller 644.

Second detector 640 is also remotely mounted outside of second battery pack 628, which is distinct from first battery pack 612. Second detector 640 may also be remotely mounted from battery storage area 602. Second detector 640 is connected to second battery pack 628 via second tubing 666. Airflow is conducted from second battery pack 628 to second detector 640 using second fan 654. Second tubing 666 is connected to third sealed gas port 660 and fourth sealed gas port 662 such that airflow does not leak outside second battery pack 628. Second detector 640 is electrically connected to controller 644. Second detector 640 can also be wirelessly connected to controller 644.

First detector 624 is configured to sense a concentration value of a first gas and a concentration value of a second gas within the airflow conducted from first battery pack 612 to determine if a fire event is imminent. For example, one or more battery cells within first battery modules 622 may rupture, causing gas to leak into first intrapack space 620. First fan 652 pushes airflow, including the gas that has leaked from one or more battery cells within first battery modules 622, through first sealed gas port 656 to first detector 624 via first tubing 664. First detector 624 then reads the concentration value of a first gas and the concentration value of a second gas present in first battery pack 612. First detector 624 then evaluates the concentration value of the first gas and the concentration value of the second gas against one or more threshold concentration values as described above in relation to FIGS. 4-6. In some embodiments, the comparison of the gas concentration values to the threshold values may be done by controller 644. First detector 624 generates voltage return levels indicative of no alarm, a low-level, or a high-level alarm as described above in relation to FIGS. 4-6. First detector 624 then transmits the voltage return level to controller 644. Controller 644 is configured to dispatch no alarm, a low-level alarm or a high-level alarm based on the voltage return value received from first detector 624.

Second detector 640 is configured to sense a concentration value of a first gas and a concentration value of a second gas within the airflow conducted from second battery pack 628 to determine if a fire event is imminent. For example, battery cells within second battery modules 638 may rupture, causing gas to leak into second intrapack space 636. Second fan 654 pushes airflow, including the gas that has leaked from battery cells within second battery modules 638, through third sealed gas port 660 and to second detector 640 via second tubing 666. Second detector 640 then reads the concentration value of a first gas and the concentration value of a second gas present in second battery pack 628. Second detector 640 then evaluates the concentration value of the first gas and the concentration value of the second gas against one or more threshold concentration values as described above in relation to FIGS. 4-6. In some embodiments, the comparison of the gas concentration values to the threshold values may be done by controller 644. Second detector 640 generates voltage return levels indicative of no alarm, a low-level, or a high-level alarm as described above in relation to FIGS. 4-6. Second detector 640 then transmits the voltage return level to controller 644. Controller 644 is configured to dispatch no alarm, a low-level alarm or a high-level alarm based on the voltage return value received from second detector 640.

First detector 624 is configured to sense a concentration value of a first gas and a concentration value of a second gas within the airflow conducted from first battery pack 612. In some embodiments, the first gas is hydrogen gas ($H_2$), and the second gas is carbon monoxide (CO). Other gaseous electrolyte byproducts indicative of a fire event or gas leak may be used. In an alternate embodiment, first detector 624 is configured to sense a concentration value of the first gas, and a separate detector is configured to sense a concentration value of the second gas.

Second detector 640 is configured to sense a concentration of a first gas and a concentration of a second gas within the airflow conducted from second battery pack 628. In some embodiments, the first gas is hydrogen gas ($H_2$), and the second gas is carbon monoxide (CO). In an alternate embodiment, second detector 640 is configured to sense a concentration value of the first gas, and a separate detector is configured to sense a concentration value of the second gas.

Controller 644 is configured to output various alarm levels based on the return voltage received from first detector 624 and second detector 640. The controller is configured to use a two-level alarm system. The first level is a trace alarm. Controller 644 is configured to dispatch a lower-level trace alarm if the concentration value of $H_2$ is between 100 and 150 parts per million (ppm) or the concentration value of CO is between 400 and 500 ppm. The lower-level trace alarm indicates to an operator that a battery cell (for example, one of first battery cells 622) is outgassing. The operator and/or the battery management system may then implement response procedures such as disconnecting a battery pack containing an outgassing cell, or applying additional temperature cooling.

The second alarm of the two-level alarm system is a significant level alarm. Under the significant level alarm condition, controller 644 is configured to output a significant level alarm if the concentration value of $H_2$ is between 200 and 300 ppm or the concentration value of CO is between 800 and 1000 ppm. The significant level alarm may alert an operator to a failing battery cell. In response, controller 644 may implement mitigation methods. Mitigation methods include turning off the outgassing cell, turning off the battery pack, and/or initiating suppression (for example, fire suppression methods discussed in FIGS. 2-3 above and/or FIGS. 13-15 below).

The embodiment depicted in FIG. 10 provides significant advantages. The first detector 624 and the second detector 640 are remotely mounted, mitigating the space requirement within first battery module 612 and second battery module 628. The first fan 652 and the second fan 654 conduct airflow in a sealed environment, ensuring an accurate gaseous level reading. The gaseous levels of $H_2$ and CO detected are calibrated such that battery failure is rapidly detected. Based on such rapid detection, emergency responses can be implemented to prevent battery explosions of a single cell, or battery explosions wherein neighboring cells are also damaged. The two-level alarm system is also calibrated to provide a high level of false alarm immunity. Thus, emergency responses may not be implemented in cases where such emergency responses are not required. The calibrated concentration levels of CO and $H_2$ disclosed for triggering a trace or significant alarm are non-limiting examples. The concentration values may be adjusted based on factors such as battery pack size or battery cell type.

FIG. 11 is a flowchart showing method 670, which is a method for evaluating and responding to a level of gas within a battery pack. Method 670 includes steps 672-682. Method 670 can utilize first detector 624 (shown in FIG. 10). For the purposes of illustration, the reference numerals used will be those of FIG. 10. Method 670 is not limited to the embodiment of FIG. 10 and may also apply to other embodiments herein.

At step 672, first fan 652 pushes airflow from within first battery pack 612, through first tubing 664 to first detector 624. As airflow is pushed through first tubing 664, gases that are present within first battery pack 612 are also pushed through first tubing 664 and into first detector 624.

At step 674, first detector 624 detects a concentration value of a first gas within first battery pack 612. At step 676, first detector 624 detects a concentration value of a second gas within first battery pack 612. Step 674 and step 676 may occur simultaneously. In some embodiments, the first gas in step 674 is $H_2$ gas and the second gas in step 676 is CO.

At step 678, first detector 624 compares the concentration value of the first gas and the concentration value of the second gas to threshold levels to generate a voltage return value that is indicative of no alarm, a first alarm level, or a second alarm level. Threshold levels include a low-level alarm threshold for the first gas, a high-level alarm threshold for the first gas, a low-level alarm threshold for the second gas, and a high-level alarm threshold for the second gas. In some embodiments, the comparison of the gas concentration values to the threshold values may be done by controller 644.

At step 680, first detector 624 sends the voltage return value to controller 644, wherein the voltage return value indicates to the controller which alarm level should be dispatched.

Finally, at step 682, controller 644 dispatches an alarm in response to the concentration value of the first gas and the concentration value of the second gas. Controller 644 is configured to dispatch the first alarm level if the concentration value of $H_2$ is between 100 and 150 parts per million and/or the concentration value of CO is between 400 and 500 parts per million. Controller 644 is configured to dispatch the second alarm level if the concentration value of $H_2$ is between 200 and 300 parts per million and/or the concentration value of CO is between 800 and 1000 parts per million. In response to either the first alarm level or the second alarm level, controller 644 is configured to initiate insolation of a ruptured cell that is leaking gas, disconnect a battery pack containing a rupture cell, and/or release a cooling agent into the battery pack as described in relation to FIGS. 2-3 above and FIGS. 12-15 below.

Emergency Fire Suppression System 700

Figure 12:
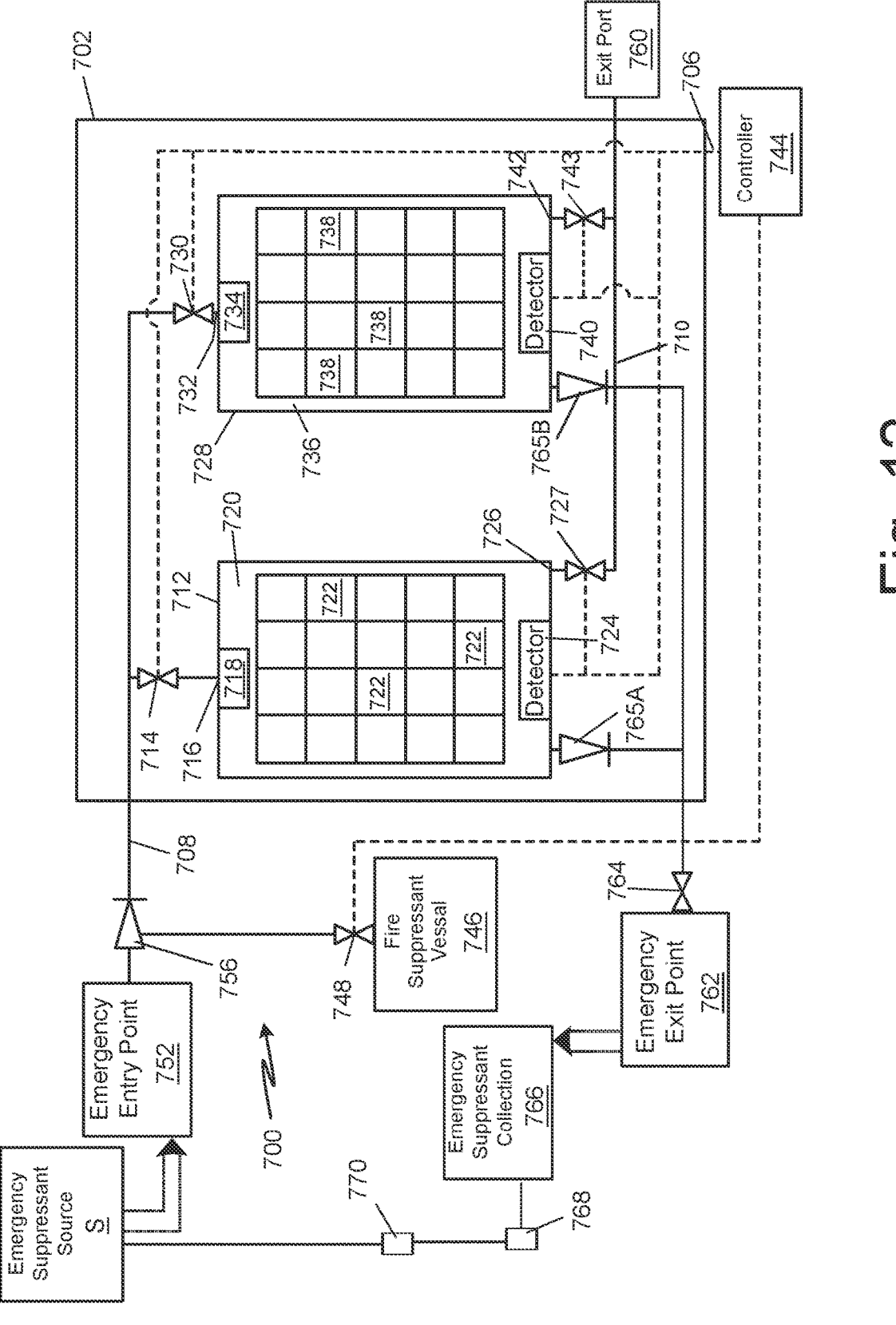
FIG. 12 is a schematic of a first embodiment of a fire suppression system for the Li-ion battery pack including an emergency entry port.

FIG. 12 is a schematic view of fire detection and suppression system 700 for battery storage area 702. System 700 has electrical connections 706, inlet line 708, and outlet line 710. Battery storage area 702 houses first battery pack 712 and second battery pack 728. First battery pack 712 includes first inlet valve 714, first inlet 716, first nozzle 718, first internal volume 720, first battery modules 722, first detector 724, first outlet 726, and first outlet valve 727. Second battery pack 728 includes second inlet valve 730, second inlet 732, second nozzle 734, second internal volume 736, second battery modules 738, second detector 740, second outlet 742, and second outlet valve 743. Fire suppression system 700 includes controller 744, fire suppressant vessel 746 with vessel valve 748, emergency entry point 752, shuttle check valve 756, and exit port 760. System 700 also includes emergency exit point 762, emergency exit point valve 764, first emergency shuttle check valve 765A, second emergency shuttle check valve 765B, emergency suppressant collection 766, pump 768, and filter 770. FIG. 12 also shows emergency suppressant source S.

First battery pack 712 and second battery pack 728 have the same structure and design as first battery pack 112 and second battery pack 128 of system 100 shown in FIG. 1. The reference numerals that refer to the parts of first battery pack 712 and second battery pack 728 are incremented by six hundred compared to the reference numerals that refer to the parts of first battery pack 112 and second battery pack 128 of system 100 shown in FIG. 1.

Controller 744 connects to first inlet valve 714, first detector 724, first outlet valve 727, second inlet valve 730, second detector 740, and second outlet valve 743 via electrical connections 706 of fire suppression system 700. Controller 744 receives transmissions from first detector 724 of first battery pack 712 and second detector 740 of second battery pack 728. Controller 744 also connects to first inlet valve 714 and first outlet valve 727 of first battery pack 712 and second inlet valve 730 and second outlet valve 743 of second battery pack 728. Controller 744 actuates first inlet valve 714, first outlet valve 727, second inlet valve 730, and second outlet valve 743. Controller 744 also connects to vessel valve 748 of fire suppressant vessel 746. Fire suppressant vessel 746 is a pressurized vessel that contains an on-board fire suppressant. The on-board fire suppressant can have a chemical mixture as described in relation to FIGS. 16-17 below.

Fire detection and suppression system 700 has an emergency fire suppression system that includes emergency entry point 752 and shuttle check valve 756. Emergency entry point 752 is mounted outside of battery storage area 702. Emergency entry point 752 is preferably mounted through an exterior surface of a vehicle (for example, vehicle 22 shown in FIG. 1), so emergency entry point 752 is accessible outside of the vehicle. Emergency entry point 752 fluidly connects to shuttle check valve 756. In FIG. 12, a line connects emergency entry point 752 to shuttle check valve 756. Alternatively, emergency entry point 752 directly connects to shuttle check valve 756.

Shuttle check valve 756 is a T-shaped valve with three openings. A first opening connects to emergency entry point 752. A second opening of shuttle check valve 756 connects to fire suppressant vessel 746. A third opening of shuttle check valve 756 connects to inlet line 708 of battery storage area 702. Shuttle check valve 756 includes an internal mechanism to block off the second opening when an emergency suppressant flows through shuttle check valve 756 so that the emergency suppressant does not flow toward fire suppressant vessel 746. The internal mechanism can be, for example, a ball, a flapper, or any other appropriate mechanism.

Fire suppression system 700 detects and suppresses fire events in first battery pack 712 and second battery pack 728. A fire event occurs in first battery pack 712 and/or second battery pack 728 when battery cells (for example, battery cells 27 in FIG. 1B) overheat and/or break, as described above in relation to FIG. 2. First detector 724 and second detector 740 detect conditions that indicate fire events in first battery pack 712 and second battery pack 728, respectively, as described in relation to FIGS. 4-11. Conditions include a concentration of carbon monoxide, a concentration hydrogen gas, and presence of infrared radiation. First detector 724 and second detector 740 transmit values (alarm outputs) representing the conditions to controller 744.

Controller 744 then determines whether the conditions indicate a fire event by comparing transmitted values to stored values, as described in relation to FIGS. 4-11. A first fire event occurs before a second fire event. In the instance of a first fire event, controller 744 opens first inlet valve 714 and first outlet valve 727 or second inlet valve 730 and second outlet valve 743 (depending on if the first fire event is occurring in first battery pack 712 and/or second battery pack 728). Controller 744 also opens fire suppressant vessel valve 748 to release an on-board fire suppressant. The on-board fire suppressant moves through vessel valve 748, shuttle check valve 756, and inlet line 708 of fire suppressant system 700 into and through first battery pack 712 or second battery pack 728, depending on which inlet and outlet valves are open. Spent on-board fire suppressant exits first battery pack 712 or second battery pack 728 through first outlet 726 or second outlet 742, respectively. The spent on-board fire suppressant exits battery storage area 702 through outlet line 710, which connects to a port in the vehicle to vent the spent fire suppressant. Alternatively, spent fire suppressant can vent from first battery pack 712 or second battery pack 728 into battery storage area 702. Spent fire suppressant includes evaporated, decomposed, and/or heated on-board fire suppressant.

For example, first detector 724 could send conditions of first battery pack 712 to controller 744 indicating a fire event. In response, controller 744 opens fire suppressant valve 748, first inlet valve 714, and first outlet valve 727, allowing the on-board fire suppressant to flow out of fire suppressant vessel 746, through shuttle check valve 756, inlet line 708, and inlet valve 714 into first battery pack 712 to cool first battery modules 722 and the battery cells within. Spent on-board fire suppressant then exits first battery pack 712 through outlet 726 and exits battery storage area 702 through outlet line 708.

First detector 724 and second detector 740 continue sensing conditions of first battery pack 712 and second battery pack 728 after the on-board fire suppressant has been released. Controller 744 will receive the conditions, determine if a second fire event in first battery pack 712 or second battery pack 728 is occurring, and alert a vehicle operator to the second fire event. The second fire event could be a continuation of the first fire event in that it is occurring to the same battery cell or within the same module as the first fire event. Sensing and determining by controller 744 occurs as described in relation to FIGS. 4-11 above.

A source of emergency fire suppressant can then be found and attached to emergency entry point 752. Emergency entry point 752 can be a quick connect adapter to a universal nozzle to allow quick connection to the emergency fire suppressant source. The quick connect adapter can include an integrated valve which only opens when a hose or line is attached. Examples of emergency fire suppressant are compressed, liquid carbon dioxide and water. Controller 744 opens first inlet valve 714 and first outlet valve 727 or second inlet valve 730 and second outlet valve 743 based on determinations by controller 744 and/or operator input to allow emergency fire suppressant to flow through first battery pack 712 or second battery pack 728, respectively. The emergency fire suppressant flows through emergency entry point 752, shuttle check valve 756, and inlet line 708 into first battery pack 712 or second battery pack 728. Spent emergency fire suppressant flows out of first outlet 726 or second outlet 742 to outlet line 710 of battery storage area 702. Spent fire suppressant includes, for example, evaporated, heated and/or decomposed fire suppressant.

System 700 also includes emergency exit point 762 and emergency exit point valve 764. Emergency exit point 762 is mounted outside of battery storage area 702 and preferably through an outside of the vehicle with system 700 installed. Emergency exit point 762 is preferably mounted on the same side of the vehicle as emergency entry point 752. Emergency exit point 762 fluidly connects to first battery pack 712 and second battery pack 728 at outlets adjacent to first outlet 726 and second outlet 742. Alternatively, emergency exit point 762 can be integrated with first outlet 726 and second outlet 742 or outlet line 710 of emergency fire suppression system 700. The outlets to first battery pack 712 and second battery pack 728 are controlled by first emergency check valve 765A and second emergency check valve 765B. Valves 765A and 765B are check valves with two openings and an internal mechanism which keeps valves 765A and 765B closed except when the emergency fire suppressant is flowing through first battery pack 712 and/or second battery pack 728. Valves 765A and 765B keep emergency fire suppressant from flowing backwards through the outlets and into first battery pack 712 or second battery pack 728. For example, if emergency fire suppressant is flowing through second battery pack 728, second emergency check valve 765B will open to allow the emergency fire suppressant out of second battery pack 728 and first emergency check valve will remain closed to prevent the emergency fire suppressant from flowing into first battery pack 712 through the outlet to emergency exit point 762.

Emergency exit point 762 is controlled by emergency exit point valve 764. Valve 764 can be opened manually by a user. Valve 764 is also optional when emergency exit point 762 is a quick connect adapter which is opened by connecting a hose or line. Once open, emergency exit point 762 can be configured to drain spent emergency fire suppressant positioned over a drain. When configured as such, spent emergency fire suppressant becomes waste once passing through emergency exit point 762. Emergency exit point 762 is an alternate outlet for the emergency fire suppressant.

Emergency exit point 762 can also be connected to emergency suppressant collection 766 to store or recycle spent emergency suppressant. Emergency suppressant collection 766 is a container for storage, disposal, and/or recycling of spent suppressant once it has drained from first battery pack 712 and/or second battery pack 728. When emergency suppressant collection 766 is used for storage, spent fire suppressant moves through emergency exit point 762 into emergency suppressant collection 766. There, the spent fire suppressant can be safely held until proper cleaning can be carried out. This could include emergency suppressant collection 766 being moved to another location for cleaning. This allows for safe storage and disposal of spent fire suppressant which can contain harmful or hazardous materials. Using emergency suppressant collection 766 as storage reduces negative environmental impacts of fire suppression system 700.

Emergency suppressant collection 766 can also be used to recycle emergency fire suppressant back to emergency suppressant source S. In this embodiment, emergency fire suppression system 700 utilizes pump 768 and filter 770. Pump 768 moves spent fire suppressant from emergency suppressant collection 766 through filter 770 into emergency suppressant source S. Filter 770 removes any particulate matter or unwanted solutes from the spent emergency fire suppressant. From there, the filtered spent emergency fire suppressant can re-enter emergency fire suppression system 700 through emergency entry point 756. At least one heat exchanger can be placed between emergency exit point 762 and emergency suppressant source S to cool emergency fire suppressant that is being recycled. Emergency fire suppressant can continue to cycle through fire suppression system 700, emergency exit point 762, emergency suppressant collection 766, pump 768, and filter 770 until battery storage area 702 is cool enough to approach. This recycling process can continue for hours or days to reach suitable cooling in battery storage area 702. When utilizing emergency suppressant collection 766, the emergency fire suppressant can be grey water.

Fire suppression system 700 provides a way to access first battery pack 712 or second battery pack 728 when battery cells are overheating, and a store of an on-board fire suppressant has been exhausted. Compact battery module and battery pack designs increase the difficulty of suppressing a fire event inside first battery pack 712 and second battery pack 728. Emergency entry point 752 is mounted outside of battery storage area 702 and/or a vehicle, allowing easy access to flow an emergency fire suppressant directly into battery storage area 702. Using carbon dioxide in emergency fire suppression system 700 reduces environmental impact of suppressing fire events because carbon dioxide has a low Global Warming Potential (GWP) of about 1. Utilizing carbon dioxide also avoids polluting water, which is typically used to stop fire events in battery cells. Carbon dioxide also reduces damage to first battery pack 712 or second battery pack 728 because carbon dioxide is not corrosive and non-conductive.

FIG. 13 is a flow chart showing method 772 of utilizing the fire suppression system 700 of FIG. 12. Method 772 includes steps 774-788. Reference numerals used in describing FIG. 13 are from system 700 described in relation to FIG. 12.

Step 774 includes detecting a condition indicative of a fire event in first battery pack 712 and second battery pack 728. Step 774 utilizes first detector 724 in first battery pack 712 and second detector 740 in second battery pack 728. Conditions sensed by first detector 724 and second detector 740 include a concentration of carbon monoxide, a concentration of hydrogen (decomposition byproducts), and/or presence of infrared radiation in first battery pack. In step 774, first detector 724 and second detector 740 can have the functions and configurations of detectors discussed in relation to exemplary embodiments in FIGS. 4-11 above. Step 774 continues throughout method 772.

Step 776 includes transmitting values representing the detected conditions of first battery pack 712 and second battery pack 728 to controller 744. First detector 724 and second detector 740 transmit values representing the concentration of carbon monoxide, the concentration of hydrogen, and/or the presence of infrared radiation to controller 744 through electrical connections 706 of fire suppression system 700. Transmission from first detector 724 and second detector 740 to controller 744 occurs as discussed in relation to exemplary embodiments in FIGS. 4-11 above. Step 776 continues throughout method 772.

Step 778 includes determining, by controller 744, a first fire event is occurring in first battery pack 712 or second battery pack 728. Controller 744 compares the values transmitted by first detector 724 and second detector 740 to stored values indicating a fire event. Determination by controller 744 that a fire event is occurring in battery storage area 702 occurs as discussed in relation to exemplary embodiments in FIGS. 4-11 above. Controller 744 can determine which, if any, of first battery pack 712 and second battery pack 728 are experiencing a fire event.

Step 780 includes executing, by controller 744, an on-board fire suppression procedure. The fire suppression procedure is a set of instructions stored on memory in controller 744 and utilizes an on-board fire suppressant stored in fire suppressant vessel 746. The fire suppression procedure includes at least four steps 780A-780D. Fire suppression system 700 can also send an alert regarding initiating the on-board fire suppression procedure. The alert would go to an operator of the vehicle.

Step 780A includes opening first inlet valve 714 and first outlet valve 727 to first battery pack 712 or second inlet valve 730 and second outlet valve 743 to second battery pack 728 by controller 744. Which sets of valves controller

744 opens depends on where the fire event is occurring. For example, if controller 744 determined in step 778 the first fire event is occurring in first battery pack 712, then controller opens first inlet valve 714 and first outlet valve 727. If controller 744 determined in step 778 the first fire event is occurring in second battery pack 728, then controller opens second inlet valve 730 and second outlet valve 743. Opening first inlet valve 714 and first outlet valve 727 opens first battery pack 712 to inlet line of fire suppression system 700. Opening second inlet valve 730 and second outlet valve 743 opens second battery pack 728, respectively, to inlet line 708 of fire suppression system 700.

Step 780B includes releasing an on-board fire suppressant by controller 744. In step 780B, controller 744 opens vessel valve 748 to fire suppressant vessel 746. Opening vessel valve 748 releases the on-board fire suppressant pressurized inside fire suppressant vessel 746.

Step 780C includes flowing the on-board fire suppressant into first battery pack 712 or second battery pack 728. The on-board fire suppressant flows out of fire suppressant vessel 746 through shuttle check valve 756, inlet line 708, and first inlet 716 into first battery pack 712 or second inlet 732 into second battery pack 728. The on-board fire suppressant is distributed through first battery pack 712 and/or second battery pack 728 by first nozzle 718 and/or second nozzle 734, respectively. The on-board fire suppressant flows into first battery pack 712 if first inlet valve 714 and first outlet valve 727 are open. The on-board fire suppressant flows into second battery pack 728 if second inlet valve 730 and second outlet valve 743 are open.

Step 780D includes cooling first battery pack 712 or second battery pack 728 with the on-board fire suppressant. The on-board fire suppressant removes heat from first battery modules 722 or second battery modules 738 in first battery pack 712 or second battery pack 728, respectively. As the on-board fire suppressant heats, it evaporates and becomes spent fire suppressant. Spent fire suppressant drains from first battery pack 712 or second battery pack 728 through first outlet 726 and second outlet 742, respectively. Outlet line 710 drains the spent fire suppressant from fire suppression system 700. Spent fire suppressant vents out of a vehicle with fire suppression system 700 installed.

Step 782 includes determining, by controller 744, a second fire event is occurring in first battery pack 712 or second battery pack 728. Step 782 proceeds as step 778 and controller 744 compares values transmitted from first detector 724 and second detector 740 to stored values that indicate a fire event. Step 782 occurs as discussed in relation to exemplary embodiments of FIGS. 4-11 above.

Step 784 includes executing a second fire suppression procedure by controller 744. The second fire suppression procedure includes at least six steps 784A-784F.

Step 784A includes alerting an operator to the second fire event. In step 784A, controller 744 alerts an operator of the vehicle to the fire event by sending a message or ringing an alarm. Controller 744 can also have multiple alarm levels, including a low-level alarm, a high-level alarm, and/or an emergency alarm, as described in relation to FIGS. 4-11. At step 784A, the operator can determine a course of action, including ignoring the alarm and/or navigating the vehicle to an emergency suppressant source S (for example, landing an aircraft).

Step 784B includes opening first inlet valve 714 to first battery pack 712 or second inlet valve 730 to second battery pack 728 by controller 744 and emergency exit point valve 764. In step 784B, controller 744 opens first inlet valve 714 or second inlet valve 730 depending on where the second fire event is occurring. Controller 744 can also close first inlet valve 714 and first outlet valve 727 or second inlet valve 730 and second outlet valve 743 to block first battery pack 712 or second battery pack 728 as necessary. Emergency exit point valve 764 also needs to be opened to use emergency exit point 762. To open emergency exit point valve 764, a user can turn the valve if it is located outside of the vehicle. Alternatively, valve 764 can be a quick connect adapter that can be opened by connecting a hose. If necessary, first outlet valve 727 or second outlet valve 743 can be opened by controller 744 to use exit port 760.

Step 784C includes connecting emergency fire suppressant source S to emergency entry point 752. Emergency fire suppressant source S is fire suppressant stored outside of the vehicle. The emergency fire suppressant source S can be pressurized tanks located near an emergency landing spot. The emergency fire suppressant source S can also be mobile. The emergency fire suppressant source S connects to emergency entry point 752. The emergency fire suppressant source S includes a mating connector to emergency entry point 752. Connecting the emergency fire suppressant source S to emergency entry point 752 allows the emergency fire suppressant to quickly enter first battery pack 712 or second battery pack 728 from an external source.

Step 784D includes flowing an emergency fire suppressant through first battery pack 712 or second battery pack 728. The emergency fire suppressant flows through emergency entry point 752 into the fire suppression system 700. The emergency fire suppressant flows through shuttle check valve 756, inlet line 708, and first inlet 716 or second inlet 732 into first battery pack 712 or second battery pack 728, respectively. The emergency fire suppressant enters first battery pack 712 or second battery pack 728 depending on if first inlet valve 714 and first outlet valve 727 or second inlet valve 730 and second outlet valve 743, respectively, are open or closed.

Step 784E includes cooling first battery pack 712 or second battery pack 728 with the emergency fire suppressant. The emergency fire suppressant removes heat from overheating battery cells in first battery modules 722 or second battery modules 738. The emergency fire suppressant is preferably a cold fluid; for example, liquid carbon dioxide. The cold fluid also cools any remaining on-board fire suppressant to elongate the effectiveness of the on-board fire suppressant. The emergency fire suppressant evaporates when contacting the overheating first battery modules 722 or second battery modules 738. Evaporated fire suppressant is spent fire suppressant, which drains or vents from first battery pack 712 and/or second battery pack 728. The emergency fire suppressant flows through battery storage area 702 until first battery pack 712 or second battery pack 728 are sufficiently cooled.

Step 784F includes draining spent fire suppressant from first battery pack 712 or second battery pack 728 through emergency exit point 762. Step 784F is used when emergency exit point valve 764 is open. The spent fire suppressant leaves fire suppression system 700 through emergency exit point 762. In one embodiment, the spent emergency fire suppressant is released or vented as waste into the environment surrounding the vehicle. Alternatively, emergency suppressant collection 766 can be attached to emergency exit point 762 to recycle the spent fire suppressant and/or store it for later disposal. Steps 786-788 discuss use of emergency suppressant collection 766.

Step 786 includes recycling spent fire suppressant to emergency entry point 752. Emergency suppressant collection 766 connects to emergency exit point 762 via hosing, lines or other types of connectors. Utilizing pump 768 and filter 770, the spent fire suppressant can be pumped from emergency suppressant collection 766 back to emergency suppressant source S. This allows for the spent fire suppressant to continue to cool first battery pack 712 or second battery pack 728. Step 786 can be repeated continuously until battery storage area 702 is sufficiently cooled. When recycling emergency fire suppressant through emergency suppressant collection 766, grey water can be used as the emergency fire suppressant. Step 786 is optional in method 772.

Step 788 includes collecting spent fire suppressant into fire suppressant collection 766 for storage and safe disposal. When the emergency fire suppressant is finished recycling through fire suppression system 700, emergency suppressant collection 766 can be used for storing the spent emergency fire suppressant. After the spent suppressant is collected, emergency suppressant collection 766 can be moved to a facility to clean and safely dispose of the spent fire suppressant. This allows for safe disposal of the spent fire suppressant. Step 788 can be used without step 786. Grey water can be used as the emergency fire suppressant when step 788 is being utilized. Step 788 is an alternative to venting spent fire suppressant into the environment surrounding the vehicle.

Method 772 provides a way to suppress two fire events occurring in first battery pack 712 and second battery pack 728. Cooling first battery pack 712 or second battery pack 728 while outside of a vehicle is difficult because battery storage area 702 is buried inside the vehicle and difficult to reach in an emergency. Connecting emergency fire suppressant source S to emergency entry point 752 allows for quick dispensation of the emergency fire suppressant directly into first battery pack 712 or second battery pack 728. Quick access and cooling reduce potential fire damage to the vehicle and first battery pack 712 and second battery pack 728.

Multiple on-Board Suppressant System 800

Figure 14:
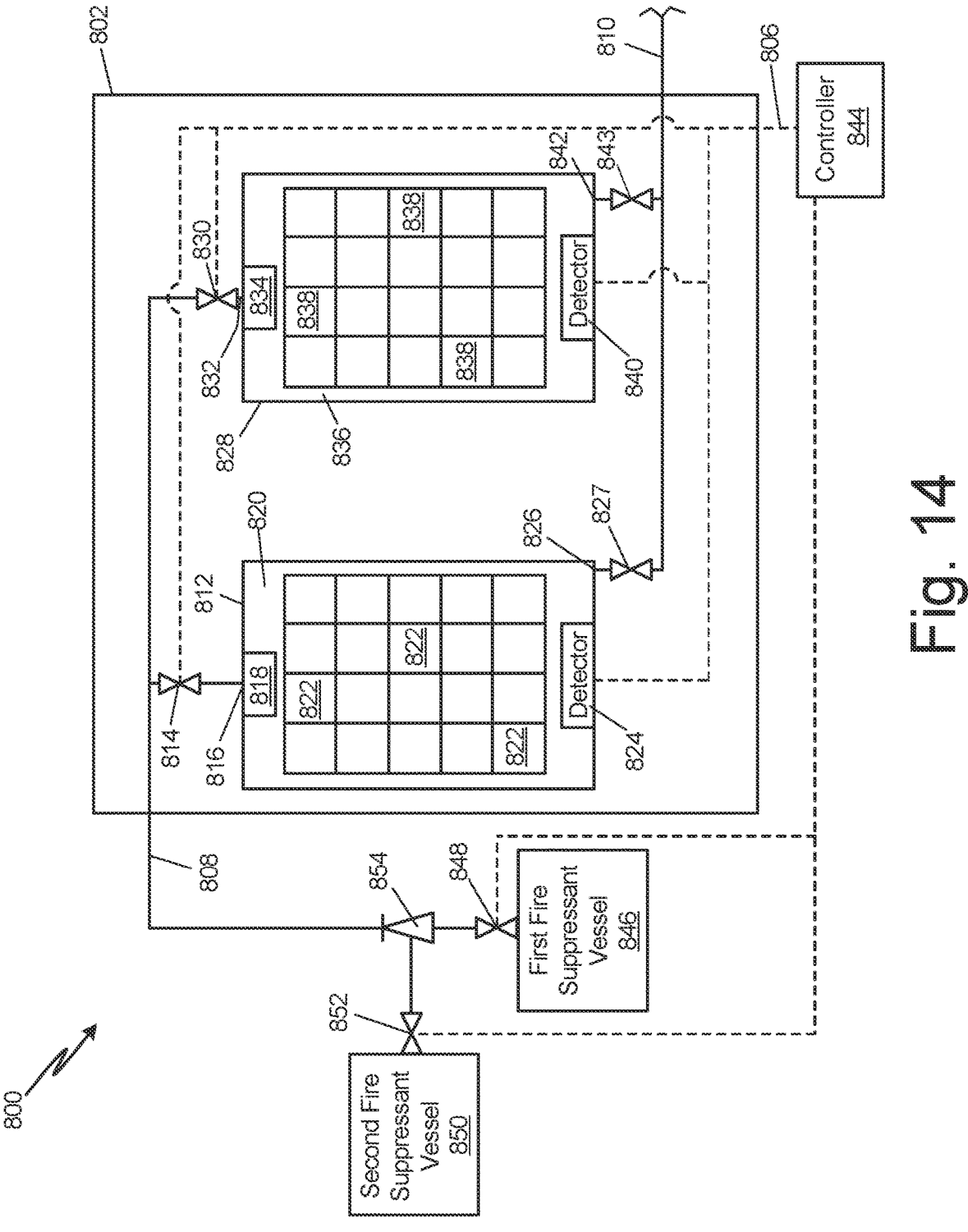
FIG. 14 is a schematic of a second embodiment of a fire suppression system for the Li-ion battery pack including fire suppressants.

FIG. 14 is a schematic of fire suppression system 800 for first battery pack 812 and second battery pack 828 in battery storage area 802. System 800 includes two on-board fire suppressant vessels. Fire suppression system 800 includes electrical connections 806, inlet line 808, and outlet line 810. Battery storage area 802 houses first battery pack 812 and second battery pack 828. First battery pack 812 includes first inlet valve 814, first inlet 816, first nozzle 818, first internal volume 820, first battery modules 822, first detector 824, first outlet 826, and first outlet valve 827. Second battery pack 828 includes second inlet valve 830, second inlet 832, second nozzle 834, second internal volume 836, second battery modules 838, second detector 840, second outlet 842, and second outlet valve 843. Fire suppressant system 800 includes controller 844, first fire suppressant vessel 846 with first vessel valve 848, second fire suppressant vessel 850 with second vessel valve 852, and check valve 854.

First battery pack 812 and second battery pack 828 have the same structure and design as first battery pack 112 and second battery pack 128 of system 100 shown in FIG. 1. The reference numerals that refer to the parts of first battery pack 812 and second battery pack 828 are incremented by seven hundred compared to the reference numerals that refer to the parts of first battery pack 112 and second battery pack 128 of system 100 shown in FIG. 1.

Controller 844 connects to first inlet valve 814, first detector 824, first outlet valve 827, second inlet valve 30, second detector 840, and second outlet valve 843 via electrical connections 806 of fire suppression system 800. Controller 844 also connects to first vessel valve 848 of first fire suppressant vessel 846 and second vessel valve 852 of second fire suppressant vessel 850.

First vessel valve 848 controls an opening to first fire suppressant vessel 846. First vessel valve 848 can be built directly into first fire suppressant vessel 846. First fire suppressant vessel 846 contains a first fire suppressant pressurized inside first fire suppressant vessel 846. Second vessel valve 852 controls an opening to second fire suppressant vessel 850. Second vessel valve 852 can be built directly into second fire suppressant vessel 850. Second fire suppressant vessel 850 contains a second fire suppressant pressurized inside second fire suppressant vessel 850.

Check valve 854 is a T-shaped valve containing with three openings and an internal mechanism. A first opening of check valve 854 connects to first fire suppressant vessel 846. A second opening of check valve 854 connects to second fire suppressant vessel 850. A third opening of check valve 854 connects to inlet line 808 of fire suppression system 800. The internal mechanism of check valve 854 can selectively block the first opening and the second opening. For example, when first fire suppressant vessel 846 is discharged, the internal mechanism blocks the second opening to prevent the first fire suppressant from flowing into second fire suppressant vessel 850. In another example, when second fire suppressant vessel 850 discharges, the internal mechanism blocks the first opening to prevent the second fire suppressant from flowing into first fire suppressant vessel 846. The internal mechanism can be, for example, a ball, a flapper, or any other appropriate mechanism.

Fire suppression system 800 detects fire events within battery storage area first battery pack 812 and second battery pack 828 and dispenses the first fire suppressant and the second fire suppressant in response. First detector 824 and second detector 840 are positioned to detect a fire event in first battery pack 812 and second battery pack 828, respectively. First detector 824 and second detector 840 can have any of the structures and functions discussed in the embodiments discussed in FIGS. 4-11. First detector 824 in first battery pack 812 and second detector 840 in second battery pack 828 sense conditions of first internal volume 820 and second internal volume 836, respectively. Conditions include presence of hydrogen gas, presence of carbon monoxide gas, and/or presence of infrared radiation, which indicate a battery cell in first battery modules 822 and/or second battery modules 838 are damaged. First detector 824 and second detector 840 transmit values representing the sensed conditions of first battery pack 812 and second battery pack 828 to controller 844 through electrical connections 806 of fire suppression system 800.

Controller 844 determines if the values representing the conditions of first intramodular volume 820 and second intramodular volume 836 indicate a fire event, as discussed in relation to FIGS. 4-11. Controller 844 triggers a first fire suppression procedure upon detection of a first fire event in first battery pack 812 or second battery pack 828. Controller 844 opens first inlet valve 814 and first outlet valve 827 or second inlet valve 830 and second outlet valve 843 (depending on where the first fire event is occurring). Controller 844 also opens first vessel valve 848 to release the first fire suppressant from first fire suppressant vessel 846. The first fire suppressant flows out of first fire suppressant vessel 846 and through check valve 854, and inlet line 808 into first battery pack 812 or second battery pack 828. The first fire suppressant can be any fire suppressant that provides cooling capabilities and does minimal, if any, damage to electrical components in first battery pack 812 and second battery pack 828. Example fire suppressants are discussed in relation to FIGS. 16-17 below. The first fire suppressant cools overheating battery cells in first battery pack 812 or overheating battery cells in second battery pack 828.

After the first fire suppression procedure, first detector 824 and second detector 840 continue sensing conditions of first internal volume 820 and second internal volume 836, respectively, and transmit values representing the conditions to controller 844, which then determines if a second fire event is occurring in first battery pack 812 or second battery pack 828. Controller 844 triggers a second fire suppression procedure based on if the conditions indicate a second fire event is occurring (as described in relation to FIGS. 4-11). The second fire suppression procedure is delayed from the first fire suppression procedure by the controller, allowing time for the first fire suppressant to cool battery storage area 802.

The second fire suppression procedure starts with controller 844 opening or closing first inlet valve 814 and first outlet valve 827 or second inlet valve 830 and second outlet valve 843 to open first battery pack 812 or second battery pack 828, as necessary. A battery pack is open if it is experiencing a fire event. A battery pack is closed if it is not experiencing a fire event. Controller 844 also opens second vessel valve 852 to release a second fire suppressant. Controller 844 can open second vessel valve 852 automatically based on programing or by a trigger from a vehicle operator. Alternatively, the operator can manually open second vessel valve 852. The second fire suppressant exits second fire suppressant vessel 850 and flows through check valve 854. Check valve 854 keeps the second fire suppressant from entering first fire suppressant vessel 846. The second fire suppressant flows through inlet line 808 and enters first battery pack 812 (if first inlet valve 814 and first outlet valve 827 are open) or second battery pack 828 (if second inlet valve 830 and second outlet valve 843 are open). The second fire suppressant cools first battery modules 822 or second battery modules 838, respectively. Once the second fire suppressant is evaporated, heated, or decomposed it becomes spent fire suppressant. The spent fire suppressant is vented from first battery pack 812 or second battery pack 828 through first outlet 826 or second outlet 842, respectively. First outlet 826 and second outlet 840 connect to outlet line 810 of fire suppression system 800, which then vents out of the vehicle. As described in relation to FIGS. 2 and 12, fire suppression system 800 can also connect to a fire suppressant disposal (suppressant disposal D), which can store spent fire suppressant for safe disposal or recycle spent fire suppressant for immediate reuse in fire suppression system 800.

System 800 provides capabilities for controller 844 to provide multiple fire suppressants to first battery pack 812 and/or second battery pack 828 during operation of a vehicle with system 800 installed. Increasing the amount of fire suppressant that can be delivered to first battery pack 812 and second battery pack 828 from one to two increases the amount of time an operator of a vehicle with system 800 installed has to respond to multiple fire events in battery storage area 802. If the vehicle is an aircraft, this allows the operator extra time to find a safe place to land before the fire event(s) become critical or threaten operator and passenger safety. Having more than one fire suppressant on board is helpful because overheating battery cells may continue to heat after a first fire suppressant is applied. Having first fire suppressant vessel 846 and second fire suppressant vessel 850 also allows for different chemical combinations of fire suppressant to be carried on-board. Check valve 854 is designed to aim fire suppressant towards inlet line 808 and not into an empty fire suppressant vessel after the first fire suppressant is released. System 800 also allows for targeted fire suppressants to be applied to fire events. For example, if first fire suppressant vessel 846 and second fire suppressant vessel 850 contain different fire suppressants, the vessels can be opened in any suitable order. The order can be determined based on the severity or location of the fire event and the chemical composition of the fire suppressants.

FIG. 15 is a flow chart showing method 860 of utilizing fire suppression system 800. Method 860 includes steps 862-874. Method 860 will be described with respect to system 800 of FIG. 14.

Step 862 includes sensing conditions indicating a fire event in first battery pack 812 and second battery pack 828. First detector 824 and second detector 840 sense conditions of first battery pack 812 and second battery pack 828, respectively. Conditions of first battery pack 812 and second battery pack 828 include a concentration of hydrogen gas, a concentration of carbon monoxide gas and/or presence of infrared radiation. First detector 824 and second detector 840 have configurations and operations as described in relation to FIGS. 4-11. Step 862 continues throughout method 860.

Step 864 includes transmitting values representing the detected conditions to controller 844. First detector 824 and second detector 840 transmit values representing the conditions of first battery pack 812 and second battery pack 828, respectively, to controller 844 via electrical connections 806 of fire suppression system 800. Transmission occurs as described in relation to FIGS. 4-11. Step 864 continues throughout method 860.

Step 866 includes determining, by controller 844, a first fire event is occurring in battery pack 812 and second battery pack 828. Controller 844 evaluates the values representing the detected conditions of first battery pack 812 and second battery pack 828 and determines if a first fire event is occurring in either first battery pack 812 or second battery pack 828. Controller 844 determines a first fire event is occurring based on comparing the values representing the sensed conditions to values that indicate a fire event, as described in relation to FIGS. 4-11.

Step 868 includes executing a first fire suppression procedure. The first fire suppression procedure includes at least four steps 868A-868D. Step 868A includes opening first inlet valve 814 and first outlet valve 827 to first battery pack 812 or second inlet valve 830 and second outlet valve 843 to second battery pack 828 depending on where the first fire event is occurring. Opening first inlet valve 814 and first outlet valve 827 opens first battery pack 812 to inlet line 808 of fire suppression system 800. Similarly, opening second inlet valve 830 and second outlet valve 843 opens second battery module to inlet line 808.

Step 868B of the first fire suppression procedure includes releasing a first pressurized fire suppressant by opening, with controller 844, first vessel valve 848 to first fire suppressant vessel 846. Controller 844 opens first vessel valve 848 to release the first fire suppressant from first fire suppressant vessel 846.

Step 868C of the first fire suppression procedure includes flowing the first fire suppressant into first battery pack 812 or second battery pack 828. The first fire suppressant flows through check valve 854 and inlet line 808 into first battery pack 812 or second battery pack 828. For example, if first inlet valve 814 and first outlet valve 827 are open, then the first fire suppressant will enter first battery pack 812. If second inlet valve 830 and second outlet valve 843 are open, then the first fire suppressant will enter second battery pack 828

Step 868D the first fire suppression procedure includes cooling first battery pack 812 or second battery pack 828 with the first fire suppressant. The first fire suppressant circulates around first battery pack 812 or second battery pack 828. The first fire suppressant cools the battery cells in first battery modules 822 or second battery modules 838 by evaporating and heat transfer. After evaporating, heating, or decomposing the first fire suppressant will become spent fire suppressant.

Step 870 includes determining, by controller 844, a second fire event is occurring in first battery pack 812 or second battery pack 828. Controller 844 uses values representing detected conditions received during steps 862 and 864, to determine if a second fire event is occurring in first battery pack 812 and second battery pack 828. Controller 844 determines if a second fire event is occurring in first battery pack 812 or the second battery pack 828, as described in relation to FIGS. 4-11. The second fire event can be a continuation of the first fire event or be a distinct fire event. The first fire event and the second fire event can occur in different battery modules.

Step 872 includes executing a second fire suppression procedure. Controller 844 can automatically trigger the second fire suppression procedure after determining there is a second fire event occurring. Alternatively, controller 844 can notify an operator and the operator can trigger the second fire suppression procedure. The second fire suppression procedure includes at least four steps 872A-872D.

Step 872A includes opening first inlet valve 814 and first outlet valve 827 to first battery pack 812 or second inlet valve 830 and second outlet valve 843 to second battery pack 828 by controller 844. Step 872A can also include closing first inlet valve 814 and first outlet valve 827 to first battery pack 812 or second inlet valve 830 and second outlet valve 843 to second battery pack 828, as necessary. A goal of step 872A is to have battery packs (812 or 828) experiencing the second fire event open to inlet line 808 and battery packs (812 or 828) not experiencing the second fire event closed to inlet line 808. For example, if first battery pack 812 is experiencing the second fire event and second battery pack 828 is not, then first inlet valve 814 and first outlet valve 827 will be open and second inlet valve 830 and second outlet valve 843 will be closed. Controller 844 will ensure first inlet valve 814 and second inlet valve 830 are in the appropriate configuration.

Step 872B of the second fire suppression procedure includes releasing a second pressurized fire suppressant by opening, with controller 844, second vessel valve 852 to second fire suppressant vessel 850.

Step 872C of the second fire suppression procedure includes flowing the second fire suppressant into first battery pack 812 or second battery pack 828. The second fire suppressant flows out of second fire suppressant vessel 850 through check valve 854, and inlet line 808 into first battery pack 812 or second battery pack 828. From there, the second fire suppressant flows through first inlet valve 814 into first battery pack 812 or through second inlet valve 830 into second battery pack 828.

Step 872D includes cooling first battery pack 812 or second battery pack 828 with the second fire suppressant. The second fire suppressant circulates around and cools first battery pack 812 or second battery pack 828. The second fire suppressant evaporates, heats, and decomposes to become spent fire suppressant.

Step 874 includes draining spent fire suppressant from first battery pack 812 through outlet 826 and/or from second battery pack 828 through outlet 842. Spent fire suppressant (from the first fire suppressant and/or the second fire suppressant) drains through first outlet 826 and/or second outlet 842. Spent fire suppressant includes heated first fire suppressant, chemically decomposed first fire suppressant, heated second fire suppressant, and/or chemically decomposed second fire suppressant. Step 874 can also occur between step 868 and step 872.

Method 860 supplies multiple fire suppressants to battery storage area 802. Fire suppressant can be applied twice to the same battery module or modules. For example, the first fire event and the second fire event can both occur in first battery pack 812 and the first fire suppressant and the second fire suppressant will both be applied to first battery pack 812. This can also be the case with just second battery pack 828 and both first battery pack 812 and second battery pack 828. Alternatively, the fire suppressants can be used in different battery modules. For example, the first fire event can occur in first battery pack 812 and the first fire suppressant will flow to first battery pack 812. Then, the second fire event can occur in second battery pack 828 and the second fire suppressant will be flowed to the second battery pack 828. Supplying two quantities of fire suppressant increases the ability of a vehicle with system 800 installed to contain a latent fire event and increases operators' opportunities to reach safety before being forced to land for a fire event. Method 860 allows for the second fire suppressant to be automatically or manually delivered into system 800.

Fire Suppressant Chemical Mixtures 900 and 930

Figure 16:
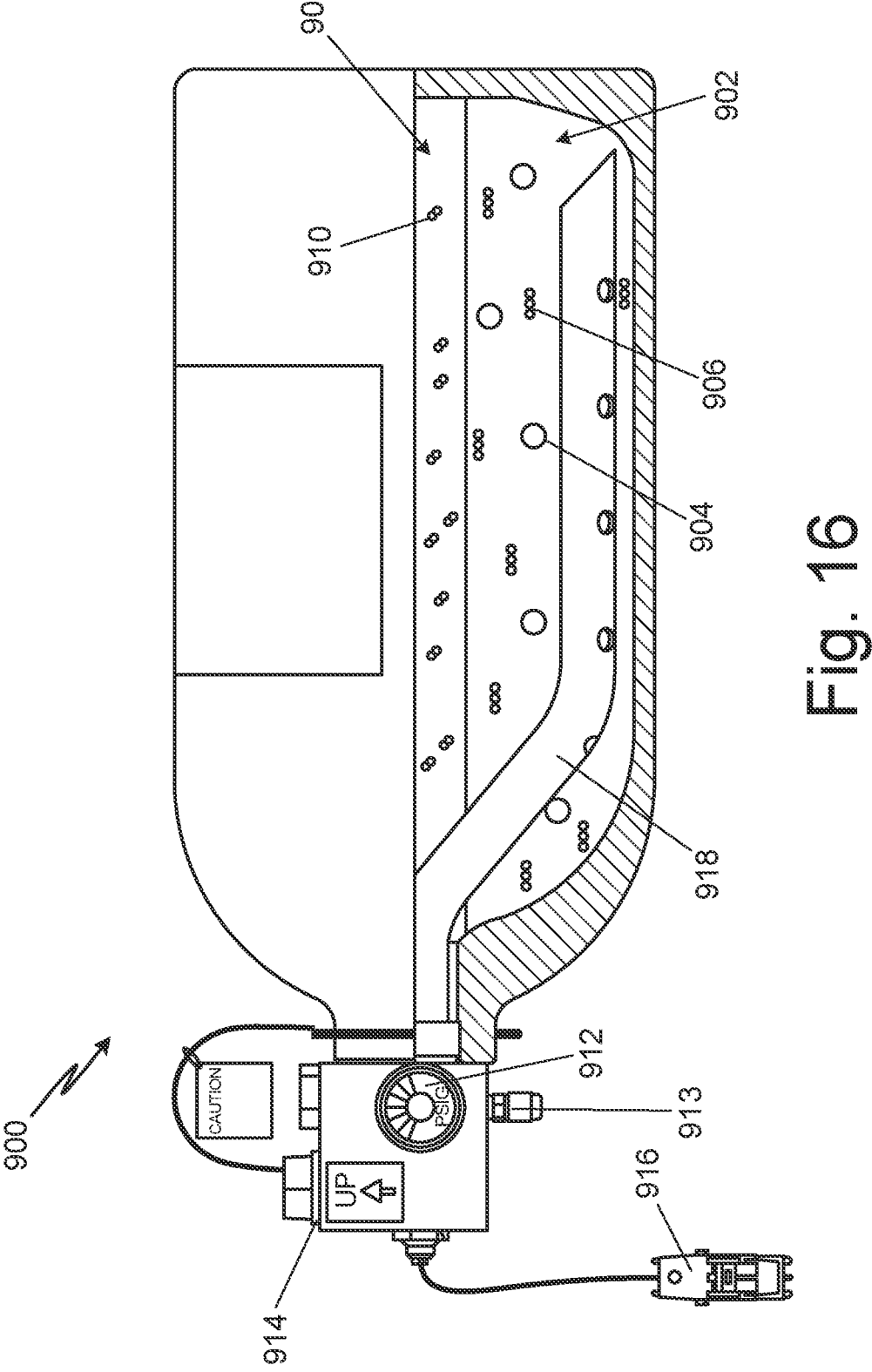
FIG. 16 is a schematic of a vessel with a first embodiment of a fire suppressant.

FIG. 16 is a schematic of vessel 900 with fire suppressant 902. Fire suppressant 902 includes dry chemical 904, and carbon dioxide 906. Vessel 900 also includes head space 908 with inert gas 910, pressure gauge 912, fill valve 913, outlet port 914, actuator 916, and siphon tube 918.

Vessel 900 has a cylindrical body. Vessel 900 can alternatively be any reasonable shape depending on amount of fire suppressant and space where vessel 900 is stored. For example, vessel 900 can be spherical. Fire suppressant 902 is stored pressurized in the cylindrical body of vessel 900. Carbon dioxide 906 is stored as a liquid and dry chemical 904 is stored in the liquid carbon dioxide 906. Head space 908 creates pressure in vessel 900 using inert gas 910. Pressure gauge 912 measures and displays pressure inside vessel 900. Pressure gauge 912 can alternatively be a pressure switch or a pressure transducer instead of a gauge. Fill valve 913 allows for charging vessel 900. Outlet port 914 is a port through which fire suppressant 902 flows when vessel 900 is discharged. Actuator 916 connects to a controller for a fire suppression system (for example, controller 144 of system 100 in FIG. 2). Actuator 916 can be, for example, a cartridge, a solenoid, or another method of releasing fire suppressant 902. Siphon tube 918 allows fire suppressant 902 to move out of vessel 900 when discharged. Siphon tube 918 is provided for horizontally mounted vessels as shown in FIG. 16. Alternatively, vessel 900 can be mounted vertically with outlet port 914 below the cylindrical body of vessel 900.

Vessel 900 is part of systems 100 of FIG. 1, 700 of FIGS. 12, and 800 of FIG. 14 including first fire suppressant vessel 146 and second fire suppressant vessel 150; fire suppressant vessel 746; and first fire suppressant vessel 846 and second fire suppressant vessel 850, respectively.

Fire suppressant 902 is a blend of carbon dioxide 906 and dry chemical 904. In fire suppressant 902, dry chemical 904 has a mass equivalent to 10% of the mass of carbon dioxide

906. For example, fire suppressant 902 includes 2 kilograms of carbon dioxide 906 and 200 g of dry chemical 904. Alternatively, the mass of dry chemical 904 can be anywhere between 5% and 50% the mass of carbon dioxide 906.

Dry chemical 904 is a non-flammable, particulate, inorganic chemical. Examples of dry chemical 904 include sodium bicarbonate, potassium bicarbonate and monoammonium phosphate. Monoammonium phosphate cannot be combined with either sodium bicarbonate or potassium bicarbonate. Dry chemical 904 has finely ground particles so that dry chemical 904 can be carried by a stream of carbon dioxide 906 and inert gas 910 when fire suppressant 902 is discharged from vessel 900. Particles of dry chemical 904 are ground to be between 1 micrometer and 100 micrometers. When dry chemical 904 is for example, sodium bicarbonate, particles are between 5 micrometers and 50 micrometers. To help dry chemical 904 flow out of vessel 900, Other additives can also be mixed into fire suppressant 902 including silica to help dry chemical 904 flow out of vessel 900, coloring agents, and hydrophobic coatings. A mixture of dry chemical 904 and other additives (silica, coloring agent, and hydrophobic coatings) is typically 10% other additives and 90% dry chemical. The mixture can have anywhere from 1%-10% other additives.

In vessel 900, carbon dioxide 906 is mostly in liquid form due to the amount of carbon dioxide 906 in vessel 900 and head space 908 created by inert gas 910 to increase the pressure in vessel 900. Small amounts of carbon dioxide 906 remain in gas form due to vapor pressure of carbon dioxide 906. Vapor pressure depends on the temperature surrounding vessel 900. For example, carbon dioxide 906 has a vapor pressure of 830 PSI at 21° C. As temperature around vessel 900 lowers below 21° C., vapor pressure of carbon dioxide 906 also lowers. Charging vessel 900 with carbon dioxide 906 alone is insufficient to ensure proper flow rate of fire suppressant 902 out of vessel 900 when temperatures are low. Filling vessel 900 with inert gas 910 at an overfill pressure of between 1000 PSIG and 1500 PSIG at 70° F. (20° C.) keeps carbon dioxide 906 sufficiently pressurized because the added pressure of inert gas 910 forces more carbon dioxide 906 into liquid phase and reduces the effects of temperature. The overfill pressure should be higher than the vapor pressure of carbon dioxide 906. Inert gas 910 can be any inert gas, for example, nitrogen, argon, helium, and combinations thereof. Inert gas 910 can also offer cooling properties when pressurized in vessel 900.

Storing carbon dioxide 906 as a liquid in vessel 900 ensures fire suppressant 902 is sufficiently cold when dispensed. Vaporized carbon dioxide cools dry chemical 904 when fire suppressant 902 is dispensed. Having cold fire suppressant 902 is important for stopping fire events in a battery pack (for example, battery pack 24 in FIG. 1, first battery pack 112 and second battery pack 128 of FIG. 2, etc.) because battery cells in the battery pack are often overheating or undergoing thermal runaway, which requires cooling to avoid damage to the battery pack. Storing carbon dioxide 906 as a liquid also reduces the amount of space needed for fire suppressant 902 because carbon dioxide has a much lower density as a liquid (773 kg/m$^3$ at 20° C.) than as a gas (1.9 kg/m$^3$ at 20° C.).

Fire suppressant 902 suppresses a fire event in a battery pack primarily by cooling battery cells in the battery pack. Fire suppressant 902 is cold because carbon dioxide 906 is stored as a liquid in vessel 900 and vaporizes when released from vessel 900 due to the reduced pressure after discharge. Dry chemical 904 is cooled by carbon dioxide 906 vaporizing when pressure is released and fire suppressant 902 is discharged from vessel 900. Actuator 916 connects to a controller (for example, controller 144 of FIG. 2). The controller release fire suppressant 902 from vessel 900 through outlet port 914. Fire suppressant 902 is forced out of vessel 900 by inert gas 910. Dry chemical 904 flows with carbon dioxide 906 and inert gas 910 out of vessel 900 and into a battery pack experiencing a fire event.

Dry chemical 904 coats components of the battery pack. Dry chemical 904 acts as a heat transfer layer to remove heat from the components of the battery pack into surrounding carbon dioxide 906 (or other cooling fluid). Dry chemical 904 also cools the battery pack components by removing heat to decompose dry chemical 904 into spent fire suppressant. Dry chemical 904 absorbs heat from the battery pack components and is cooled by carbon dioxide 906 in the battery pack. Dry chemical 904 provides prolonged cooling in the battery pack even after carbon dioxide 906 has evaporated, heated, and vented from the battery pack as spent fire suppressant because dry chemical 904 is cold at discharge and coats to the battery pack components.

Carbon dioxide 906 provides cooling as it evaporates in the battery pack. Carbon dioxide 906 has an evaporation point of −78° C. and a specific heat of 840 J/mol K. When fire suppressant 902 is released from vessel 900, carbon dioxide 906 will drop to a temperature near or at the evaporation point. The high specific heat means carbon dioxide 906 will absorb a lot of heat before boiling. Carbon dioxide 906 cools the components of the battery pack by directly absorbing heat from the battery pack components and from dry chemical 904. As carbon dioxide 906 absorbs heat, it will evaporate, heat, and become spent fire suppressant. Carbon dioxide 906 will drain from the battery pack as spent fire suppressant when the battery pack is full of fire suppressant.

Due to a primary focus on cooling for fire suppressant 902, more carbon dioxide 906 is flowed into the battery pack than the required inerting volume. An inerting volume is the concentration of carbon dioxide 906 necessary to smother a flame and prevent flame reignition when the concentration is maintained. The inerting volume is measured based on a size of the container with the flame. For example, approximately one-half of the free volume of a container is considered the inerting volume because it would take filling half of the container with carbon dioxide to smother a flame in the container. However, utilizing fire suppressant 902 in the battery pack may require more than the inerting volume of the battery pack because carbon dioxide 906 is acting as a coolant rather than only smothering a flame.

Use of vessel 900 and fire suppressant 902 will be discussed next. Use of fire suppressant 902 will be discussed in relation to system 700 of FIG. 12. However, vessel 900 can be incorporated as first fire suppressant vessel 146 and second fire suppressant vessel 150 of FIG. 2 or first fire suppressant vessel 846 and second fire suppressant vessel 850 of FIG. 14. Fire suppressant 932 can also be used in system 200 of FIG. 4, system 300 of FIG. 5, system 400 of FIG. 7, system 500 of FIG. 8, and system 600 of FIG. 10.

Vessel 900 and fire suppressant 902 can be used by first releasing fire suppressant 902 out of vessel 900. Opening outlet port 914 releases fire suppressant 902. Pressurized fire suppressant 902 then flows out of vessel 900. Fire suppressant 902 is a mixture of dry chemical 904 and carbon dioxide 906. Carbon dioxide 906 is pressurized and stored as a liquid in vessel 900. As such, carbon dioxide 906 is cooled by depressurization vaporization when released from vessel 900. Some carbon dioxide 906 may still be liquid in vessel 900 when discharged but will vaporize as it moves through a line and into a battery storage area (for example, battery storage area 102 in FIG. 2).

Fire suppressant 902 is then flowed into and throughout first battery pack 712 and/or second battery pack 728 in fire suppression system 700 (shown in FIG. 12). As discussed, fire suppressant 902 flows into first battery pack 712 and second battery pack 728 when first inlet valve 714 and second inlet valve 730 are open, respectively. Dry chemical 904 is carried on a stream of carbon dioxide through inlet line 708 into battery storage area 702. Inside first battery pack 712 and/or second battery pack 728, dry chemical 904 coats first battery modules 722 and/or second battery modules 738 as fire suppressant 902 flows through first battery pack 712 and/or second battery pack 728. An amount of carbon dioxide 906 flowed into the battery cell may be greater than an inerting quantity of carbon dioxide 906, as described above.

Overheating first battery modules 722 and/or second battery modules 738 are cooled with fire suppressant 902. Dry chemical 904 removes heat from overheating first battery modules 722 and/or second battery modules 738. Carbon dioxide 906 cools the dry chemical 904 and first battery modules 722 and/or second battery modules 738. Dry chemical 904 transfers heat from first battery modules 722 and/or second battery modules 738 into carbon dioxide 906. Carbon dioxide 906 evaporates and heats by absorbing heat from dry chemical 904. Absorbing heat from dry chemical 904 into carbon dioxide 906 delays decomposition of dry chemical 904. This extends the heat transfer capabilities of dry chemical 904 and prolongs cooling of first battery modules 722 and/or second battery modules 738.

Spent dry chemical 904 and heated carbon dioxide 906 are then removed from first battery pack 712 and/or second battery pack 728. Dry chemical 904 decomposes into spent dry chemical. Heated carbon dioxide 906 is gaseous. Gaseous carbon dioxide 906 is less dense and more voluminous than liquid carbon dioxide 906. Increased volume of carbon dioxide 906 may be larger than a volume of either first battery pack 712 or second battery pack 728 and will drain out of first battery pack 712 or second battery pack 728 and battery storage area 702 via outlet line 710. Spent dry chemical 904 will also flow out of first battery pack 712 and/or second battery pack 728. The volumetric increase and input of more fire suppressant 902 will cause spent fire suppressant 902 to flow out of battery storage area 702.

Figure 17:
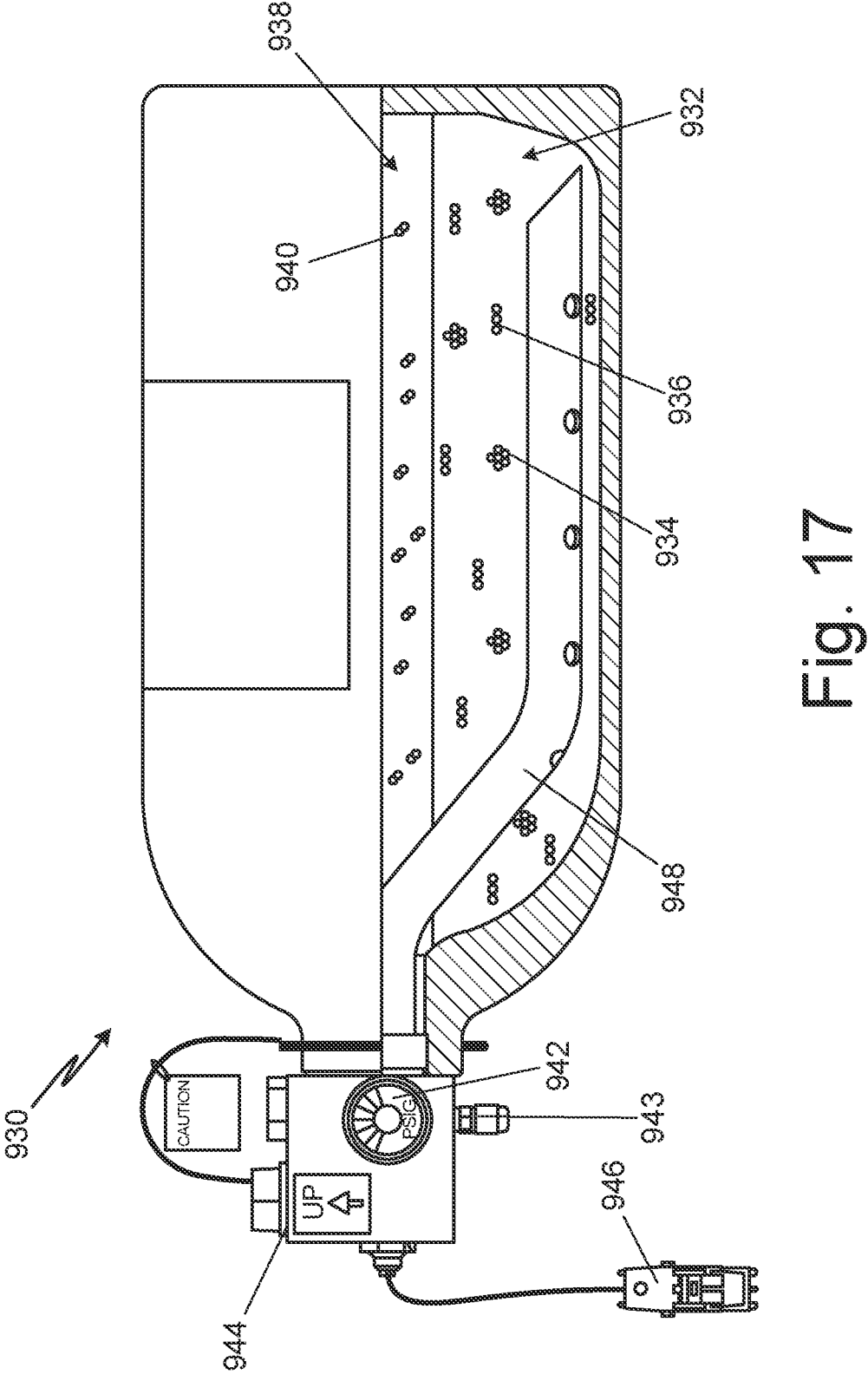
FIG. 17 is a schematic of a vessel with a second embodiment of a fire suppressant.

Additional carbon dioxide 906 or other fire suppressing agents (for example, fire suppressant 902 and fire suppressant 932 of FIG. 17) can be flowed into battery storage area 702 for additional fire suppression. This additional carbon dioxide 906 input may be delayed and may be an emergency fire suppressant, as described in relation to FIGS. 12-13. Flowing additional carbon dioxide 906 into first battery pack 712 and/or second battery pack 728 increases the cooling effect of dry chemical 904 and provides additional cooling.

Fire suppressant 902 is designed to suppress battery fire events in battery storage area 702. Fire suppressant 902 is non-conductive and non-corrosive fire suppression, meaning that it will not damage electronics or electrical components in battery storage area 702. Fire suppressant 902 can be cleaned out of first battery pack 712 and second battery pack 728. Fire suppressant 902 is also environmentally friendly. Fire suppressant 902 has a zero ozone-depletion potential (ODP) and a low global warming potential (GWP). The GWP is from carbon dioxide 906, which has a GWP of 1. Fire suppressant 902 is also green in that fire suppressant 902 prevents a need to clean up contaminated water (sometimes hundreds of gallons for a single fire event) or put toxic chemicals into the environment. Fire suppressant 902 also allows an opportunity for prolonged cooling by flowing an emergency source of cooled carbon dioxide 906 through battery storage area 702 while continuing to use dry chemical 904 within the battery storage area 702.

FIG. 17 is a schematic of vessel 930 with fire suppressant 932. Fire suppressant 932 includes organic compound 934, and carbon dioxide 936. Vessel 930 also includes head space 938 with inert gas 940, pressure gauge 942, fill valve 943, outlet port 944, actuator 946, and siphon tube 948.

Vessel 930 has a cylindrical body. Vessel 930 can alternatively have a different shape depending on volume of fire suppressant 932 being held in vessel 930 and the area where vessel 930 is stored. For example, vessel 930 can be spherical. Fire suppressant 932 is stored pressurized in vessel 930. Carbon dioxide 936 is stored as a liquid. Head space 938 creates pressure in vessel 930 using inert gas 940. Pressure gauge 942 measures and displays pressure inside vessel 930. Pressure gauge can alternatively be a pressure switch or a pressure transducer. Fill valve 943 is used to fill and charge vessel 930. Outlet port 944 is how fire suppressant 932 exits vessel 930. Actuator 946 connects to a controller for a fire suppression system (for example, controller 144 of system 100 in FIG. 2). Actuator 946 can be, for example, a cartridge, a solenoid, or any other mechanism to release fire suppressant 932. Siphon tube 948 is along a bottom of vessel 930. Siphon tube 948 is not necessary if vessel 930 is mounted so outlet port 944 is oriented down so that gravity can help release fire suppressant 932. Vessel 930 can be integrated into systems 100, 700, and 800 as first fire suppressant vessel 146 and second fire suppressant vessel 150 of FIG. 1; fire suppressant vessel 746 of FIG. 12; and first fire suppressant vessel 846 and second fire suppressant vessel 850 of FIG. 14.

Fire suppressant 932 is a blend of organic compound 934 and carbon dioxide 936. In fire suppressant 932, a ratio of a mass of organic compound 934 to a mass of carbon dioxide 936 is between 1:4 and 4:1. The ratio of the mass of organic compound 934 to the mass of carbon dioxide 936 is preferably 2:1. For example, fire suppressant 932 may have 2 kg of organic compound 934 1 kg carbon dioxide 936.

Organic compound 934 is a fluorinated ketone utilized to suppress fires. Organic compound 934 is preferably 1,1,1,2,2,4,4,5,5,5-nonafluoro-4-(trifluoromethyl)-3-pentanone (Novec 1230 produced by 3M™). Organic compound 934 has a purity grade greater than 99%. Organic compound 934 has a boiling point higher than room temperature (approximately 30° C.).

In vessel 930, carbon dioxide 936 is a liquid due to pressure created by inert gas 940. As discussed in relation to carbon dioxide 906 of FIG. 16, carbon dioxide 936 is stored mostly as a liquid due to inert gas 940 forcing more carbon dioxide 936 into liquid phase, especially at lower temperatures. Storing carbon dioxide 936 as a liquid in vessel 930 ensures fire suppressant 932 is sufficiently cold and pressurized when dispensed because carbon dioxide 936 cools as it vaporizes during discharge. When carbon dioxide 936 vaporizes at discharge, organic compound 934 is cooled and remains liquid until it reaches a battery pack (for example, first battery pack 712 or second battery pack 728 in FIG. 2). Having cold fire suppressant 932 is important for stopping fire events in a battery pack because battery cells in the battery pack are often overheating or undergoing thermal runaway, which requires cooling. Storing carbon dioxide 936 as a liquid also reduces the amount of space needed for fire suppressant 932 because carbon dioxide 936 has a much lower density as a liquid (773 kg/m³ at 20° C.) than as a gas (1.9 kg/m³ at 20° C.).

Inert gas 940 can be any inert gas, for example, nitrogen, argon, helium, and combinations thereof. Inert gas 940 pressurizes vessel 930 to keep flow rates of fire suppressant 932 sufficiently high to deliver fire suppressant 932 into a battery pack (for example, battery storage area 102 in FIG. 2). Carbon dioxide 936 has a vapor pressure of 830 PSI at 21° C. Due to the vapor pressure of carbon dioxide 936, charging vessel 930 with carbon dioxide 936 alone is insufficient to ensure proper flow rate of fire suppressant 902 out of vessel 930 when temperatures are low. Filling vessel 930 with inert gas 940 at an overfill pressure between 1000 PSIG and 1500 PSIG 70° F. (20° C.) keeps carbon dioxide 936 sufficiently pressurized. Inert gas 940 can also offer cooling properties when pressurized in vessel 930.

Fire suppressant 932 suppresses a fire event in a battery pack primarily by cooling battery cells in the battery pack. Fire suppressant 932 is cold because carbon dioxide 936 is stored as a liquid in vessel 930. Fire suppressant 932 is released from vessel 930 when outlet port 944 is opened. Fire suppressant 932 is forced out of vessel 930 by inert gas 940. Organic compound 934 flows with carbon dioxide 936 out of vessel 930 and into a battery pack experiencing a fire event.

Organic compound 934 coats components of the battery pack (for example, first battery modules 122 and/or second battery modules 138 in FIG. 2). Organic compound 934 absorbs heat from the battery pack components and evaporates. Organic compound 934 is cooled by carbon dioxide 936 in the battery pack. Organic compound 934 provides prolonged cooling in the battery pack even after carbon dioxide 936 has evaporated, heated, and drained from the battery pack as spent fire suppressant. Organic compound 934 does not leave residue in the battery pack once it has evaporated and is safe for electronic components because it is non-corrosive and non-conductive.

Carbon dioxide 936 provides cooling as it boils in the battery pack. Carbon dioxide 936 has a boiling point of −78° C. and a specific heat of 840 J/mol K. When fire suppressant 932 is released from vessel 930, carbon dioxide 936 drops to a temperature near or at the boiling point, which is low. The high specific heat means carbon dioxide 936 will absorb a lot of heat before boiling. Carbon dioxide 936 cools the components of the battery pack by directly absorbing heat from the battery pack components and from organic compound 934. As carbon dioxide 936 absorbs heat, it will boil (or evaporate) and become spent fire suppressant. Carbon dioxide 936 will drain from the battery pack when the battery pack is full and/or when carbon dioxide 936 is heated and evaporates.

Use of vessel 930 and fire suppressant 932 will be discussed next. Use of fire suppressant 932 will be discussed in relation to system 700 of FIG. 12. However, vessel 930 can be incorporated into system 100 and used as first fire suppressant vessel 146 and second fire suppressant vessel 150 of FIG. 2 or into system 800 first fire suppressant vessel 846 and second fire suppressant vessel 850 of FIG. 14. Fire suppressant 932 can also be used in system 200 of FIG. 4, system 300 of FIG. 5, system 400 of FIG. 7, system 500 of FIG. 8, and system 600 of FIG. 10.

Fire suppressant 932 can be used to cool first battery pack 712 or second battery pack 728 (shown in FIG. 12) by opening outlet port 944 and releasing a fire suppressant 932 out of vessel 930. Fire suppressant 932 is a mixture of organic compound 934 and carbon dioxide 936. Carbon dioxide 936 is liquid when pressurized and stored inside of vessel 930. As such, carbon dioxide 936 vaporizes and cools when released. Some of carbon dioxide 936 will be liquid as it exits vessel 930, but will vaporize in lines (for example, inlet line 708) as it moves into battery storage area 702. Pressurized fire suppressant 932 flows out of vessel 930 driven by inert gas 940.

Fire suppressant 932 then flows into battery storage area 702 by inlet line 708 and throughout first battery pack 712 or second battery pack 728 shown in FIG. 12. Fire suppressant 932 flows into and throughout first battery pack 712 if first inlet valve 714 is open. Fire suppressant 932 flows into and throughout second battery pack 728 if second inlet valve 730 is open. Fire suppressant 932 is directed through first battery pack 712 and second battery pack 728 by first nozzle 718 and second nozzle 734, respectively.

Fire suppressant 932 cools overheating battery cells in first battery modules 722 or second battery modules 738. In first battery pack 712 or second battery pack 728, organic compound 934 will absorb heat from the battery cells and vaporize near higher heat areas. Organic compound 934 was cooled by vaporizing carbon dioxide 936 at discharge from vessel 930 and has a higher heat absorption capability in first battery pack 712 or second battery pack 728, extending cooling.

Evaporated organic compound 934 and evaporated carbon dioxide 936 are then removed from battery storage area 702. Gaseous carbon dioxide 936 is less dense and more voluminous than liquid carbon dioxide 936. Increased volume of carbon dioxide 936 may be larger than a volume of first battery pack 712 and/or second battery pack 728. When evaporated, carbon dioxide 936 will drain from first battery pack 712 and/or second battery pack 728 because of the expanded gaseous volume. Evaporated organic compound 934 will also flow out of the battery module. Both evaporated carbon dioxide 936 and evaporated organic compound 934 will also be forced out of first battery pack 712 and/or second battery pack 728 as more fire suppressant 932 enters. An amount of carbon dioxide 936 flowed into the battery cell may be greater than an inerting quantity of carbon dioxide 936 because, as described above in relation to carbon dioxide 906 (shown in FIG. 16), the primary fire suppression method is cooling the battery cells. Suppressing flames can be an added benefit of using fire suppressant 932, however using more than an inerting volume increases cooling.

Optionally, additional carbon dioxide 936 or other fire suppressing agent (for example, fire suppressant 902 and fire suppressant 932) can be flowed into battery storage area 702 for continued cooling. Additional carbon dioxide 936 may be an emergency fire suppressant, as discussed in relation to FIGS. 12-13 above. Flowing additional carbon dioxide 936 into battery storage area 702 increases the cooling effect of organic compound 934 and provides additional cooling.

Fire suppressant 932 is designed to suppress battery fire events in battery storage area 702. Fire suppressant 932 is non-conductive and non-corrosive fire suppression, meaning that it will not damage electronics or electrical components in first battery pack 712 and second battery pack 728. Fire suppressant 932 does not leave residue in battery storage area 702 because organic compound 934 and carbon dioxide 936 evaporate. Fire suppressant 932 is also environmentally friendly. Fire suppressant 932 has a zero ozone-depletion potential (ODP) and a global warming potential (GWP) of 1 (from carbon dioxide 936). Fire suppressant 932 is also green in that fire suppressant 902 prevents a need to clean up contaminated water (sometimes hundreds of gallons for a single fire event) or put toxic chemicals into the environ-ment. Fire suppressant 932 also allows an opportunity for prolonged cooling by flowing an emergency source of cooled carbon dioxide 936 through the battery pack while continuing to use organic compound 934 within battery storage area 702.

Discussion of Possible Embodiments

The following are non-exclusive descriptions of possible embodiments of the present invention.

A gas detection system for a battery pack, includes a battery pack including a plurality of cells, a controller, and a detector. The detector is configured to sense a concentration value of one or more gases. The detector is electrically connected to the controller. The detector is configured to generate an alarm level return signal indicative of no alarm, a first alarm level, or a second alarm level based upon the concentration value of the one or more gases. The first detector is configured to transmit the alarm level return signal to the controller. The controller is configured to output no alarm, the first alarm, or the second alarm based upon the alarm level return signal received from the first detector.

The gas detection system of the preceding paragraph can optionally include, additionally and/or alternatively, any one or more of the following features, configurations and/or additional components:

In a further embodiment, the gas detection system further comprises a first port mounted on the exterior of the battery pack, wherein the first port provides access to an interior of the battery pack.

A further embodiment of any of the foregoing systems, wherein the detector is mounted on the first port.

A further embodiment of any of the foregoing systems, wherein one or more spaces exist between the plurality of cells.

A further embodiment of any of the foregoing systems, wherein the detector is mounted in the one or more spaces between the plurality of cells.

A further embodiment of any of the foregoing systems, wherein the plurality of cells are electrically connected in series to create a plurality of battery modules within the battery pack.

A further embodiment of any of the foregoing systems, wherein the first detector is configured to sense a first concentration of $H_2$ gas and sense a second concentration value of CO gas.

A further embodiment of any of the foregoing systems wherein the controller is configured to output the first alarm level if the first concentration value of $H_2$ gas is between 100 and 150 parts per million or if the second concentration value of CO gas is between 400 and 500 parts per million.

A further embodiment of any of the foregoing systems wherein the controller is configured to output the second alarm level if the first concentration value of $H_2$ gas is between 200 and 300 parts per million or if the second concentration value of CO gas is between 800 and 1000 parts per million.

A further embodiment of any of the foregoing systems further comprising a second detector in communication with the battery pack and electrically connected to the controller, wherein the second detector is configured to sense a concentration value of one or more gases.

A further embodiment of any of the foregoing systems, wherein the first detector is configured to sense a concentration value of $H_2$ gas within the battery pack and the second detector is configured to sense a concentration value of CO gas within the battery pack.

A method for detecting cell failure within the battery pack includes: sensing a concentration value of a first gas within a battery pack using a detector and sensing a concentration value of a second gas within a battery pack using the detector. The method further includes generating an alarm level return signal using the first detector based upon the first gas concentration value and the second gas concentration value. The alarm level return signal is indicative of no alarm, a first alarm, or a second alarm. The method further includes transmitting the alarm level return signal from the first detector to a controller and outputting no alarm, the first alarm, or the second alarm, via the controller, based upon the voltage return value from the first detector.

The method of the preceding paragraph can optionally include, additionally and/or alternatively, any one or more of the following features, configurations and/or additional components:

A further embodiment of any of the foregoing methods, wherein a first port mounted on the exterior of the battery pack provides access to an interior of the battery pack.

A further embodiment of any of the foregoing methods, wherein the detector is mounted on the first port.

A further embodiment of any of the foregoing methods, wherein the battery pack comprises a plurality of cells within the one or more spaces between the plurality of cells.

A further embodiment of any of the foregoing methods, wherein the detector is mounted within the one or more spaces between the plurality of cells.

A further embodiment of any of the foregoing methods, wherein the first gas is $H_2$ and the second gas is CO.

A further embodiment of any of the foregoing methods, wherein the method further comprises: outputting a first alarm condition if the concentration value of the first gas is between 100 and 150 parts per million or if the concentration value of the second gas is between 400 and 500 parts per million; and outputting a second alarm condition if the concentration value of the first gas is between 200 and 300 parts per million or if the concentration value of the second gas is between 800 and 1000 parts per million.

A further embodiment of any of the foregoing methods, wherein the method further comprises: outputting a signal, via the controller to turn off an outgassing cell if the first alarm condition or second alarm condition is met.

A further embodiment of any of the foregoing methods, wherein the method further comprises: outputting a signal, via the controller, to release a cooling agent into the battery pack if the second alarm condition is met.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A gas detection system for a battery pack, the gas detection system comprising:
   a battery pack comprising a plurality of cells;
   a controller;
   a first detector, in communication with the battery pack and configured to sense a concentration value of two or more gases, wherein:

the first detector is electrically connected to the controller;

the first detector is configured to generate an alarm level return signal indicative of no alarm, a first alarm, or a second alarm based upon the concentration value of the two or more gases wherein the first alarm is configured to be generated when a first concentration of a first gas is exceeded and/or a first concentration of a second gas is exceeded, and wherein the second alarm is configured to be generated when a second concentration of the first gas is exceeded and/or a second concentration of the second gas is exceeded;

the first detector is configured to transmit the alarm level return signal to the controller;

the controller is configured to output no alarm, the first alarm, or the second alarm based upon the alarm level return signal received from the first detector;

a second detector, in communication with the battery pack and configured to sense a concentration value of infrared radiation, wherein:

the second detector is electrically connected to the controller;

the second detector is configured to generate an alarm level return signal indicative of no alarm or a third alarm based upon the concentration value of the infrared radiation.

2. The gas detection system of claim 1, further comprising a first port mounted on an exterior of the battery pack, wherein the first port provides access to an interior of the battery pack.

3. The gas detection system of claim 2, wherein the first detector is mounted on the first port.

4. The gas detection system of claim 1, wherein one or more spaces exist between the plurality of cells.

5. The gas detection system of claim 1, wherein the first detector is mounted in the one or more spaces between the plurality of cells.

6. The gas detection system of claim 1, wherein the plurality of cells are electrically connected in series to create a plurality of battery modules within the battery pack.

7. The gas detection system of claim 1, wherein the first detector is configured to sense a first concentration value of $H_2$ gas and sense a second concentration value of CO gas.

8. The gas detection system of claim 7, wherein the controller is configured to output the first alarm if a first concentration value of $H_2$ gas is between 100 and 150 parts per million or if a second concentration value of CO gas is between 400 and 500 parts per million.

9. The gas detection system of claim 7, wherein the controller is configured to output the second alarm if the first concentration value of $H_2$ gas is between 200 and 300 parts per million or if the second concentration value of CO gas is between 800 and 1000 parts per million.

10. The gas detection system of claim 1, further comprising a second detector in communication with the battery pack and electrically connected to the controller, wherein the second detector is configured to sense a concentration value of one or more gases.

11. The gas detection system of claim 10, wherein the first detector is configured to sense a concentration value of $H_2$ gas within the battery pack and the second detector is configured to sense a concentration value of CO gas within the battery pack.

12. A method of detecting cell failure within a battery pack, the method comprising:

sensing a first gas within a battery pack using a first detector to produce a first gas concentration value;

sensing a second gas within the battery pack using the first detector to produce a second gas concentration value;

sensing a flame within the battery pack using a second detector to produce a infrared radiation value;

generating an alarm level return signal using the first detector based upon the first gas concentration value and the second gas concentration value, wherein the alarm level return signal is indicative of no alarm, a first alarm, or a second alarm, wherein the first alarm is configured to be generated when the first gas concentration value exceeds a first threshold value and/or a the second gas concentration value exceeds a second threshold value, and wherein the second alarm is configured to be generated when the first gas concentration value exceeds a third threshold value and/or a the second gas concentration value exceeds a fourth threshold value;

generating the alarm level return signal using the second detector based upon the infrared radiation value, wherein the alarm level return signal from the second detector is indicative of no alarm or a third alarm;

transmitting the alarm level return signal from the first detector and the second detector to the controller; and outputting no alarm, the first alarm, or the second alarm, via the controller, based upon the voltage return value from the first detector.

13. The method of claim 12, wherein a first port mounted on the exterior of the battery module provides access to an interior of the battery pack.

14. The method of claim 13, wherein the first detector is mounted on the first port.

15. The method of claim 12, wherein the battery pack comprises a plurality of cells with one or more spaces between the plurality of cells.

16. The method of claim 15, wherein the first detector is mounted within the one or more spaces between the plurality of cells.

17. The method of claim 12, wherein the first gas is $H_2$ and the second gas is CO.

18. The method of claim 17, further comprising:

outputting the first alarm if the first gas concentration value is between 100 and 150 parts per million or if the second gas concentration value is between 400 and 500 parts per million; and outputting a second alarm if the first gas concentration value is between 200 and 300 parts per million or if the second gas concentration value is between 800 and 1000 parts per million.

19. The method of claim 18, further comprising:

outputting a signal, via the controller, to turn off an outgassing cell if the first alarm or the second alarm is output by the controller.

20. The method of claim 19, further comprising:

outputting a signal, via the controller, to release a cooling agent into the battery pack if the second alarm is output by the controller.

\* \* \* \* \*